US007101989B1

(12) United States Patent
Elkins

(10) Patent No.: US 7,101,989 B1
(45) Date of Patent: Sep. 5, 2006

(54) DSRA PROTEIN AND POLYNUCLEOTIDES ENCODING THE SAME

(75) Inventor: Christopher Elkins, Chapel Hill, NC (US)

(73) Assignee: University of North Carolina at Chapel Hill, Chapel Hill, NC (US)

(*) Notice: Subject to any disclaimer, the term of this patent is extended or adjusted under 35 U.S.C. 154(b) by 596 days.

(21) Appl. No.: 10/030,529

(22) PCT Filed: Jul. 7, 2000

(86) PCT No.: PCT/US00/18834

§ 371 (c)(1),
(2), (4) Date: May 6, 2002

(87) PCT Pub. No.: WO01/04138

PCT Pub. Date: Jan. 18, 2001

Related U.S. Application Data

(60) Provisional application No. 60/143,257, filed on Jul. 9, 1999.

(51) Int. Cl.
C07H 21/04 (2006.01)
C12N 15/09 (2006.01)
C12P 21/04 (2006.01)
A61K 39/02 (2006.01)
A61K 39/102 (2006.01)

(52) U.S. Cl. .................. 536/23.7; 435/320.1; 435/69.3; 435/71.1; 424/234.1; 424/256.1; 424/184.1

(58) Field of Classification Search .............. 536/23.7; 435/320.1, 69.3, 71.1, 6; 424/234.1, 184.1, 424/256.1; 530/350, 300
See application file for complete search history.

(56) References Cited

U.S. PATENT DOCUMENTS

| | | | |
|---|---|---|---|
| 4,302,204 A | 11/1981 | Wahl et al. ................ 23/230.3 |
| 4,358,535 A | 11/1982 | Falkow et al. ................. 435/5 |
| 4,399,216 A | 8/1983 | Axel et al. ..................... 435/6 |
| 4,486,539 A | 12/1984 | Ranki et al. ................. 436/504 |
| 4,550,081 A | 10/1985 | Stocker ....................... 435/253 |
| 4,563,419 A | 1/1986 | Ranki et al. .................... 435/6 |
| 4,599,308 A | 7/1986 | Hamer et al. ................. 435/68 |
| 4,603,112 A | 7/1986 | Paoletti et al. .............. 435/235 |
| 4,745,051 A | 5/1988 | Smith et al. ................... 435/68 |
| 4,745,057 A | 5/1988 | Beckage et al. .............. 435/68 |
| 4,757,006 A | 7/1988 | Toole, Jr. et al. ............. 435/70 |
| 4,761,371 A | 8/1988 | Bell et al. ..................... 435/68 |
| 4,789,734 A | 12/1988 | Pierschbacher ............. 530/395 |
| 4,868,104 A | 9/1989 | Kurn et al. ..................... 435/6 |
| 4,877,729 A | 10/1989 | Clark et al. ................... 435/68 |
| 4,879,224 A | 11/1989 | Wallner et al. ............... 435/68 |
| 4,879,236 A | 11/1989 | Smith et al. ................. 435/235 |
| 4,912,038 A | 3/1990 | Schilling, Jr. et al. ...... 435/69.1 |
| 4,997,373 A | 3/1991 | Tanaka et al. ............... 433/204 |
| 5,023,243 A | 6/1991 | Tullis ........................... 514/44 |
| 5,077,393 A | 12/1991 | Hayashi ....................... 530/413 |
| 5,149,797 A | 9/1992 | Pederson et al. ............... 935/8 |
| 5,273,884 A | 12/1993 | Gale et al. ................... 435/7.1 |
| 5,389,518 A | 2/1995 | Steele et al. ............... 435/7.21 |
| 5,491,129 A | 2/1996 | Shaltiel ....................... 514/12 |
| 5,601,831 A | 2/1997 | Green et al. ............. 424/256.1 |
| 5,721,115 A | 2/1998 | Krivan et al. ............... 435/69.1 |
| 5,770,213 A | 6/1998 | Zlotnick .................. 424/256.1 |
| 5,866,132 A | 2/1999 | Malcolm .................. 424/193.1 |
| 5,912,234 A | 6/1999 | Ruoslahti et al. ............. 514/17 |
| 2004/0033585 A1* | 2/2004 | McCormick et al. .... 435/235.1 |

FOREIGN PATENT DOCUMENTS

EP 0 036 776 A2 9/1981
EP 0 073 657 B1 12/1990

OTHER PUBLICATIONS

Johansson et al. Infect. Immun. 70: 899-908, Feb. 2002 (abstract).*
Lewis DA. AIDS Patient Care STDS 14: 19-36, Jan. 2000 (abstract).*
Phillips AJ. J. Pharm. Pharmacol. 53: 1169-1174, 2001.*
Cole et al, "B-122 Expression of dsrA is required for efficient attachment of Haemophilus ducreyi to keratinocytes" Abstract Only, American Society for Microbiology 100th General Meeting, Los Angeles California May 21-25, 2000.
Skurnik et al., "Analysis of the yopA gene encoding the Yop1 virulence determinants of Yersinia spp." Molecular Microbiology, 3: 4, 5175-529 (1989).
Agrawal et al.; "Site-specific excision from RNA by RNase H and mixed-phosphate-backbone oligodeoxynucleotides" Proc. Natl. Acad. Sci. USA 87 1401-1405 (1990).
Albritton et al.; "Biology of Haemophilus ducreyi" Microbiological Reviews 53:4 377-389 (1989).
Alfa et al.; "Use of Tissue Culture and Animal Models to Identify Virulence-Associated Traits of Haemophilus dicreyi" Infection and Immunity 63:5 1754-1761 (1995).
Al-Tawfiq et al.; "An Isogenic Hemoglobin Receptor-Deficient Mutant of Haemophilus ducreyi Is Attenuated in the Human Model of Experimental Infection" The Journal of Infections Diseases 181 1049-1054 (2000).
Apicella et al.; "Phenotypic Variation in Epitope Expression of the Neisseria gonorrhoeae Lipooligosaccharide" Infection and Immunity 55:8 1755-1761 (1987).
Baker et al.; "Effects of oligo sequence and chemistry on the efficiency of oligoeoxyribonucleotide-mediated mRNA cleavage" Nucleic Acid Research 18:12 3537-3543 (1990).
Blaser et al.; "Role of the S-Layer Proteins of Campylobacter fetus in Serum-Resistance and Antigenic Variation: A Model of Bacterial Pathogenesis" The American Journal Of The Medical Sciences 306:5 325-329 (1993).

(Continued)

Primary Examiner—S. Devi
(74) Attorney, Agent, or Firm—Myers, Bigel, Sibley & Sajovec, P.A.

(57) ABSTRACT

DsrA is an outer membrane protein of H. ducreyi that confers serum resistance to the bacteria. Isolated polynucleotides encoding the protein, end expression vectors and host cells encoding the same, are described. Also described is a mutant H. ducreyi strain that does not express DsrA. Vaccines against H. ducreyi and methods of using the same are also described.

9 Claims, 12 Drawing Sheets

OTHER PUBLICATIONS

Bolivar et al.; "Construction and Characterization of New Cloning Vehicles" *Gene* 2 95-113 (1977).

Bozue et al.; "Facile construction of mutations in *Haemophilus ducreyi* using lacZ as a counter-selectable marker" *FEMS Microbiology Letters* 164 269-273 (1998).

Carson et al.; "Cloning and sequencing of a *Haemophilus ducreyi fur* homolog" *Gene* 176 125-129 (1996).

Chang et al.; "Phenotypic expression in *E.coli* of a DNA sequence coding for mouse dihydrofolate reductase" *Nature* 275 617-624 (1978).

Chen et al.; "Evaluation of Purified UspA from *Moraxella catarrhalis* as a Vaccine in a Murine Model after Active Immunization" *Infection and Immunity* 64:6 1900-1905 (1996).

Chen et al; "The Levels and Bactericidal Capacity of Antibodies Directed against the UspA1 and UspA2 Outer Membrane Proteins of *Moraxella* (*Branhamella*) *catarrhalis* in Adults and Children" *Infection and Immunity* 67:3 1310-1316 (1999).

Colbére-Garapin et al.; "A New Dominant Hybrid Selective Marker for Higher Eukaryotic Cells" *J. Mol. Biol.* 150 1-14 (1981).

Cole et al.; "Human monoclonal antibodies" *Molecular and Cellular Biochemistry* 62 109-120 (1984).

Corbeil; "Molecular Aspects of Some Virulence Factors of *Haemophilus somnus*" *Can. J. Vet. Res.* 54 S57-S62 (1990).

Cote et al.; "Generation of human monoclonal antibodies reactive with cellular antigens" *Proc. Natl. Acad. Sci. USA* 80 2026-2030 1983).

Crowe; "Chapter 55—Infections of the Immune System" 697-711.

De Boer et al.; "The tac promoter: A functional hybrid derived from the trp and lac promoters" *Proc. Natl. Acad. Sci.* 80 21-25 (1983).

Dixon et al.; "An Analysis of the Complete Nucleotide Sequence of the *Haemophilus duoreyl* Broad-Host-Range Plasmid pLS88" *Plasmid* 32 228-232 (1994).

Dutro et al.; "Prevalence of, Antibody Response to, and Immunity Induced by *Haemophilus ducreyi* Hemolysin" *Infection and Immunity* 67:7 3317-3328 (1999).

Elkins et al.; "Identification and Purification of a Conserved Heme-Regulated Hemoglobin-Binding Outer Membrane Protein from *Haemophilus ducreyi*" *Infection and Immunity* 63:4 1241-1245 (1995).

Elkins et al.; "Characterization of the hgbA Locus Encoding a Hemoglobin Receptor from *Haemophilus ducreyi*" *Infection and Immunity* 63:6 2194-2200 (1995).

Elkins; "Role of the *Haemophilus ducreyi* Ton System in Internalization of Heme from Hemoglobin" *Infection and Immunity* 66:1 151-160 (1998).

Elkins et al.; "Serum Resistance in *Haemophilus ducreyi* Requires Outer Membrane Protein DsrA" *Infection and Immunity* 68:3 1608-1619 (2000).

Fiers et al.; "Complete nucleotide sequence of SV40 DNA" *Nature* 273 113-119 (1978).

Furdon et al.; "Rnase H cleavage of RNA hybridized to oligonucleotides containing methylphosphonate, phosphorothioate and phosphodiester bonds" *Nucleic Acids Research* 17:22 9193-9204 (1989).

Goeddel et al.; "Direct expression in *Escherichia coli* of a DNA sequence coding for human growth hormone" *Nature* 281 544-548 (1979).

Goeddel et al.; "Synthesis of human fibroblast interferon by *E. coli*" *Nucleic Acids Research* 8:18 4057-4074 (1980).

Greenblatt et al.; "Genital ulceration as a risk factor for human immunodeficiency virus infection" *AIDS An International Bimonthly Journal* 2:1 47-50 (1988).

Grunstein et al.; "Colony hybridization: A method for the isolation of cloned DNAs that contain a specific gene" *Proc. Nat. Acad. Sci USA* 72:10 3961-3965 (1975).

Hansen et al.; "Use of Electroporation To Construct Isogenic Mutants of *Haemophilus ducreyi*" *Journal of Bacteriology* 174:16 5442-5449 (1992).

Hartman; "Two dominant-acting selectable markers for gene transfer studies in mammalian cells" *Proc. Natl. Acad. Sci. USA* 85 8047-8051 (1988).

Helminen et al.; "A Large, Antigenically Conserved Protein on the Surface of *Moraxella catarrhalis* Is a Target for Protective Antibodies" *The Journal of Infectious Diseases* 170 867-72 (1994).

Hess et al.; "Cooperation of Glycolytic Enzymes" *Advances in Enzyme Regulation* 7 149-167 (1969).

Hiltke et al.; Cloning of a gene encoding a 28 kilodalton outer membrane protein of *Haemophilus ducreyi* Abstract #B155; *Amer. Soc. Microbiol.* Las Vegas, Nevada (1994).

Hiltke et al.; "Characterization of a Novel Lipoprotein Expressed by *Haemophilus ducreyi*" *Infection and Immunity* 64:12 5047-5052 (1996).

Hiltke et al.; Effect of normal and immune sera on *Haemophilus ducreyi* 35000HP and its isogenic MOMP and LOS mutants *Microbial Pathogenesis* 26 93-102 (1999).

Hitchcock et al.; "Morphological Heterogeneity Among *Salmonella* Lipopolysaccharide Chemotypes in Silver-Stained Polyacrylamide Gels" *Journal of Bacteriology* 154:1 269-277 (1983).

Hitzeman et al.; "Isolation and Characterization of the Yeast 3-Phosphoglycerokinase Gene (PGK) by an Immunological Screening Technique" *The Journal of Biological Chemistry* 255:24 12073-12080 (1980).

Hol et al.; "Complement resistance is a virulence factor of *Branhamella* (*Moraxella*) *catarrhalis*" *FEMS Immunology and Medical Microbiology* 11 207-212 (1995).

Holland et al.; "Isolation and Identification of Yeast Messenger Ribonucleic Acids Coding for Enolase, Glyceraldehyde-e-phosphate Dehydrogenase, and Phosphoglycerate Kinase" *Biocehmistry* 17:23 4900-4907 (1978).

Huse et al.; "Generation of a Large Combinatorial Library of the Immunoglobulin Repertoire in Phage Lambda" *Science* 246 1275-1281 (1989).

Jessamine et al.; "Chancroid and the Role of Genital Ulcer Disease in the Spread of Human Retroviruses" *Medical Clinics of North America* 74:6 1417-1431 (1990).

Jones et al.; "Bipartite Structure of the ade3 Locus of *Saccharomyces cerevisiae*" *Genetics* 85 209-223 (1977).

Jones; "Proteinase Mutants of *Saccharomyces cerevisiae*" *Genetics* 85 23-33 (1977).

Kang et al.; "Antibody redesign by chain shuffling from random combinatorial immunoglobulin libraries" *Proc. Natl. Acad. Sci. USA* 88 11120-11123 1991).

Kennedy et al.; "Anti-Idiotypic Antibody Vaccine for Type B Viral Hepatitis in Chimpanzees" *Science* 232 220-223 (1986).

Kingsman et al.; "Replication in *Saccharomyces cerevisiae* Of Plasmid pBR313 Carrying DNA from the Yeast trpl Region" *Gene* 7 141-152 (1979).

Köhler et al.; "Continuous cultures of fused cells secreting antibody of predefined specificity" *Nature* 256 495-497 (1975).

Kozbor et al.; "Specific Immunoglobulin Production and Enhanced Tumorigenicity Following Ascites Growth of Human Hybridomas" *Journal of Immunological Methods* 81 31-42 (1985).

Kroll et al.; "A Multifunctional Prokaryotic Protein Expression System: Overproduction. Affinity Purification, and Selective Detection" *DNA and Cell Biology* 12:5 441-453 (1993).

Logan et al.; "Adenovirus tripartite leader sequence enhances translation of mRNAs late after infection" *Proc. Natl. Acad. Sci. USA* 81 3655-3659 (1984).

Lowy et al.; "Isolation of Transforming DNA: Cloning the Hamster aprt Gene" *Cell* 22 817-823 (1980).

Maddox et al.; "Elevated Scrum Levels in Human Pregnancy of a Molecule Immunochemically Similar to Eosinophil Granule Major Basic Protein" *J. Exp. Med.* 158 1211-1226 (1983).

McNamara et al.; "Monoclonal Idiotope Vaccine Against *Streptococcus pneumoniae* Infection", Abstract only (1984).

Merrifield; "Solid Phase Peptide Synthesis. I. The Synthesis of a Tetrapeptide" (1963).

Mobley et al.; "Virulence determinants of uropathogenic *Escherichia coli* and *Proteus mirabilis*" *Kidney International* 46:47 S129-S136 (1994).

Morrison et al.; "Chimeric human antibody molecules: Mouse antigen-binding domains with human constant region domains" *Proc. Natl. Acad. Sci. USA* 81 6851-6855 (1984).

Neuberger et al.; "Recombinant antibodies possessing novel effector functions" *Nature* 312 604-608 (1984).

Odumeru et al.; "Virulence Factors of *Haemophilus ducreyi*" *Infection and Immunity* 43:2 607-611 (1984).

Odumeru et al.; "Role of Lipopolysaccharide and Complement in Susceptibility of *Haemophilus ducreyi* to Human Serum" *Infection and Immunity* 50:2 495-499 (1985).

Odumeru et al.; "Relationship between lipopolysaccharide composition and virulence of *Haemophilus ducreyi*" *J. Med. Microbiol.* 23 155-167 (1987).

Oi et al.; "Chimeric Antibodies" *Biotechniques* 4:3 214-221 (1986).

Orlandi et al.; "Cloning immunoglobulin variable domains for expression by the polymerase chain reaction" *Proc. Natl. Acad. Sci. USA* 86 3833-3837 (1989).

Plummer et al.; "Detection of Human Immunodeficiency Virus Type I (HIV-1) in Genital Ulcer Exudate of HIV-1-Infected Men by Culture and Gene Amplification" *The Journal of Infectious Diseases* 161 810-811 (1990).

Porath et al.; "Immobilized Metal Ion Affinity Chromatography" *Protein Expression and Purification* 3 263-281 (1992).

Rhodes; "Chapter 9: Transformation of Maize by Electroporation of Embryos" *Plant Cell Electroporation and Electrofusion Protocols* (1995).

Rice; "Molecular Basis for Serum Resistance in *Neisseria gonorrhoeae*" *Clinical Microbiology Reviews* 2. Suppl. S112-S117 (1989).

Roggenkamp et al.; "Substitution of two histidine residues in YadA protein of *Yersinia enterocolitica* abrogates collagen binding, cell adherence and mouse virulence" *Molecular Microbiology* 16:6 1207-1219 (1995).

Roggenkamp et al.; "Deletion of Amino Acids 29 to 81 in Adhesion Protein YadA of *Yersinia enterocolitica* Serotype O:8 Results in Selective Abrogation of Adherence to Neutrophils" *Infection and Immunity* 64:7 2506-2514 (1996).

Sarkar et al. "Restriction-side PCR: A Direct Method of Unknown Sequence Retrieval Adjacent to a Known Locus by Using Universal Primers".

Siebenlist et al.; "*E. coli* RNA Polymerase Interacts Homologously with Two Different Promoters" *Cell* 20 269-281 (1980).

Scharf et al.; "6 Heat Stress Promoters and Transcription Factors" *Results and Problems in Cell Differentiation* 125-162 (1994).

Southern; "Detection of Specific Sequences Among DNA Fragments Separated by Gel Electrophoresis" *J. Mol. Biol.* 98 503-517 (1975).

Sproat et al.; "Highly efficient chemical synthesis of 2'-O-methyloligoribonucleotides and tetrabiotinylated derivatives novel probes that are resistant to degradation by RNA or DNA specific nucleases" *Nucleic Acids Research* 17:9 (1989).

Stevens et al.; A Hemoglobin-Binding Outer Membrane Protein Is Involved in Virulence Expression by *Haemophilus ducreyi* in an Animal Model 64:5 1724-1735 (1996).

Stinchcomb et al.; "Isolation and characterization of a yeast chromosomal replicator" *Nature* 282 39-43 (1979).

Struyvé et al; "Carboxy-terminal Phenylalanine is Essential for the Correct Assembly of a Bacterial Outer Membrane Protein" J. Mol. Biol. 218 141-148 (1991).

Stull et al.; "Epidemiology and Natural History of Urinary Tract Infections in Children" *Medical Clinics of North America* 75:2 287-297 (1991).

Sun et al.; Chimeric Antibodies with 17-1A-Derived Variable and Human Constant Regions *HYBRIDOMA* 5, Suppl. 1 S17-S20 (1986).

Takeda et al.; "Construction of chimaeric processed immunoglobulin genes containing mouse variable and human constant region sequences" *Nature* 314 452-454 (1985).

Tamm et al.; "Hydrophobic domains affect the collagen binding specificity and surface polymerization as well as the virulence potential of the YadA protein of *Yersinia enterocolitica*" *Molecular Microbiology* 10:5 995-1011 (1993).

Thomas et al.; "Pseudo-transposition of a Tn5 derivative in *Neisseria gonorrhoeae*" *FEMS Microbiology Letters* 145 371-376 (1996).

Thomas: "Hybridization of denatured RNA and small DNA fragments transferred to nitrocellulose" *Proc. Natl. Acad. Sci. USA* 77:9 5201-5205 (1980).

Tsai et al.; "A Sensitive Silver Stain for Detecting Lipopolysaccharides in Polyacrylamide Gels" *Analytical Biochemistry* 119 115-119 (1982).

Tschumper et al.; "Sequence of a yeast DNA fragment containing a chromosomal replicator and the TRP1 gene" *Gene* 10 157-166 (1980).

Walder et al.; "Role of RNase H in hybrid-arrested translation by antisense oligonucleotides" *Proc. Natl. Acad. Sci. USA* 85 5011-5015 (1988).

Wigler et al.; "Transfer of Purified Herpes Virus Thymidine Kinase Gene for Cultured Mouse Cells" *Cell* 11 223-232 (1977).

Wigler et al.; "Transformation of mammalian cells with an amplifiable dominant-acting gene" *Proc. Natl. Acad. Sci. USA* 77:6 3567-3570 (1980).

Winter et al.; "Man-made antibodies" *Nature* 349 293-299 (1991).

* cited by examiner

Fig. 3

```
  1  ATAAATACGTCATTGACATTTTTTTAATGTAAGGTAGAAGTAAATTCTATATTTACAATCAAGATTGACAATTATTTACTTAATGAGGTGATT
                    -35                                 -10                                    RBS

101  ATGAAAATTAAATGTTTAGTTGCCGTAGTGGGATTAGCTTGTTCTACTATTACAACAATGGCTCAGCAGCCGCCAAAGTTTGCTGGAGTATCTTCTTGT
  1   M  K  I  K  C  L  V  A  V  V  G  L  A  C  S  T  I  T  T  M  A  Q  Q  P  P  K  F  A  G  V  S  S  L  Y

201  ATAGCTATGAGTATGACTATGTAAGGTAAATGGACTTGGTCTCTAATGAAGGCGGTTTCGATATTAAAGTGCCAGGGATTAAAATGAAGCCAAAAGAATG
 35   S  Y  E  Y  D  Y  G  K  G  K  W  T  W  S  N  E  G  G  F  D  I  K  V  P  G  I  K  M  K  P  K  E  W

301  GATTTCTAAACAGGCTACTTATCTTGAATTACAGCATTATATGCCTTATACTCCTGTTCTCGTGACATATGCTCCTGGCGTTTCTCCTAGCCCTATACTG
 68   I  S  K  Q  A  T  Y  L  E  L  Q  H  Y  M  P  Y  T  P  V  L  V  T  Y  A  P  G  V  S  P  S  P  I  L

401  TTATATCCGATGTCTGATCCTGATCAACTTGGAATAAATCGGCAGCAGCTGAAATTGAATTTGTATAGTTATTTTAACGATTTAAGACACGATTTTAAAT
101   L  Y  P  M  S  D  P  D  Q  L  G  I  N  R  Q  Q  L  K  L  N  L  Y  S  Y  F  N  D  L  R  H  D  F  K  L

501  TAAAAGTTCTTGATGCACGTATTTCCAAAAATAAACAAATATTGATACTATAAGTAAATATTTACTAGAACTTGGTACTTATTTAGATGATTCTTATCG
135   K  V  L  D  A  R  I  S  K  N  K  Q  N  I  D  T  I  S  K  Y  L  L  E  L  G  T  Y  L  D  D  S  Y  R

601  TATGATGGAACAAAATACACATATAATCATAAGTTGTCTAAAGAATTGCAAACTGGTTTAGCCAACAATCAGCATTGTCTATGTTAGTGCAACCAAAT
168   M  M  E  Q  N  T  H  N  I  N  K  L  S  K  E  L  Q  T  G  L  A  N  Q  S  A  L  S  M  L  V  Q  P  N

701  GGTGTAGGCAAAACGAGCGTTTCTGCTGCGGTAGCGGTTATAGAGAGGTTATAGAGATAAAACTGCATTAGCCATTGGTGTCGGCTCACGCATTACTGATCGCTTTACCG
201   G  V  G  K  T  S  V  S  A  A  V  G  G  Y  R  D  K  T  A  L  A  I  G  V  G  S  R  I  T  D  R  F  T  A

801  CTAAAGCGGGTGTAGCCTTCAATACCTACAATGGCGGCATGTCTTATGGTGCTTCTGTTGGTTATGAATTCTAATCATTACGTTTAATCACTAATCGTTT
235   K  A  G  V  A  F  N  T  Y  N  G  G  M  S  Y  G  A  S  V  G  Y  E  F  *

901  TGGTTATAATAAAGGCTAAATGTTTCCTCCTCACATTTAGCCTTTCTTATTTATCTTTGTTATAGCTTTTGTCTGTTATAAAACCGTTTTTAGCCACTT
                                           <------------
```

Fig. 4

```
DsrA    1   -------------QQPPKF--------------------------------------------------------------------                                                            6
UspA2   1   QVVEQFFPNIFFNENHDELDDAYHNMILGDTAIVSNSQDNSTQLKFYSNDEDSVPDSLLFSKLLHEQQLNGFKAGDTIIPLDKGPVYT                                                              90
YadA    1   -----------------------------DDYDGIPNLTAVQISPNADPALGLEYPVRPPVPGA------------GGLNASAKGIHSIAIGATAEA---                                                56

DsrA    7   ----------------------------------------AGVSSDYSY------EY----DYG-------KGKWT----------------WSNE-                                                      29
UspA2   46  KDTRTKDGKVETVYSVTTKIATQDDVEQSAYSRGIQGDIDDLYDINREVNEMLKATHDYNERQTEAIDALNKASSANTDRIDTAEERIDK                                                              180
YadA    57  -------AKGAAVAVGAGSIATGVNS----------VAIGRL------SKALGD-----SAVTYGAASTAQKDGVAIGARASTSDTGVA-------                                                       117

DsrA    30  ---------------------------------GGEDIK---------VPGTKMKPKEWISKQATYEE-----------------------------                                                     55
UspA2   181 NEYDIKALESNVEEGLLELSGHLIDQKADLTKDIKALESNVEEGLLDLSGRLLDQKADIAK                                                                                           270
YadA    118 VGFNSKADAKN----------SVAIGHSSHVAANHGYSIAIGDRSKTDRENSVSIGHESLNRQLTHLAAGTKD---TDAVNVAQLKKEIEK                                                             195

DsrA    56  -----------------------LQHYMPYTPVLVTYAPGVSPSPILYPMSDBDQLGINRQQLKI-------NEYSYFNDL-RHDFKLKVLD-------ARIS-                                                121
UspA2   271 NQADIAQNQTDTODLAYNEQDAYAKQQMEAIDALNKASSENTONIAKNQADIANNINNIYELAQQDQHSSDIKTLAKASAANTDRIA                                                                  360
YadA    196 TQENTNKRSAELLANAN----AYADNKSSSV----LGIANNYTDSKSAETENARKEAFA----QSKDVLNMAKAHSNSVAR--                                                                    265

DsrA    122 --KNKQNIDTI---------------------------------------LEEGT------Y--------EDDS-                                                                            144
UspA2   361 KNKADADASFETLTKNQNTLIEKDKEHDKLITANKTAIDANKASADTKFAATADAITKNGNAITKNAKSIEDLGTKVDGFDGRVTALDTK                                                              450
YadA    266 ----TTLETAEEHANSV----ARTTLETAEE----HANKKSAEALASANVYADSKSSHTL-KTANSYTDVIVS----NSTKKAIRES-                                                                335

DsrA    145 YRMMEQNTHN---------UNKUSKEEQTGIANQSALSMLVQPNGVGKTSVSAAVGGYRDKTAIAIGVGSRITDRETAKAGVAENTMNGGM-SYG                                                         229
UspA2   451 MNAIDTKUNAFDGRITIALDSKVENGMAAAQAAISGIEFQPYSVGKFNATAALGGYGSKSAVAIGAGYRVNPNLAFKAGAAINTSGNKKGSYN                                                           540
YadA    336 NQYTDHKFRQLDNRLDKLDTRVDKGEASSAALNSLEQEYGVGKVNETAGVGGYRSSQALAIGSGYRVNENVALKAGVAYAGSSDVM--LN                                                              423

DsrA    230 ASVGYEE                                                                                                                                                236
UspA2   541 LGVNYEE                                                                                                                                                547
YadA    424 ASENLEW                                                                                                                                                430
```

Fig. 9

* = Variable Region 1
# = Variable Region 2 (Repeat Region)

Fig. 10

|  | -35 | -10 |
|---|---|---|
| 35000 | TTGACATTTTTTAATGTAAGGTAGAAT |
| CIP A75 | TTGACATTTTTTA-----AGGTAGAAT |
| CIP A77 | TTGACATTTTTTA-----AGGTAGAAT |
| CIP 542 (CAN) | TTGACATTTTTTAATGTAAGGTAGAAT |
| CIP 542 (CDC) | TTGACATTTTTTAATGTAAGGTAGAAT |
| CHIA | TTGACATTTCTTTAATGTAAGGTAAAAT |
| V-1157 | TTGACATTTTTTAATGTAAGGTAGAAT |
| M90-02 | TTGACATTTTTTAATGTAAGGTAGAAT |
| 406 | TTGACATTTTTTAATGTAAGGTAGAAT |

```
         10        20        30
```

U = Unlabeled OMP
1 = Surface-labeled *H. ducreyi* total protein
2 = Affinity purification, human native Vn
3 = Affinity purification, human recombinant Vn
4 = Affinity purification, bovine native Vn

DSRA PROTEIN AND POLYNUCLEOTIDES ENCODING THE SAME

This application claims priority to PCT Application number PCT/US00/18834 filed in English on Jul. 7, 2000 claming priority from U.S. Provisional Patent Application No. 60/143,257 filed on Jul. 9, 1999, the disclosures of which are hereby incorporated herein by reference in their entirety.

STATEMENT OF FEDERAL SUPPORT

This invention was made with United States Government support under grant numbers Al 40263 and A126837 from the National Institutes of Health (Public Health Service). The United States Government has certain rights to this invention.

FIELD OF THE INVENTION

This invention relates to proteins that are involved in the serum resistance of *H. ducreyi*.

BACKGROUND OF THE INVENTION

*Haemophilus ducreyi* is the etiologic agent of chancroid, a genital ulcer disease transmitted by sexual contact. See, e.g. Albritton, W. L., *Microbiol Rev.* 53:377–89 (1989); Trees, D. L., and S. A. Morse, *Clin Microbiol Rev.* 8, 357–375 (1995). Chancroid has gained importance recently because it has been implicated as an independent risk factor for the heterosexual transmission of HIV in Africa. See Albritton, supra Trees, supra: R. M. Greenblattet et al., *AIDS* 2, 47–50 (1988); Jessamine, P. G., and A. R. Ronald, *Med Clin North Am.* 74, 1417–31 (1990); Plummer, F. A. et al., *J Infect Dis.* 161, 810–1 (1990); D. L., and S. A. Morse, *Clin. Microbiol Rev.* 8, 357–375 (1995): Wasserheit, J. N., *Sex Trans Dis.* 19, 61–77 (1991).

Serum resistance has been shown in numerous bacterial systems to be critical for the survival of invading bacterial and the establishment of disease, since mutations which result in the loss of serum resistance renders several bacterial pathogens avirulent. See. e.g., Blaser, M. J., *American Journal of the Medical Sciences.* 306, 325–9 (1993); Corbeil, L. B., *Canadian Journal of Veterinary Research.* 54,S57–62 (1990), Mobley, H. L. et al., *Kidney International—Supplement.* 47, S129–36 (1994); Rice, P. A., *Clinical Microbiology Review.* 2, S112–7 (1989); and Stull, T. L., and J. J. LiPuma, *Medical Clinics of North America.* 75, 287–9 (1991). In most systems, the serum resistance phenotype is the product of multiple genes. *H. ducreyi* is resistant to high levels of normal human serum (NHS; up to 50%). Early studies on *H. ducreyi* serum resistance by Odumeru and colleagues concluded that truncation of LOS in several strains was associated with avirulence and loss of serum resistance (see Odumeru, J. A. et al., *Infect. Immun.* 43, 607–611 (1984); Odumeru, J. A. et al., *Infect. Immun.* 50, 495–9 (1985); Odumeru, J. A. et al., *J Med Microbiol.* 23, 155–62 (1987)), whereas a recent study came to the opposite conclusion. See Hiltke, T. J. et al., *Microb Path.* 26,93–102 (1999)

Originally described as a cell spreading factor, vitronectin is now recognized as a multifunctional regulatory adhesive glycoprotein involved in a variety of extracellular processes such as the attachment and spreading of normal and neoplastic cells, as well as the function of the complement and coagulation pathways. Integrins are transmembrane αβ heterodimer receptors expressed on a wide variety of cells which are involved in extracellular matrix interactions. The ligands for several of the integrins are adhesive extracellular matrix (ECM) proteins such as fibronectin, vitronectin, collagens and laminin.

Proteins or fragments thereof that are able to interfere with vitronectin binding to various integrins and to block integrin-mediated cell attachment to extracellular matrix proteins are useful in preventing the attachment of the bacteria to the host organism, and thus infection of the host.

The ability to use a protein or antibody that interferes with vitronectin binding in a vaccine against *H. ducreyi* is desirable. These kinds of proteins are believed to be highly conserved among strains of a particular type of bacteria in that they are the protein molecules that mediate attachment by bonding bacteria to host cells, the initial step in the infection process. A vaccine against *H. ducreyi* comprising a protein or antibody that would interfere with vitronectin binding would be effective against a broad array of types and strains of *H. ducreyi*. The use of such a vaccine may prevent adherence of the bacteria to the tissue of the host animal. In that adherence is one of the initial step in *H. ducreyi* infection, accordingly, preventing or limiting the infection at this point would be advantageous.

In view of the foregoing, it would be desirable to determine the mechanism of serum resistance in *H. ducreyi*. Additionally, the development of an effective vaccine against *H. ducreyi* would be advantageous.

SUMMARY OF THE INVENTION

Certain objects, advantages and novel features of the invention will be set forth in the description that follows, and will become apparent to those skilled in the art upon examination of the following, or may be learned with the practice of the invention.

The present invention is based in the inventor's discovery that a protein, referred to herein as DsrA (Ducreyi Serum Resistance A protein), has been found to play a critical role in the resistance of *H. ducreyi* to normal human serum.

Accordingly, one aspect of the invention is a polynucleotide (e.g., DNA) that encodes the protein DsrA. Particularly preferred is the DNA of SEQ ID NO:1, which encodes the protein DsrA set forth in SEQ ID NO:2.

An additional aspect of the invention is the isolated protein DsrA, which protein may vary in molecular weight between 28 and 35 kilodaltons, depending on whether the particular DsrA protein sequence comprises one, two or three copies of the amino acid heptamer NTHNINK (SEQ ID NO:19).

Expression vectors and host cells expressing DsrA are also an aspect of the invention. Antibodies against DsrA and antisense molecules of DsrA are a further aspect of the present invention.

Vaccines against *H. ducreyi* comprising proteins, polynucleotides and expression vectors of DsrA are a further aspect of the invention.

Also an aspect of this invention is an isogenic mutant (FX517) of *H. ducreyi* strain 35000 that does not express DsrA, which mutant finds use in an attenuated vaccine against *H. ducreyi*.

The foregoing and other aspects of the present invention are explained in detail in the specification set forth below.

BRIEF DESCRIPTION OF THE DRAWINGS

FIG. 3 sets forth the DNA sequence (SEQ ID NO:1) and deduced amino acid sequence (SEQ ID NO:2) of the dyrA locus. The putative −35 and −10 promoter sequences are indicated and underlined. A putative ribosome binding site is labeled RBS and underlined. Twenty one amino acids comprising the signal peptide are underlined. The stop codon TAA is indicated with an asterisk. The opposing arrows show a potential stem loop transcription terminator.

FIG. 4 sets forth a comparison of the amino acid sequence of DsrA (SEQ ID NO:2) with the UspA2 protein of *M. catarrahalis* (SEQ ID NO:20) and the YadA protein of *Y. enterocolitica* (SEQ ID NO:21). Shaded, boxed residues indicate homologous sequences.

FIG. 9 illustrates a comparison of the deduced amino acid sequences of dsrA from strain 35000 (SEQ ID NO:2) and eight additional *H. ducreyi* strains (CIP A75. SEQ ID NO:4. CIP A77. SEQ ID NO:6; CIP542 (CAN). SEQ ID NO:8; CIP542 (CDC), SEQ ID NO:10; CHIA, SEQ ID NO:12 V-1157. SEQ ID NO:14: M90-02. SEQ ID NO:16 and 406, SEQ ID NO:18). Variable regions 1 and 2 are indicated.

FIG. 10 illustrates the promoter regions of dsrA from various strains of *H. ducreyi* (35000, CIP542 (CAN), CIP542 (CDC). CHIA, V-1157, M90-02 and 406, SEQ ID NO:22, CIP A75 and CIP A77, SEQ ID NO:23) and the mutations in the strains CIP A75 and CIP A77, which do not express DsrA. The 5 base-pair deletions present in strains CIP A75 and CIP A77 are shown as hyphens.

DETAILED DESCRIPTION OF THE PREFERRED EMBODIMENTS

Figure 1:
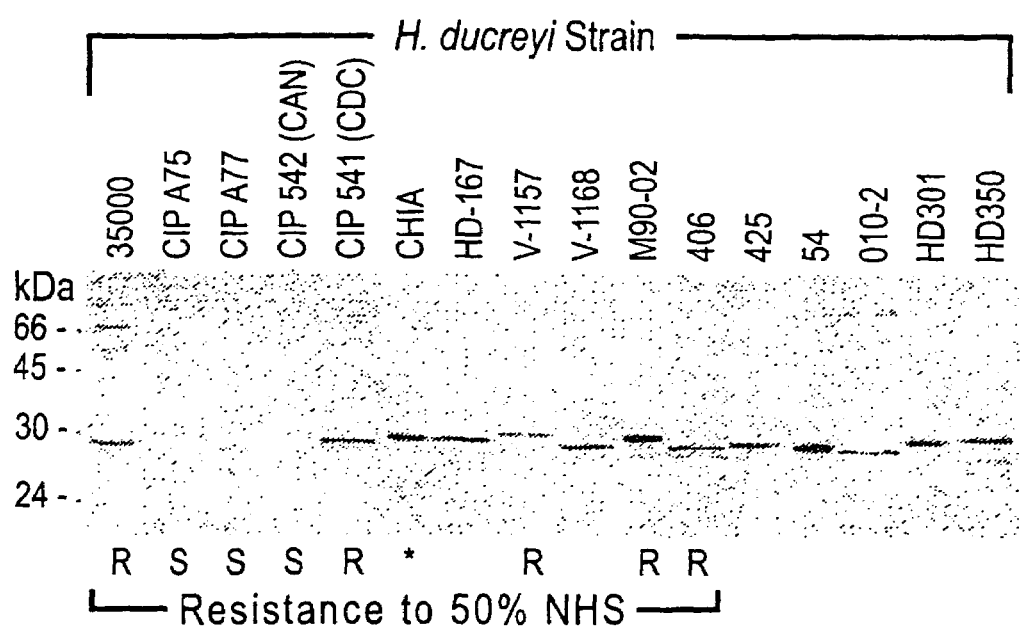
FIG. 1 is a photograph of Western Blot illustrating the distribution of the DsrA protein and summary of serum resistance of *H. ducreyi* strains. Total cellular proteins from geographically diverse *H. ducreyi* strains were subjected to SDS-PAGE and Western blotting using anti-DsrA mouse sera. Bound antibody was detected with alkaline phosphatase-conjugated secondary antibody and BCIP/NBT substrate. An additional twelve *H. ducreyi* strains also expressed a 28–35 kDa protein which reacted with this serum (data not shown). The names of strains are indicated above each lane. Shown to the left of the gel are molecular weight standards, where the abbreviation kDa means kilodaltons. R refers to resistant to 50% NHS; S, sensitive to 50% NHS, an asterisk indicates that resistance to NHS was indeterminate. The data in FIG. 1 are compiled from experiments done on at least three separate days.

The present invention will now be described more fully hereinafter with reference to the accompanying figures, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code, in accordance with 37 CFR § 1.822 and established usage. See, e.g., *Patent In User Manual*, 99–102 (November 1990) (U.S. Patent and Trademark Office).

DsrA is an *H. ducreyi* outer membrane protein required for the expression of serum resistance and is encoded by the gene dsrA, described herein. The isolated *H. ducreyi* protein DsrA, and the isolated polynucleotides that encode the protein, are aspects of the present invention. The DsrA protein in its monomer form varies in molecular weight between 28 and 35 kDA between different *H. ducreyi* strains in SDS-PAGE and Western blots. The dsrA locus from several *H. ducreyi* strains was sequenced and the deduced amino acid sequences were greater than 85% identical. The major difference between the different strains is found in the amino acid sequence, in which either one, two or three copies of the amino acid sequence NTHNINK (SEQ ID NO:19) are present in the VR2 region of the protein; these repeats account for the variability in the monomer form of the DsrA observed in SDS-PAGE. DsrA proteins that contain one, two or three copies of the NTHNINK (SEQ ID NO:19) in the VR2 region of the protein, and accordingly having a molecular weight of between 28 and 35 kilodaltons, are all within the scope of the present invention. Additionally, DsrA, as used herein, refers to the amino acid sequences of substantially purified DsrA obtained from any species, particularly mammalian, including bovine, ovine, porcine, murine, equine, and preferably human, from any source whether natural, synthetic, semi-synthetic, or recombinant.

As used herein, in this context, the term "isolated" means that the protein is significantly free of other proteins. That is, a composition comprising the isolated protein is between 70% and 94% pure by weight. Preferably, the protein is purified. As used herein, the term "purified" and related terms means that the protein is at least 95% pure by weight, preferably at least 98% pure by weight, and most preferably at least 99% pure by weight.

An "allele" as used herein, is an alternative form of the polynucleotides (i.e., genes) encoding DsrA. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Amino acid sequence," as used herein, refers to an oligopeptide, peptide, polypeptide, or protein sequence, and fragment thereof, and to naturally occurring or synthetic molecules. Fragments of DsrA are preferably and retain the biological activity or the immunological activity of DsrA. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification", as used herein, refers to the production of additional copies of a nucleic acid sequence and is generally carried out using polymerase chain reaction (PCR) technologies well known in the art (Dieffenbach, C. W. and G. S. Dveksler. *PCR Primer, a Laboratory Manual*, Cold Spring Harbor Press, Plainview, N.Y.(1995)).

As used herein, the term "antibody" refers to intact molecules as well as fragments thereof, such as Fa, F(ab')2, and Fc, which are capable of binding the DsrA protein or an antigenic or epitopic determinant thereof. Antibodies that bind DsrA polypeptides can be prepared using intact polypeptides or fragments containing small peptides of interest as an immunizing antigen. The polypeptide or oligopeptide may be used to immunize an animal and can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e. an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The terms "complementary" or "complementarity," as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial," in which only some of the nucleic acids bind, or it may be complete when total complementarity exists between the single stranded molecules. The degree of complementarity between nucleic acid strands has significant effects on the efficiency and strength of hybridization between nucleic acid strands.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to DsrA or the encoded DsrA. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

The term "hybridization", as used herein, refers to any process by which a strand of nucleic acid binds with a complementary strand through base pairing. The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g. $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

The term "sample", as used herein, is used in its broadest sense. A biological sample suspected of containing nucleic acid encoding DsrA, or fragments thereof, or DsrA itself may comprise a bodily fluid, extract from a cell, chromosome, organelle, or membrane isolated from a cell, a cell, genomic DNA, RNA, or cDNA (in solution or bound to a solid support, a tissue, a tissue print, and the like).

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors may be varied to generate conditions of either low or high stringency different from, but equivalent to, the above listed conditions.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

Polynucleotides of the present invention include those polynucleotides encoding for proteins homologous to, and having essentially the same biological properties as, the protein DsrA disclosed herein. Particularly preferred is the DNA disclosed herein as SEQ ID NO:1 and encoding the protein DsrA given herein SEQ ID NO:2. This definition of polynucleotides of the present invention is intended to encompass natural allelic sequences thereof. Accordingly, other preferred embodiments of the present invention include the polynucleotides set forth herein as SEQ ID NO:3, SEQ ID NO:5, SEQ ID NO:7, SEQ ID NO:9, SEQ ID NO:11, SEQ ID NO:13, SEQ ID NO:15, and SEQ ID NO:17, which polynucleotide sequences encode the protein sequences set forth as SEQ ID NO:4, SEQ ID NO:6, SEQ ID NO:8, SEQ ID NO:10, SEQ ID NO:12, SEQ ID NO:14, SEQ ID NO:16, and SEQ ID NO:18, respectively. Isolated DNA or cloned genes of the present invention can be of any species of origin, including mouse, rat, rabbit, cat, porcine, and human, but are preferably of mammalian origin. Polynucleotides that hybridize to any one of the DNA disclosed herein as SEQ ID NO:1, SEQ ID NO:3, SEQ ID NO:5, SEQ ID NO:7, SEQ ID NO:9, SEQ ID NO:11, SEQ ID NO:13, SEQ II) NO:15, or SEQ ID NO:17 (or fragments or derivatives thereof which serve as hybridization probes as discussed below) and which code on expression for a protein of the present invention (e.g. a protein according to SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18) are also an aspect of the invention. Conditions which will permit other polynucleotides that code on expression for a protein of the present invention to hybridize to the any one of DNA of SEQ ID NO:1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17 disclosed herein can be determined in accordance with known techniques. For example, hybridization of such sequences may be carried out under conditions of reduced stringency, medium stringency or even stringent conditions (e.g. conditions represented by a wash stringency of 35–40% Formamide with 5× Denhardt's solution, 0.5% SDS and 1× SSPE at 37° C.; conditions represented by a wash stringency of 40–45% Formamide with 5× Denhardt's solution, 0.5% SDS, and 1× SSPE at 42° C.; and conditions represented by a wash stringency of 50% Formamide with 5× Denhardt's solution, 0.5% SDS and 1× SSPE at 42° C., respectively) to any one of the DNA of SEQ ID NO:1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17 disclosed herein in a standard hybridization assay. See, e.g., J. Sambrook et al., *Molecular Cloning, A Laboratory Manual* (2d Ed. 1989) (Cold Spring Harbor Laboratory). In general, sequences which code for proteins of the present invention and which hybridize to any one of the DNA of SEQ ID NO:1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17 disclosed herein will be at least 75% homologous, 85% homologous, and even 95% homologous or more with the any one of SEQ ID NO:1. SEQ ID NO:3. SEQ ID NO:5, SEQ ID NO:7, SEQ ID NO:9, SEQ ID NO:11, SEQ ID NO:13, SEQ ID NO:15, or SEQ ID NO:17. Further, polynucleotides that code for proteins of the present invention, or polynucleotides that hybridize to any one of SEQ ID NO:1, SEQ ID NO:3, SEQ ID NO:5, SEQ ID NO:7, SEQ ID NO:9, SEQ ID NO:11, SEQ ID NO:13, SEQ ID NO:15, and SEQ ID NO:17, but which differ in codon sequence from any one of SEQ ID NO:1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17 due to the degeneracy of the genetic code, are also an aspect of this invention. The degeneracy of the genetic code, which allows different nucleic acid sequences to code for the same protein or peptide, is well known in the literature. See, e.g., U.S. Pat. No. 4,757,006 to Toole et al. at Col. 2, Table 1.

Although nucleotide sequences which encode DsrA and its variants are preferably capable of hybridizing to the nucleotide sequence of the naturally occurring DsrA under appropriately selected conditions of stringency, it may be advantageous to produce nucleotide sequences encoding DsrA or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding DsrA and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode DsrA and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding DsrA or any fragment thereof.

Knowledge of the nucleotide sequence as disclosed herein in SEQ ID NO:1, SEQ ID NO:3. SEQ ID NO:5, SEQ ID NO:7, SEQ ID NO:9, SEQ ID NO:11, SEQ ID NO:13, SEQ ID NO:15, and SEQ ID NO:17, can be used to generate hybridization probes which specifically bind to the DNA of the present invention or to mRNA to determine the presence of amplification or overexpression of the proteins of the present invention.

The production of cloned genes, recombinant DNA, vectors, transformed host cells, proteins and protein fragments by genetic engineering is well known. See, e.g., Sambrook et al., *Molecular Cloning: A Laboratory Manual* (Cold Spring Harbor, N.Y. Cold Spring Harbor Laboratory (1989)), as well as U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59. (Applicant specifically intends that the disclosure of all patent references cited herein be incorporated herein in their entirety by reference).

Methods for DNA sequencing which are well known and generally available in the art may be used to practice any of the embodiments of the invention. The methods may employ such enzymes as the Klenow fragment of DNA polymerase I, SEQUENASE® (US Biochemical Corp. Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding DsrA may be extended utilizing a partial nucleotide sequence and employing various methods known in the art to detect upstream sequences such as promoters and regulatory elements. For example, one method which may be employed. "restriction-site" PCR, uses universal primers to retrieve unknown sequence adjacent to a known locus (Sarkar. G. PCR Method Applic. 2,318–322 (1993)). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

A vector, as defined herein, is a replicable DNA construct. Vectors, such as plasmids, are used herein either to amplify DNA encoding the proteins of the present invention or to express the proteins of the present invention. An expression vector is a replicable DNA construct in which a DNA sequence encoding the proteins of the present invention is operably linked to suitable control sequences capable of effecting the expression of proteins of the present invention in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors, as used herein, include plasmids, viruses (e.g., adenovirus, cytomegalovirus), phage, retroviruses and integratable DNA fragments (i.e., fragments integratable into the host genome by recombination). The vector replicates and functions independently of the host genome, or may, in some instances, integrate into the genome itself. Expression vectors preferably contain a promoter and RNA binding sites which are operably linked to the gene to be expressed and are operable in the host organism.

DNA regions are operably linked or operably associated when they are functionally related to each other. For example, a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading phase.

Transformed host cells are cells which have been transformed or transfected with vectors containing DNA coding for proteins of the present invention need not express protein. Suitable host cells include prokaryotes, yeast cells, or higher eukaryotic organism cells. Prokaryote host cells include gram negative or gram positive organisms, for example *Escherichia coli* (*E. coli*) or Bacilli. Higher eukaryotic cells include established cell lines of mammalian origin as described below. Exemplary host cells are *E. coli* W3110) (ATCC 27.325), *E. coli* B, *E. coli* X1776 (ATCC 31,537), *E. coli* 294 (ATCC 31,446). A broad variety of suitable prokaryotic and microbial vectors are available. *E. coli* is typically transformed using a derivative of the plasmid pBR322. See Bolivar et al., *Gene* 2, 95 (1977). Promoters most commonly used in recombinant microbial expression vectors include the beta-lactamase (penicillinase) and lactose promoter systems (Chang et al., *Nature* 275, 615 (1978); and Goeddel et al., *Nature* 281, 544 (1979), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21 (1983). The promoter and Shine-Dalgarno sequence (for prokaryotic host expression) are operably linked to the DNA of the present invention, i.e., they are positioned so as to promote transcription of the messenger RNA from the DNA.

Expression vectors should contain a promoter which is recognized by the host organism. This generally means a promoter obtained from the intended host. While these are commonly used, other microbial promoters are suitable. Details concerning nucleotide sequences of many have been published, enabling a skilled worker to operably ligate them to DNA encoding the protein in plasmid or viral vectors (Siebenlist et al., *Cell* 20, 269 (1980). The promoter and Shine-Dalgarno sequence (for prokaryotic host expression) are operably linked to the DNA encoding the desired protein, i.e., they are positioned so as to promote transcription of the protein messenger RNA from the DNA.

Eukaryotic microbes such as yeast cultures may be transformed with suitable protein-encoding vectors. See e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the desired protein, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157(1980)). This plasmid contains the trp1 gene, which provides a selection marker for a mutant strain of yeast lacking the ability to grow in tryptophan, for example ATCC No. 44076 or PEP4-1 (Jones, *Genetics* 85, 12 (1977)). The presence of the trp1 lesion in the yeast host cell genome then provides an effective environment for detecting transformation by growth in the absence of tryptophan. Suitable promoting sequences in yeast vectors include the promoters for metallothionein, 3-phospho-glycerate kinase (Hitzeman et al., *J. Biol. Chem.* 255, 2073 (1980) or other glycolytic enzymes (Hess et al., *J. Adv. Enzyme Reg.* 7, 149 (1968); and Holland et al., *Biochemistry* 17, 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn, No. 73,657.

Cultures of cells derived from multicellular organisms are a desirable host for recombinant protein synthesis. In principal, any higher eukaryotic cell culture is workable, whether from vertebrate or invertebrate culture, including insect cells. Propagation of such cells in cell culture has become a routine procedure. See Tissue Culture, Academic Press, Kruse and Patterson, editors (1973). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599.308. The early and late promoters are useful because both are obtained easily from the virus as a fragment which also contains the SV40 viral origin of replication. See Fiers et al., *Nature* 273, 113 (1978). Further, the protein promoter, control and/or signal sequences, may also be used, provided such control sequences are compatible with the host cell chosen.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

Host cells such as insect cells (e.g., cultured *Spodoptera frugiperda* cells) and expression vectors such as the baculovirus expression vector (e.g. vectors derived from *Autographa californica* MNPV, *Trichoplusia ni* MNPV. *Rachiplusia ou* MNPV, or *Galleria ou* MNPV) may be employed to make proteins useful in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

In mammalian host cells, a number of viral-based expression systems may be utilized. In cases where an adenovirus is used as an expression vector, sequences encoding DsrA may be ligated into an adenovirus transcription/translation complex consisting of the late promoter and tripartite leader sequence. Insertion in a non-essential E1 or E3 region of the viral genome may be used to obtain a viable virus which is capable of expressing DsrA in infected host cells (Logan, J. and Shenk, T. (1984) *Proc. Natl. Acad. Sci.* 81:3655–3659). In addition, transcription enhancers, such as the Rous sarcoma virus (RSV) enhancer, may be used to increase expression in mammalian host cells. Rather than using vectors which contain viral origins of replication, one can transform mammalian cells by the method of cotransformation with a selectable marker and the chimeric protein DNA. An example of a suitable selectable marker is dihydrofolate reductase (DHFR) or thymidine kinase. See U.S. Pat. No. 4,399,216. Such markers are proteins, generally enzymes, that enable the identification of transformant cells. i.e. cells which are competent to take up exogenous DNA. Generally, identification is by survival or transformants in culture medium that is toxic, or from which the cells cannot obtain critical nutrition without having taken up the marker protein.

In general, those skilled in the art will appreciate that minor deletions or substitutions may be made to the amino acid sequences of peptides of the present invention without unduly adversely affecting the activity thereof. Thus, peptides containing such deletions or substitutions are a further aspect of the present invention. In peptides containing substitutions or replacements of amino acids, one or more amino acids of a peptide sequence may be replaced by one or more other amino acids wherein such replacement does not affect the function of that sequence. Such changes can be guided by known similarities between amino acids in physical features such as charge density, hydrophobicity/hydrophilicity, size and configuration, so that amino acids are substituted with other amino acids having essentially the same functional properties. For example: Ala may be replaced with Val or Ser; Val may be replaced with Ala, Leu, Met, or lie, preferably Ala or Leu; Leu may be replaced with Ala, Val or lie, preferably Val or Ile; Gly may be replaced with Pro or Cys, preferably Pro; Pro may be replaced with Gly, Cys, Ser, or Met, preferably Gly. Cys, or Ser; Cys may be replaced with Gly, Pro, Ser, or Met, preferably Pro or Met; Met may be replaced with Pro or Cys, preferably Cys; His may be replaced with Phe or Gln, preferably Phe; Phe may be replaced with His, Tyr, or Trp, preferably His or Tyr; Tyr may be replaced with His, Phe or Trp, preferably Phe or Trp; Trp may be replaced with Phe or Tyr, preferably Tyr; Asn may be replaced with Gln or Ser, preferably Gln; KGln may be replaced with His, Lys, Glu, Asn, or Ser, preferably Asn or Ser; Ser may be replaced with Gln, Thr, Pro, Cys or Ala; Thr may be replaced with Gln or Ser, preferably Ser; Lys may be replaced with Gln or Arg; Arg may be replaced with Lys, Asp or Glu, preferably Lys or Asp; Asp may be replaced with Lys, Arg, or Glu, preferably Arg or Glu; and Glu may be replaced with Arg or Asp, preferably Asp. Once made, changes can be routinely screened to determine their effects on function with enzymes.

As noted above, the present invention provides isolated and purified DsrA proteins, such as mammalian (or more preferably human) DsrA. Such proteins can be purified from host cells which express the same, in accordance with known techniques, or even manufactured synthetically.

Nucleic acids of the present invention, constructs containing the same and host cells that express the encoded proteins are useful for making proteins of the present invention. Specific initiation signals may also be used to achieve more efficient translation of polynucleotide sequences encoding DsrA. Such signals include the ATG initiation codon and adjacent sequences. In cases where sequences encoding DsrA, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. *Results Probl. Cell Differ.* 20,125–162(1994)). In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Manassas, Va.) and may be chosen to ensure the correct modification and processing of the foreign protein.

For long-term, high-yield production of recombinant proteins, stable expression is preferred. For example, cell lines which stably express DsrA may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type. Any number of selection systems may be used to recover transformed cell lines. These include, but are not limited to, the herpes simplex virus thymidine kinase (Wigler, M. et al. *Cell* 11, 223–32 (1977)) and adenine phosphoribosyltransferase (Lowy, I. et al., *Cell* 22, 817–23 (1980)) genes which can be employed in tk- or aprt-cells, respectively. Also, antimetabolite or antibiotic resistance can be used as the basis for selection; for example, dhfr which confers resistance to methotrexate (Wigler, M. et al., *Proc. Natl. Acad. Sci.* 77, 3567–70 (1980)); npt, which confers resistance to the aminoglycosides neomycin and G-418 (Colbere-Garapin, F. et al., *J. Mol. Biol.* 150,1–14 (1981)) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins. β-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest (i.e., dsrA) is also present, its presence and expression may need to be confirmed. For example, if the sequence encoding DsrA is inserted within a marker gene sequence, transformed cells containing sequences encoding DsrA can be identified by the absence of marker gene function. Alternatively, a marker gene can be placed in tandem with a sequence encoding DsrA under the control of a single promoter. Expression of the marker gene in response to induction or selection usually indicates expression of the tandem gene as well.

Alternatively, host cells which contain the nucleic acid sequence encoding DsrA and express DsrA may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of nucleic acid or protein.

As explained further herein, proteins of the present invention are useful as immunogens for making antibodies as described herein, and these antibodies and proteins provide a "specific binding pair." Such specific binding pairs are useful as components of a variety of immunoassays and purification techniques, as is known in the art. The proteins of the present invention are of known amino acid sequence as disclosed herein, and hence are useful as molecular weight markers in determining the molecular weights of proteins of unknown structure.

The presence of polynucleotide sequences encoding DsrA can be detected by DNA—DNA or DNA-RNA hybridization or amplification using probes or fragments or fragments of polynucleotides encoding DsrA. Nucleic acid amplification based assays involve the use of oligonucleotides or oligomers based on the sequences encoding DsrA to detect transformants containing DNA or RNA encoding DsrA.

A variety of protocols for detecting and measuring the expression of DsrA, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on DsrA is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; *J. Exp. Med.* 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding DsrA include oligolabeling, nick translation, end-labeling or PCR amplification using a labeled nucleotide. Alternatively, the sequences encoding DsrA, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland. Ohio)). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding DsrA may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode DsrA may be designed to contain signal sequences which direct secretion of DsrA through a prokaryotic or eukaryotic cell membrane. Other constructions may be used to join sequences encoding DsrA to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and DsrA may be used to facilitate purification. One such expression vector provides for expression of a fusion protein containing DsrA and a nucleic acid encoding 6 histidine residues preceding a thioredoxin or an enterokinase cleavage site. The histidine residues facilitate purification on IMAC (immobilized metal ion affinity chromatography) as described in Porath, J. et al., *Prot. Exp. Purif.* 3, 263–281 (1992)) while the enterokinase cleavage site provides a means for purifying DsrA from the fusion protein. A discussion of vectors which contain fusion proteins is provided in Kroll, D. J. et al., *DNA Cell Biol.* 12, 441–453 (1993)).

In addition to recombinant production, fragments of DsrA may be produced by direct peptide synthesis using solid-phase techniques (Merrifield J. *J. Am. Chem. Soc.* 85, 2149–2154 (1963)). Protein synthesis may be performed using manual techniques or by automation. Automated synthesis may be achieved, for example, using Applied Biosystems 431A Peptide Synthesizer (Perkin Elmer). Various fragments of DsrA may be chemically synthesized separately and combined using chemical methods to produce the full length molecule.

Antibodies that specifically bind DsrA (i.e., antibodies which bind to a single antigenic site or epitope on the proteins) are useful for a variety of diagnostic and therapeutic purposes. Antibodies to DsrA may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with DsrA or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

Monoclonal antibodies to DsrA may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) *Nature* 256:495–497; Kozbor, D. et al. (1985) *J. Immunol. Methods* 81:31–42; Cote, R. J. et al. (1983) *Proc. Natl. Acad. Sci.* 80:2026–2030; Cole, S. P. et al. (1984) *Mol. Cell Biol.* 62:109–120). Briefly, the procedure is as follows: an animal is immunized with DsrA or immunogenic fragments or conjugates thereof. For example, haptenic oligopeptides of DsrA can be conjugated to a carrier protein to be used as an immunogen. Lymphoid cells (e.g. splenic lymphocytes) are then obtained from the immunized animal and fused with immortalizing cells (e.g. myeloma or heteromyeloma) to produce hybrid cells. The hybrid cells are screened to identify those which produce the desired antibody.

Human hybridomas which secrete human antibody can be produced by the Kohler and Milstein technique. Although human antibodies are especially preferred for treatment of human, in general, the generation of stable human—human hybridomas for long-term production of human monoclonal antibody can be difficult. Hybridoma production in rodents, especially mouse, is a very well established procedure and thus, stable murine hybridomas provide an unlimited source of antibody of select characteristics. As an alternative to human antibodies, the mouse antibodies can be converted to chimeric murine/human antibodies by genetic engineering techniques. See V. T. Oi et al., *Bio Techniques* 4(4):214–221 (1986); L. K. Sun et al., *Hybridoma* 5 (1986).

The monoclonal antibodies specific for DsrA epitopes can be used to produce anti-idiotypic (paratope-specific) antibodies. See e.g., McNamara et al., Dec. 14, 1984, Science, page 1325; Kennedy, R. C. et al., (1986) Science 232:220. These antibodies resemble the DsrA epitope and thus can be used as an antigen to stimulate an immune response against *H. ducreyi*.

In addition, techniques developed for the production of "chimeric antibodies", the splicing of mouse antibody genes to human antibody genes to obtain a molecule with appropriate antigen specificity and biological activity can be used (Morrison, S. L. et al. (1984) *Proc. Natl. Acad. Sci.* 81, 6851–6855; Neuberger, M. S. et al. (1984) *Nature* 312: 604–608; Takeda, S. et al. (1985) *Nature* 314:452–454). Alternatively, techniques described for the production of single chain antibodies may be adapted, using methods known in the art, to produce DsrA-specific single chain antibodies. Antibodies with related specificity, but of distinct idiotypic composition, may be generated by chain shuffling from random combinatorial immunoglobin libraries (Burton D. R. (1991) *Proc. Natl. Acad. Sci.* 88,11120–3).

Antibodies may also be produced by inducing in vivo production in the lymphocyte population or by screening immunoglobulin libraries or panels of highly specific binding reagents as disclosed in the literature (Orlandi, R. et al., *Proc. Natl. Acad. Sci.* 86, 3833–3837 (1989)); Winter, G. et al., (1991) *Nature* 349, 293–299 (1991)).

Antibody fragments which contain specific binding sites for DsrA may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between DsrA and its specific antibody. A two-site, monoclonal-based immunoassay utilizing monoclonal antibodies reactive to two non-interfering DsrA epitopes is preferred, but a competitive binding assay may also be employed (Maddox, supra).

Antibodies may be conjugated to a solid support suitable for a diagnostic assay (e.g., beads, plates, slides or wells formed from materials such as latex or polystyrene) in accordance with known techniques, such as precipitation. Antibodies may likewise be conjugated to detectable groups such as radiolabels (e.g., $^{35}S$, $^{125}I$, $^{131}I$), enzyme labels (e.g., horseradish peroxidase, alkaline phosphatase), and fluorescent labels (e.g., fluorescein) in accordance with known techniques.

The proteins and peptides of this invention may be used as antigens in immunoassays for the detection of *H. ducreyi* in various tissues and body fluids e.g., blood, spinal fluid, sputum, etc. A variety of immunoassay systems may be used. These include: radio-immunoassays, ELISA assays, "sandwich" assays, precipitin reactions, gel diffusion precipitin reactions, immunodiffusion assays, agglutination assays, fluorescent immunoassays, protein A immunoassays and immunoelectrophoresis assays.

In addition, nucleic acids having the nucleotide sequences of the gene encoding DsrA or any nucleotide sequences which hybridize therewith can be used as probes in nucleic acid hybridization assays for the detection of *H. ducreyi* in various tissues or body fluids of patients. The probes may be used in any nucleic any type of hybridization assay including: Southern blots (Southern, 1975, J. Mol. Biol. 98:508); Northern blots (Thomas et al., 1980, Proc. Nat'l Acad. Sci. U.S.A. 77:5201–05); colony blots (Grunstein et al., 1975. Proc. Nat'l Acad. Sci. U.S.A. 72:3961–65), etc. Stringency of hybridization can be varied depending on the requirements of the assay. Assays for detecting the polynucleotides encoding DsrA in a cell, or the extent of amplification thereof, typically involve, first, contacting the cells or extracts of the cells containing nucleic acids therefrom with an oligonucleotide that specifically binds to DsrA polynucleotide as given herein (typically under conditions that permit access of the oligonucleotide to intracellular material), and then detecting the presence or absence of binding of the oligonucleotide thereto. Again, any suitable assay format may be employed (see, e.g., U.S. Pat. No. 4,358,535 to Falkow et al.; U.S. Pat. No. 4,302,204 to Wahl et al.; U.S. Pat. No. 4,994,373 to Stavrianopoulos et al; U.S. Pat. No. 4,486,539 to Ranki et al.; U.S. Pat. No. 4,563,419 to Ranki et al.; and U.S. Pat. No. 4,868,104 to Kurn et al.) (the disclosures of which applicant specifically intends be incorporated herein by reference).

Kits for determining if a sample contains proteins of the present invention will include at least one reagent specific for detecting the presence or absence of the protein. Diagnostic kits for carrying out antibody assays may be produced in a number of ways. In one embodiment, the diagnostic kit comprises (a) an antibody which binds proteins of the present invention conjugated to a solid support and (b) a second antibody which binds proteins of the present invention conjugated to a detectable group. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like. A second embodiment of a test kit comprises (a) an antibody as above, and (b) a specific binding partner for the antibody conjugated to a detectable group. Ancillary agents as described above may likewise be included. The test kit may be packaged in any suitable manner, typically with all elements in a single container along with a sheet of printed instructions for carrying out the test.

Antisense oligonucleotides and nucleic acids that express the same may be made in accordance with conventional techniques. See, e.g. U.S. Pat. No. 5,023,243 to Tullis; U.S. Pat. No. 5,149,797 to Pederson et al. The length of the antisense oligonucleotide (i.e., the number of nucleotides therein) is not critical so long as it binds selectively to the intended location, and can be determined in accordance with routine procedures. In general, the antisense oligonucleotide will be from 8, 10 or 12 nucleotides in length up to 20, 30, or 50 nucleotides in length. Such antisense oligonucleotides may be oligonucleotides wherein at least one, or all, or the internucleotide bridging phosphate residues are modified phosphates, such as methyl phosphonates, methyl phosphonothioates, phosphoromorpholidates, phosphoropiperazidates and phosphoramidates. For example, every other one of the internucleotide bridging phosphate residues may be modified as described. In another non-limiting example, such antisense oligonucleotides are oligonucleotides wherein at least one, or all, of the nucleotides contain a 2' loweralkyl moiety (e.g., $C_1$–$C_4$, linear or branched, saturated or unsaturated alkyl, such as methyl, ethyl, ethenyl, propyl, 1-propenyl, 2-propenyl, and isopropyl). For example, every other one of the nucleotides may be modified as described. See also P. Furdon et al., *Nucleic Acids Res.* 17, 9193–9204 (1989); S. Agrawal et al., *Proc. Natl. Acad. Sci. USA* 87, 1401–1405 (1990); C. Baker et al., *Nucleic Acids Res.* 18, 3537–3543 (1990); B. Sproat et al., *Nucleic Acids Res.* 17, 3373–3386 (1989); R. Walder and J. Walder, *Proc. Natl. Acad. Sci. USA* 85, 5011–5015 (1988).

In another embodiment of the invention, DsrA, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between DsrA and the agent being tested, may be measured.

Another technique for drug screening which may be used provides for high throughput screening of compounds having suitable binding affinity to the protein of interest as described in published PCT application WO84/03564. In this method, as applied to DsrA, large numbers of different small test compounds are synthesized on a solid substrate, such as plastic pins or some other surface. The test compounds are reacted with DsrA, or fragments thereof, and washed. Bound DsrA is then detected by methods well known in the art. Purified DsrA can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding DsrA specifically compete with a test compound for binding (DsrA. In this manner, the antibodies can be used to detect the presence of any peptide which shares one or more antigenic determinants with DsrA.

The proteins, peptides, polynucleotides and vectors comprising the polynucleotides of the present invention may be used as immunogens in vaccines against *H. ducreyi*, which vaccines are an aspect of the present invention. When used as an immunogen, it is not necessary to use the entire DsrA protein, although the entire DsrA protein may be used. Polypeptides, fragments, and/or antigenic determinants of DsrA may also be used as immunogens in the practice of the invention. The vaccines are used to prevent or reduce susceptibility to *H. ducreyi* infection.

The vaccines comprise an immunologically effective amount of the immunogen in a pharmaceutically acceptable carrier. The combined immunogen and carrier may be an aqueous solution, emulsion, or suspension. An immunologically effective amount is determinable by means known in the art without undue experimentation, given the teachings contained herein. Pharmaceutically acceptable carriers are known to those skilled in the art and include stabilizers, diluents, and buffers. Suitable stabilizers include carbohydrates, such as sorbitol, lactose, mannitol, starch, sucrose, dextran, and glucose and proteins, such as albumin or casein. Suitable diluents include saline, Hanks Balanced Salts, and Ringers solution. Suitable buffers include an alkali metal phosphate, an alkali metal carbonate, or an alkaline earth metal carbonate.

The immunogens of the invention are immunogenic without adjuvant, however adjuvants may increase immunoprotective antibody titers or cell mediated immunity response. Such adjuvants could include, but are not limited to, Freund's complete adjuvant, Freund's incomplete adjuvant, aluminum hydroxide, aluminum phosphate, aluminum oxide or a composition that consists of a mineral oil, such as Marcol 52, or a vegetable oil and one or more emulsifying agents, dimethyldioctadecyl-ammonium bromide, ADJU-VAX (Alpha-Beta Technology), Inject Alum (Pierce), Monophosphoryl Lipid A (Ribi Immunochem Research), MPL+TDM (Ribi Immunochem Research), TITERMAX (CytRx), toxins, toxoids, glycoproteins, lipids, glycolipids, bacterial cell walls, subunits (bacterial or viral), carbohydrate moieties (mono-, di-, tri- tetra-, oligo- and polysaccharide) various liposome formulations or saponins. Other adjuvants that may be included in vaccine compositions of the present invention include, but are not limited to: surface active substances (e.g., hexadecylamine, octadecylamine, octadecyl amino acid esters, lysolecithin, dimethyl-dioctadecylammonium bromide), methoxyhexadecylgylcerol, pluronic polyols; polyamines (e.g., pyran, dextransulfate, poly IC, CARBOPOL); and peptides (e.g., muramyl dipeptide, dimethylglycine, tuftsin). The immunogen may also be incorporated into liposomes, or conjugated to polysaccharides and/or other polymers for use in a vaccine formulation. Combinations of various adjuvants may be used with the conjugate to prepare the immunogen formulation. Exact formulation of the vaccine compositions will depend on the particular conjugate, the species to be immunized and the route of administration.

The vaccines of the invention are prepared by techniques known to those skilled in the art, given the teachings contained herein. Generally, the immunogens are mixed with the carrier to form a solution, suspension, or emulsion. One or more of the additives discussed above may be in the carrier or may be added subsequently. The vaccine preparations may be dessicated, for example, by freeze drying for storage purposes. If so, they may be subsequently reconstituted into liquid vaccines by the addition of an appropriate liquid carrier.

Any suitable vaccine and method of vaccination (i.e. immunization) known in the art may be employed in carrying out the present invention, as long as an active immune response against the antigen is elicited. When administered according to the present invention, the vaccine induces an active and protective immune response against unmodified cancer cells. Exemplary vaccination methods include, but are not limited to, "naked DNA" vaccines, viral and bacterial vector vaccines, liposome associated antigen vaccines, and peptide vaccines. Vaccines may be live vaccines, attenuated vaccines, killed vaccines, or subunit vaccines. Methods of vaccinating animals and humans against immunogens are well-known in the art. See, e.g., S. Crowe et al. *Infections of the Immune System, in Basic and Clinical Immunology*, 697–715 (D. P. Stites & A. I. Terr. eds., 7th ed. 1991).

The vaccines of the present invention are administered to humans or other mammals, including bovine, ovine, caprine, equine, leporine, porcine, canine, feline and avian species, with humans being particularly preferred. The vaccines may administered to human children, including children younger than 18 months of age. Preferably, the vaccines of the present invention are administered to those subjects that are at particular risk of developing *H. ducreyi* infection (i.e., subjects living in geographic locations where *H. ducreyi* is common).

The vaccines may be administered in one or more doses. The vaccines may be administered by known routes of administration for this type of vaccine, including parenteral administration, such as subcutaneous, intramuscular, or intravenous administration. Oral administration may also be used, including oral dosage forms which are enteric coated.

The schedule of administration of the vaccine may vary depending on the strain of *H. ducreyi* being used, the age and/or condition of the subject to be immunized, the particular formulation of the vaccine, and other factors known to those in the art. Subjects may receive a single dose, or may receive a booster dose or doses. Annual boosters may be used for continued protection.

The immunogens of this invention can be formulated as univalent and multivalent vaccines. The immunogens (i.e., the protein DsrA) can be mixed, conjugated or fused with other antigens, including B or T cell epitopes of other antigens. In addition to its utility as a primary immunogen. DsrA can be used as a carrier protein to confer or enhance immunogenicity of other antigens.

When a haptenic peptide of DsrA is used, (i.e., a peptide which reacts with cognate antibodies, but cannot itself elicit an immune response), it can be conjugated to an immunogenic carrier molecule. For example, an oligopeptide containing one or more epitopes of DsrA may be haptenic. Conjugation to an immunogenic carrier can render the oligopeptide immunogenic. Preferred carrier proteins for the haptenic peptides of DsrA are tetanus toxin or toxoid, diphtheria toxin or toxoid and any mutant forms of these proteins such as CRM 197. Others include exotoxin A of *Pseudomonas*, heat labile toxin of *E. coli* and rotaviral particles (including rotavirus and VP6 particles). Alternatively, a fragment or epitope of the carrier protein or other immunogenic protein can be used, or example, the hapten can be coupled to a T cell epitope of a bacterial toxin.

The peptides or proteins of this invention can be administered as multivalent subunit vaccines in combination with other antigens of *H. ducreyi*. For example, they may be administered in conjunction with oligo- or polysaccharide capsular components of *H. ducreyi* such as polyribosylribitolphosphate (PRP).

Peptides and proteins having epitopes of DsrA evoke bactericidal antibodies which may act synergistically in killing *H. ducreyi* with antibodies against other outer membrane proteins of *H. ducreyi*. Thus, in an embodiment of the invention. DsrA (or a peptide or protein having a common epitope) is administered in conjunction with other outer membrane proteins of *H. ducreyi* (or peptides or proteins having epitopes thereof) to achieve a synergistic bactericidal activity. For combined administration with epitopes of other outer membrane proteins, the DsrA peptide can be administered separately, as a mixture or as a conjugate or genetic fusion peptide or protein. The conjugates can be formed by standard techniques for coupling proteinaceous materials. Fusions can be expressed from fused gene constructs prepared by recombinant DNA techniques as described.

The immunogens of this invention can be administered as live vaccines. To this end, recombinant microorganisms are prepared that express the peptides or proteins. The vaccine recipient is inoculated with the recombinant microorganism which multiplies in the recipient, expresses the DsrA peptide or protein and evokes a immune response to *H. ducreyi*. Preferred live vaccine vectors are pox viruses such as vaccinia (Paoletti and Panicali. U.S. Pat. No. 4,603,112) and attenuated *Salmonella* strains (Stocker, U.S. Pat. No. 4,550,081).

Live vaccines are particularly advantageous because they lead to a prolonged stimulus which can confer substantially long-lasting immunity. When the immune response is protective against subsequent *H. ducreyi* infection, the live vaccine itself may be used in a preventative vaccine against *H. ducreyi*.

Multivalent live vaccines can be prepared from a single or a few recombinant microorganisms that express different epitopes of *H. ducreyi*. In addition, epitopes of other pathogenic microorganisms can be incorporated into the vaccine. For example, a vaccinia virus can be engineered to contain coding sequences for other epitopes in addition to those of *H. ducreyi*. Such a recombinant virus itself can be used as the immunogen in a multivalent vaccine. Alternatively, a mixture of vaccinia or other viruses, each expressing a different gene encoding for different epitopes of outer membrane proteins of *H. influenzae* and/or epitopes of other disease causing organisms can be formulated as a multivalent vaccine.

An inactivated virus or bacterial vaccine may be prepared. Inactivated vaccines are "dead" in the sense that their infectivity has been destroyed, usually by chemical treatment (e.g., formaldehyde treatment). Ideally, the infectivity of the virus or bacteria is destroyed without affecting the proteins which carry the immunogenicity of the vector. In order to prepare inactivated vaccines, large quantities of the recombinant vector expressing the desired epitopes are grown in culture to provide the necessary quantity of relevant antigens. A mixture of inactivated viruses or bacteria expressing different epitopes may be used for the formulation of "multivalent" vaccines. In certain instances, these "multivalent" inactivated vaccines may be preferable to live vaccine formulation because of potential difficulties arising from mutual interference of live viruses administered together. In either case, the inactivated virus or mixture of viruses should be formulated in a suitable adjuvant in order to enhance the immunological response to the antigens. Suitable adjuvants include: surface active substances, e.g., hexadecylamine, octadecyl amino acid esters, octadecylamine, lysolecithin, dimethyl-dioctadecylammonium bromide, N, N-dicoctadecyl-N'-N'bis (2-hydroxyethyl-propane diamine), methoxyhexadecylglycerol, and pluronic polyols; polyamines, e.g., pyran, dextransulfate, poly IC, CARBOPOL; peptides, e.g., muramyl dipeptide, dimethylglycine, tuftsin; oil emulsions; and mineral gels, e.g., aluminum hydroxide, aluminum phosphate, etc.

One particularly preferred embodiment of the invention is an attenuated vaccine comprising an *H. ducreyi* strain that does not express DsrA. The *H. ducreyi* strains that do not express DsrA used in these vaccines may be naturally occurring strains, or may be recombinant and/or isogenic mutants of *H. ducreyi* strains that do express the protein. Of these attenuated vaccines, a vaccine comprising the *H. ducreyi* mutant strain FX517 described herein is most preferred.

The bactericidal antibodies induced by DsrA epitopes can be used to passively immunize an individual against *H. ducreyi*. Passive immunization confers short-term protection for a recipient by the administration of the pre-formed antibody. Passive immunization can be used on an emergency basis for special risks, e.g. young children exposed to contact with subjects already afflicted with *H. ducreyi* infection (chancroid).

In view of the foregoing description, the invention also comprises a method for inducing an immune response to *H. ducreyi* in a mammal in order to protect the mammal against infection by invasive or non-invasive *H. ducreyi*. The method comprises administering an immunologically effective amount of the immunogens of the invention to the host and, preferably, administering the vaccines of the invention to the host.

The following Examples are provided to illustrate the present invention, and should not be construed as limiting thereof. Unless otherwise noted, all chemicals and reagents were from Sigma Chemicals (St. Louis. MO). Standard recombinant DNA methods were used as described in Sambrook et al. (supra) or following manufacturers instructions.

EXAMPLE 1

Materials and Methods: Bacterial Strains and Media

Bacterial strains used in the experiments described herein are shown below in Table 1. For routine growth. *H. ducreyi* was maintained on chocolate agar plates obtained from UNC Hospital Clinical Microbiology Lab. This medium was prepared using Mueller Hinton base and contained no fetal calf serum. When 5% fetal calf serum was required for optimal growth (*H. ducreyi* strains CHIA and 1157), Gonococcal medium base (GCB) was used for preparation and instructions were followed (Difco). Antibiotics were used at the following concentrations for *E. coli*: ampicillin, 100 µg/ml; chloramphenicol, 30 µg/ml; kanamycin, 30 µg/ml; and streptomycin, 100 µg/ml. For *H. ducreyi*, antibiotics were chloramphenicol, 1 µg/ml or streptomycin, 100 µg/ml.

TABLE I

Bacterial strains and plasmids

| Strain/Plasmid | Relevant Genotype/Phenotype | Source/Reference/Isolated |
|---|---|---|
| *E. coli* K-12 | | |
| DH5αLMCR | recA, gyrB | Bethesda Research Labs |
| *H. ducreyi* | | |
| 35000 | wild type | Stanley Spinola Indiana Univ. |
| FX516 | 35000 Co-integrate beta galactosidase positive intermediate in FX517 construction, Cm$^r$ | This work |
| FX517 | 35000 dsrA, Cm$^r$ | This work |
| CIP542 (Canada) | | William Albritton |
| CIP A77 | | Robert Munson |
| CIP 542 (CDC) | | Stephen Morse Centers for Disease Control |
| *H. ducreyi* obtained from Pat Totten | (10) | |
| CIP A75 | | Pasteur Institute |
| CHIA | | VDRL |
| HD167 | | VDRL |
| V-1157 | | Seattle |
| V-1168 | | Seattle |
| M90-02 | | Bahamas |
| 406 | | Mississippi |
| 425 | | Mississippi |
| 54 | | Mississippi |
| 010-2 | | Dominican Republic |
| HD301 | | Thailand |
| HD350 | | Kenya |
| Plasmids | | |
| pCRII | PCR cloning vector Kan$^r$, Amp$^r$ | Invitrogen |
| pUNCH 1248 | dsrA PCR clone using primers 14 and 16 in pCRII vector | This work |
| pLS88 | Shuttle plasmid Kan$^r$, Str$^r$, Sul$^r$ | (9) |
| pUNCH 1254 | dsrA subclone. ECoR1 fragment of pUNCH 1248 in EcoR1 of pLS88 | This work |
| pUNCH 1255 | mutagenized dsrA; pUNCH 1254 mutagenized with CAT cassette from pNC40 Kan$^r$, Cm$^r$ | This work |
| pRSM1791 | Mutagenesis plasmid Beta gal$^r$, Amp$^r$ | (6) |
| pUNCH 1256 | pUNCH 1255 (SmaI/HinClI/Klenow) into the NotI (Klenow) of pRSM1791 | This work |
| pUNCH 1260 | dsrA PCR clone using primers 14 and 16 in pLSKS | This work |
| pNC40 | source of CAT cassette, Amp$^r$, Cm$^r$ | (37) |

EXAMPLE 2

Outer Membrane Isolation, Analysis, SDS-PAGE and Immunoblotting

Large scale cultures of *H. ducreyi* were performed in Fernbach flasks with 1 liter of GCB-1 broth containing 5% fetal calf serum and 50 µg/ml heme (Elkins, C. *Identification and purification of a conserved heme-regulated hemoglobin-binding outer membrane protein from Haemophilus ducreyi*.

Infec Immun. 63, 1241–1245 (1995)). Cultures of *E. coli* were performed in LB broth or LB agar plates containing appropriate antibiotics. Outer membranes were harvested as previously described Id. Protein concentrations were determined using the BCA kit from Pierce (Rockford, Ill.). SDS-PAGE, and Western blotting were performed as previously described (11). The lipooligosaccharide (LOS) of *H. ducreyi* was prepared using the method of Hitchcock and Brown (Hitchcock, P. G., and Brown, T. M. *Morphological heterogeneity among Salmonella LPS chemotypes, in silver-stained polyacrylamide gels. J. Bacteriol.* 154, 269–277 (1983). LOS was analyzed by SDS-PAGE and silver staining (Tsai, C. M. and Frasch, C. E., *A sensitive silver stain for detecting lipopolysaccharides in polyacrylamide gels. Anal. Biochem.* 155, 115–119 (1982)) or Western blotting with Mab 3F11 (Apicella, M. A. et al., *Phenotypic variation in epitope expression of the Neisseria gonorrhoeae lipooligosaccharide. Infect Immun.* 55:1755–1761 (1987).

EXAMPLE 3

N-Terminal Sequence Amino Acid (AA) Determination

The N-terminal aa sequence of DsrA was determined from strain 35000. Outer membranes were subjected to preparative SDS-PAGE and Western transfer to PVDF. The blot was stained temporarily with Ponceau S protein stain to locate the DsrA protein, which in strain 35000 migrates just below the 30 kDa standard protein. Strips of the blot were probed with anti-OpaF (generously provided by Janice Babcock and Richard Rest of Hahnemann Medical College) of gonococcal strain FA1090 and Mab 5C9. Anti-OpaF, for unknown reasons, cross-reacts with DsrA and Mab 5C9 reacts with a previously described *H. ducreyi* lipoprotein (termed Hlp) of similar molecular weight (18). These antibodies were used in order to unequivocally identify the proper band to sequence. The corresponding 30 kDa-OpaF reactive band from the remainder of the Ponceau S stained blot was sequenced. The sequence obtained from the 30 kDa band was QQPPKFAGVS SLYSYEYDYG KGKKTK-SNEG (amino acid residues 22–51, SEQ ID NO:2). This sequence did not match the processed mature, N-terminal sequence of Opa or Hlp 28 kDa (Hlp would be expected not to sequence, since it is a lipoprotein). We concluded that these three proteins were distinct.

The antiserum to DsrA was produced as follows. Outer membranes from *H. ducreyi* strain 35000 were electophoresed on large preparative well 12% SDS-PAGE gels. The gel was briefly stained and the corresponding 30 kDa band excised and electroeluted using a CENTRILUTOR (Amicon) following the manufacturer's instructions. Mice were immunized a total of 3 times with 25 µg of gel purified protein per immunization. Freund's complete adjuvant was used for the first immunization and incomplete for the remainder.

EXAMPLE 4

Vector-Anchored PCR

Figure 2:
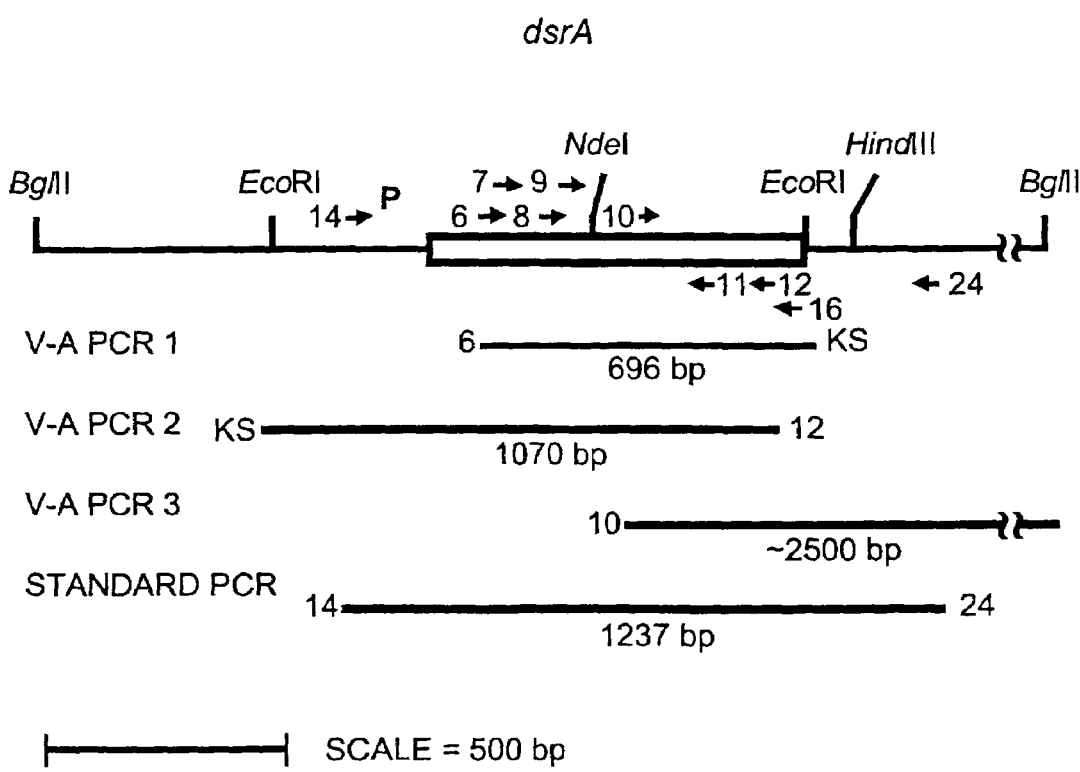
FIG. 2 is a schematic illustration of the restriction map of the dsrA region and PCR products thereof. The dsrA open reading frame is boxed. The restriction sites are indicated. The numbered arrows indicate direction and position of the dsrA oligos used for PCR. The letter KS and T7 (promoter) refer to the vector primers used in the vector-anchored PCR reactions. V-A PCR refers to vector-anchored PCR; P refers to a promoter. The jagged lines represent approximately 2 kb of sequence not shown downstream of the dsrA locus.
Figure 5:
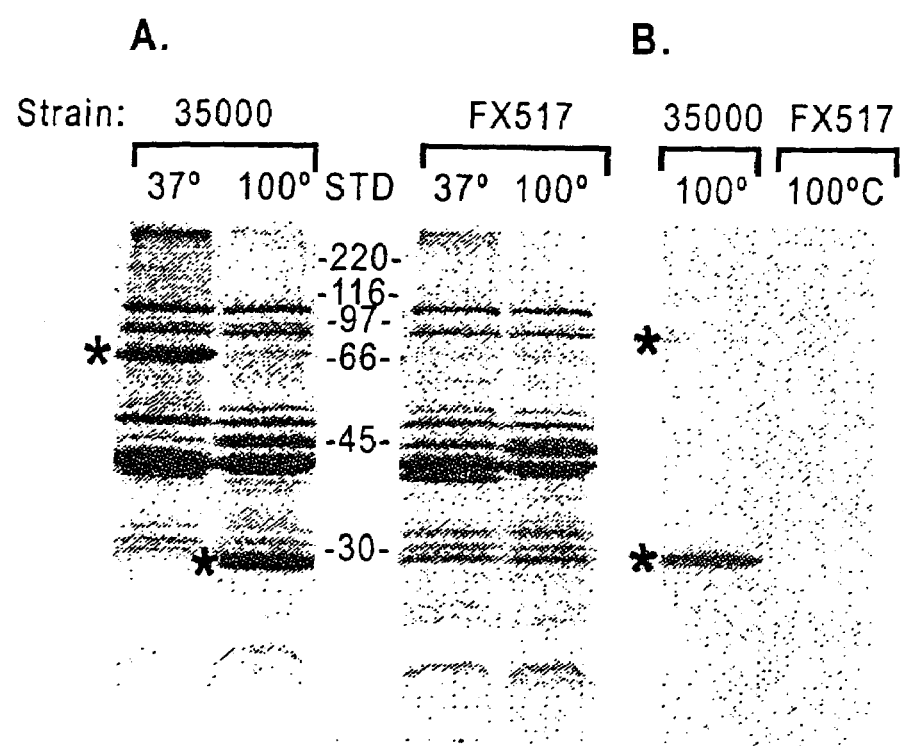
FIGS. 5A and 5B show a SDS-PAGE/Western blot of parent strain 35000 and dsrA mutant FX517. Outer membranes were prepared, solubilized at 37° C. or 100° C. and subjected to SDS-PAGE and Coomassie staining (Panel A). For the Western blot (panel B), outer membranes were solubilized at 100° C., transferred to nitrocellulose and probed with anti-DsrA mouse serum. Bound antibody was detected with alkaline phosphatase-conjugated secondary antibody and BCIP/NBT substrate. The asterices indicate the positions of the DsrA protein. STD, molecular weight standards.
Figure 6:
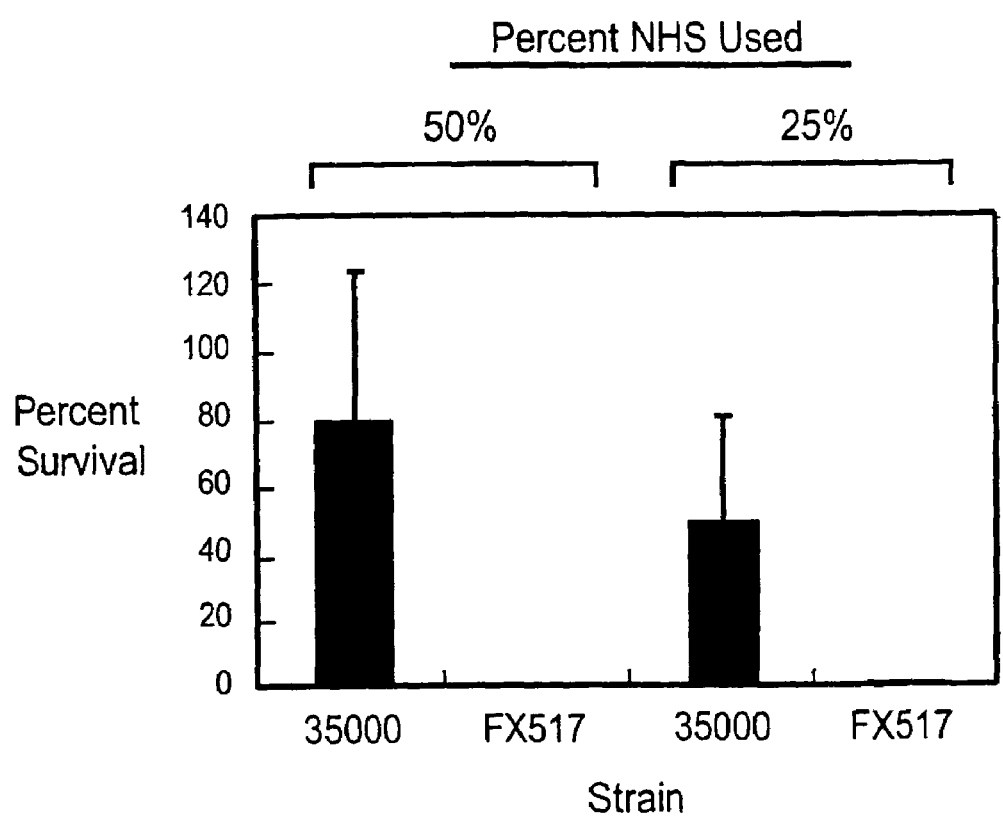
FIG. 6 is a graphical illustration of the bactericidal killing of parent strain 35000 compared with the bactericidal killing of the dsrA mutant FX517. Bactericidal killing was performed as described in FIG. 1, except that two serum concentrations were utilized. The data presented in FIGS. 1 and 6 for 35000 with 50% sera are the same data. The data presented for 35000 were obtained in parallel experiments with FX517.
Figure 7:
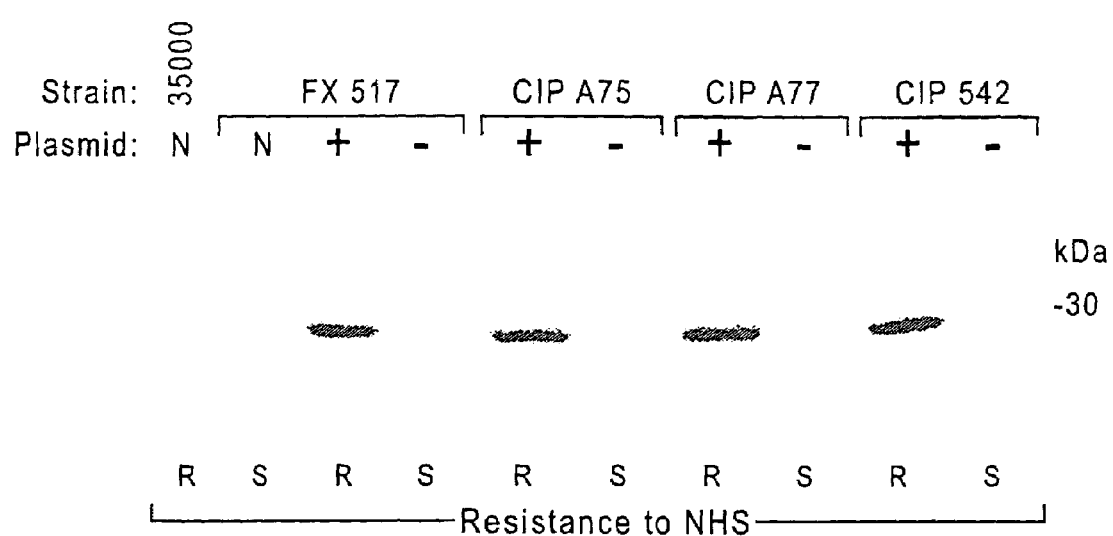
FIG. 7 is a photograph of a SDS-PAGE/Western Blot illustrating Complementation of dsrA mutants. Total cellular proteins from the indicated *H. ducreyi* strains were subjected to SDS-PAGE (12%) and Western blotting using anti-DsrA antisera. Bound antibody was detected with horseradish peroxidase-conjugated secondary antibody followed by chemiluminescence. "N" indicates no plasmid present; "+" indicates pUNCH 1260 (i.e., contains the entire dyrA ORF from strain 35000 and its putative native promoter as illustrated in FIG. 2); "−" indicates pLSKS a vector without insert. Below each strain are shown the summary of bactericidal killing of the complemented dsrA mutants. Bactericidal killing was performed as in FIG. 1 (50% serum), except that the medium used contained streptomycin.

Two degenerate oligonucleotides deduced from the N-terminal amino acid sequence (#6 and #7, FIG. 2) specifically hybridized to a 1.1 kb EcoR1 genomic fragment (data not shown). Attempts to clone this fragment using size selected DNA using several plasmid vectors were unsuccessful. Therefore a series of three separate vector-anchored PCR strategies were utilized to clone the dsrA structural gene, upstream flanking DNA and downstream flanking DNA, respectively. The first vector-anchored PCR (FIG. 2, V-A PCR 1) used the ligation between the 1.1 kb EcoR1 size-selected DNA and vector pBluescript as template and used 5' primer #6 and vector primer KS as amplimers. An approximate 700 bp fragment was amplified and preliminary sequence obtained. The N-terminal sequence originally obtained from Edman degradation matched the deduced amino acid sequence of the PCR product, but was not homologous to known sequences in the data bases. In contrast, the C-terminus of the gene was homologous to UspA2 and YadA (see results below), this suggested the possibility of PCR generated artifact(s). To rule out PCR artifact additional PCR was performed. The primers used included 5' primers #6, 8 and 9 and 3' primers 11 and 12. The latter 4 primers were derived from the DNA sequence obtained from the original anchored PCR product above (FIG. 2 and data not shown). Identically sized products from total *H. ducreyi* chromosomal DNA template (and the original anchored PCR product, the +control template were amplified) using 3' primers from the region with homology to C-terminal YadA (primers #11 and #12) (data not shown). Furthermore, Southern hybridization of *H. ducreyi* chromosomal DNA probed with oligos #6, #7, #8, #9, #11, #12 and the PCR product generated from #8 and #12 all specifically recognized the 1.1 kb band ECoR1 band (FIG. 1 and data not shown). It was concluded that the N-terminal aa sequence obtained from the 30 kDa protein is found on the same ORF that has C-terminal homology to UspA2/YadA. These data established that the open reading frame (ORF) data were correct.

To obtain sequence upstream of the structural gene for dsrA, a second vector-anchored PCR was used (FIG. 2, V-A PCR 2). Again, the template was the ligation between the 1.1 kb EcoR1 size-selected DNA and vector pBluescript but the primers used were #12 and vector primer KS. A (1069) bp fragment which included the upstream EcoR1 site (FIG. 2.) was amplified.

To obtain sequence downstream of the dsrA gene, a third vector-anchored PCR was used (FIG. 2, V-A PCR 3). Southern hybridization identified an approximately 4 kb Bgl II fragment which hybridized with dsrA probes and there are no Bgl II sites in the 1.1 kb EcoR1 fragment. Fragments of 3–5 kb Bgl II restricted chromosomal DNA were isolated and ligated to BamH1, shrimp alkaline phosphatase treated pMCL210 vector. The ligation reaction was ethanol precipitated and amplified using primers 10 and vector primer T7 (promoter), yielding an approximately 2.5 kb PCR product. The products of all three vector-anchored PCR reactions were sequenced with appropriate primers to obtain preliminary sequence and these sequences confirmed one another (data not shown).

Commercially available PCR tubes (Ready to Go, Pharmacia) were utilized for PCR. Analytical PCR (25 ul final volume) utilized single tubes whereas preparative PCR combined the "beads" from 4 tubes into single tube (100 ul final volume). The $MgCl_2$ concentration in all PCR reactions was 4 mM. The first two vector anchored PCRs used 5 ul of ligation and 25 pm of each primer. The conditions for PCR for first two vector anchored PCRs were: hot start 5 min 94C, denature 94C; 1 minute annealing, 50C, 1 minute; extension 72, 1 minute. The conditions for the third PCR were identical except that the extension time was 3 min.

EXAMPLE 5

DNA Sequencing and Analysis

Figure 9:
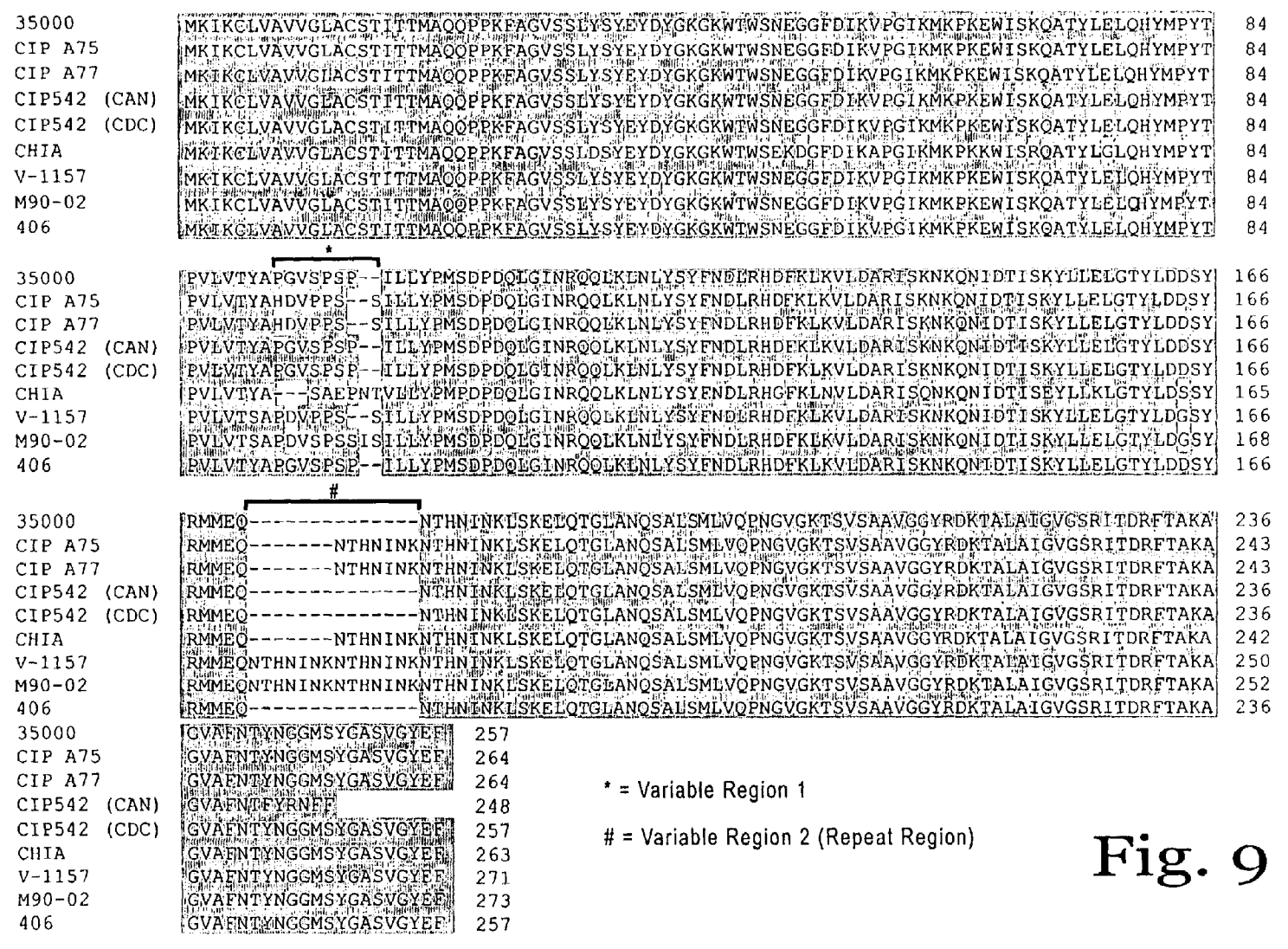

DNA sequence analysis was performed at the University of North Carolina at Chapel Hill Automated Sequencing Facility utilizing Taq terminator chemistry. The final sequences presented for strain 35000 in FIG. 2 and for the other *H. ducreyi* strains in FIG. 9 was obtained from PCR products using primers #14 and 24 which flank the dsrA gene (FIG. 1). Both strands of the were completely sequenced. The sequence data were assembled using the program AssemblyLIGN (IBI). The preliminary sequence for the dsrA structural gene from 35000 obtained by vector-anchored PCR was in complete agreement with the final sequence presented (FIG. 3). Amino acid alignments were done by Clustal in the program GeneJockeyII (Cambridge, UK) and PAM 250 setting. Bestfit (GCC Computer Group, Wisconsin) was used to generate similarity and identity scores using a gap weight of 8.

EXAMPLE 6

Plasmid Constructions

Plasmid pUNCH 1248 was constructed by PCR. A 900 bp fragment was amplified from *H. ducreyi* strain 35000 using primers 14 and 16 (FIG. 2), using the conditions described above for the first two vector anchored PCRs. The product was ligated to pCRII following the manufacturer's directions, transformed into *E. coli* DH5a and recombinants identified by restriction analysis. *E. coli* harboring pUNCH 1248 grew poorly, was propagated only on agar plates to reduce the possibility of mutation/deletion, and gave rise to an occasional larger colony. Subclone 1254 was constructed by isolating the EcoR1 fragment of pUNCH 1248 and ligation into EcoR1 restricted pLS88. dsrA of pUNCH 1254 was mutagenized by insertion of a CAT (Chloramphenicol Acetyl Transferase) into the open reading frame to construct pUNCH 1255. To perform this, a CAT cassette (a BglII fragment from pNC40 was treated with Klenow to fill-in the ends) was ligated into the NdeI site of pUNCH 1254 (previously treated with Klenow to produce blunt ends), pUNCH 1256 was constructed by moving the insert from pUNCH 1255 (containing mutagenized dsrA) into plasmid pRSM1791 for subsequent mutagenesis. This was done by isolation of a SmaI to HinCII fragment of pUNCH 1255, Klenow treatment and ligation into the NotI site of pRSM1791 previously treated with Klenow. Transformation of an *E. coli* host was performed and selection using Amp and Cm yielded pUNCH 1256.

EXAMPLE 7

Construction and Characterization of an *H. ducreyi* DsrA Mutant

An isogenic mutant (FX517, Table 1) was constructed by allelic replacement of the wild-type locus of strain 35000 with the mutation in pUNCH 1256 using a previous system of mutagenesis described by Bozue et al (Bozue, J. A. et al.; *Facile construction of mutations in Haemophilus ducreyi using lacZ as a counter-selectable marker. FEMS Microbiology Letters*. 164, 269–73 (1998)). In this procedure, a mutagenized copy of the locus (containing a chloramphenicol (Cm or CAT) cassette) was subcloned into a plasmid able to express lacZ (pUNCH 1256). *H. ducreyi* were electroporated and $Cm^r$ transformants selected (Elkins et al., *Characterization of the hgbA locus of Haemophilus ducreyi Infect Immun.* 63, 2194–2200 (1995); Hansen, E. J. et al., *Use of electroporation to construct isogenic mutants of Haemophilus ducreyi. J. Bacteriol.* 174, 5442–9 (199)). These transformants putatively contained the entire plasmid integrated due to a single crossover event (as exemplified by FX516, Table 1). Individual transformants were streaked onto Cm medium containing X-gal. Since the product of X-gal is highly toxic to *H. ducreyi* the co-integrates grow as tiny blue colonies. The loss of the X-gal sequences and neighboring wild type allele via a resolution of the co-integrate results in only the mutant allele being retained (exemplified by FX 517, Table 1). These *H. ducreyi* mutants grew as normal-sized white colonies on the medium containing Cm and X-gal similar to other *H. ducreyi* mutants containing CAT cassettes (Elkins, C. et al., *Characterization of the hgba locus of Haemophilus ducreyi. Infect Immun.* 63, 2194–2200 (1995) Elkins, C. et al., *Role of the Haemophilus ducreyi Ton system in internalization of heme from hemoglobin. Infection & Immunity* 66,151–60 (1998); Thomas, C. et al., *Cloning and characterization of tdhA, a locus encoding a TonB-dependent heme receptor from Haemophilus ducreyi. Infect Immun.* 66, 1–9 (1998)) and data not shown.

Southern blot and PCR analysis was used to confirm that an allelic replacement occurred in the generation of *H. ducreyi mutant FX*517. Chromosomal DNA was isolated from strains 35000. FX516, and FX517, digested with HinCII and subjected to electrophoresis and bidirectional transfer. The two blots were probed with either the PCR product of oligos 14 and 16 or the Bgl II CAT fragment from pUNCH 40. Digoxigenin-labeled, bound probe was detected with alkaline phosphatase labeled anti-digoxigenin antibody (Boehringer Mannheim) followed by detection with nitroblue tetrazolium and 5-bromo-4-chloro-3-indolyl phosphate (NBT/BCIP). PCR confirmation of the mutant utilized primers 14 and 16 which flank the NdeI site (CAT cassette) used for gene disruption.

EXAMPLE 8

Complementation of FX517 and Other DsrA Mutants in Trans

To rule out that the serum susceptibility of dsrA mutant FX517 was due to a mutation elsewhere on the chromosome or polar downstream effects, complementation in trans was performed. Briefly, we PCR amplified the dsrA and surrounding locus, using primers 14 and 24 (FIG. 2), Klenow treated the PCR product, and restricted the PCR product with HinDIII (which restricts just downstream of dsrA, FIG. 2). After gel purification, the PCR product was ligated into SmaI/HinDIII restricted pLSKS (Wood, G. E. et al., *Target and cell range of the Haemophilus ducreyi hemolysin and its involvement in invasion of human epithelial cells. Infect and Immun*. In Press.) The ligation was ethanol precipitated and *H. ducreyi* strain FX517 electroporated. Streptomycin resistant colonies were screened for production of DsrA by Western blotting and confirmed by restriction analysis. One experimental transformant, pUNCH 1260dsrA, and one vector transformant were selected for further study, pUNCH 1260 and the vector pLSKS (negative control) were then electroporated into the three naturally occurring dsrA mutants (CIP A75, CIP A77, CIP 542 (Can), Table 1).

EXAMPLE 9

Serum Susceptibility

The resistance of H. ducreyi to normal human serum was performed as previously described (Odumeru; Carbonetti) with the following modifications: An 18–24 hour culture of H. ducreyi from chocolate agar plates was scraped into GCB broth to an OD600 of 0.2. A $10^{-4}$ to $10^{-5}$ dilution was made (approximately 1000 CFU/ml, depending on the strain) and mixed with pooled fresh normal human serum (NHS) or heat inactivated NHS (56° C., 30 min) to a final concentration of 25 or 50% NHS. After incubation for 45 minutes at 35° C. in 5% $CO_2$, 100 μl aliquots were plated onto chocolate agar plates and viable counts performed after 48 hours. Data are expressed as percent survival in the fresh NHS as compared to survival in heat-inactivated NHS (number of CFU survivors in fHNS/number of survivors in heated NHS X 100). Strains containing pUNCH 1260 or PLSKS were propagated and plated on chocolate agar containing streptomycin at 100 μg/ml.

EXAMPLE 10

Identification of a 30 kDa Protein Involved in Serum Resistance

During the course of studies characterizing the H. ducreyi interaction with PMNs, a series of Western blots was performed using various antibodies to the Opa proteins from gonococci. It was found that a polyclonal antiserum to OpaF of gonococcal strain FA1090 reacted at a dilution of 1:5000 with a protein (DsrA) that varied between 28 and 35 kDa in a panel of strains (data not shown). One strain, CIPA75, did not react. CIPA75 was of interest because it had previously been shown to be avirulent in the chilled rabbit model of infection, to be serum susceptible, to exhibit reduced adherence to HEp-2 cells and to have a truncated LOS (Odumeru, J. A. et al, *Role of lipopolysaccharide and complement in susceptibility of Haemophilus ducreyi to human serum. Infect Immun.* 50,495–9 (1985); Rice, P. A., *Molecular basis for serum resistance in Neisseria gonorrhoeae. Clinical Microbiology Reviews.* 2, S112–7 (1989). Specific antisera to DsrA were generated using DsrA purified by preparative SDS-PAGE and electroelution of outer membranes from H. ducreyi strain 35000. Western blots of several geographically diverse lab and clinical isolates were probed with anti-DsrA (FIG. 1). This was done to confirm that the previous cross-reactivity seen with the anti-OpaF serum was due to the presence of DsrA and to ascertain what percentage of strains expressed dsrA. The proteins recognized in the DsrA Western blot (FIG. 1) and the OpaF Western blot (data not shown) appeared to be identical. Most strains in FIG. 1 expressed an immunoreactive protein, except for the previously reported avirulent strains CIP A75, CIP A77 (25–27) and CIP542 (Can., obtained from Canada) (Alfa, M. J. et al., *Use of tissue culture and animal models to identify virulence-associated traits of Haemophilus ducreyi. Infection & Immunity* 63:1754–61 (1995)). In contrast virulent CIP 542 (CDC), obtained from the CDC and previously shown to cause a laboratory acquired infection (Trees, D. L. et al., Laboratory-acquired infection with *Haemophilus ducreyi* type strain CIP 542. *Med Microbiol* 330–337 (1992)), expressed dsrA. Previous studies documented that virulent H. ducreyi strains are serum resistant. We performed serum susceptibility studies of selected H. ducreyi strains which did and did not express dsrA and these results are summarized at the bottom of FIG. 1. For the purposes of this study, we arbitrarily termed a strain serum resistant if there were more than 10% survivors when exposed to 50% fNHS serum as compared to NHS. The specific percent survivors (+/–sd) for each of the strains tested in FIG. 1 are: 35000, 79%; CIP A75; CIP A77; CIP 542 (Can); CIP 542 (CDC); CHIA; V-1157; M90-02; and 406. Thus, in these initial studies there was a correlation between strains tested which expressed detectable dsrA and serum resistance. This correlation between the lack of expression of dsrA and serum susceptibility in the dsrA mutant strains, some of which also had LOS alterations, could merely be coincidental. Therefore additional molecular studies were performed, culminating in the generation of an isogenic dsrA mutant for biological studies.

EXAMPLE 11

Molecular Studies

Through a series of experiments involving Western blotting, immunoprecipitation and finally N-terminal amino acid sequencing, it was determined that the DsrA protein was not the same as the previously described 28 kDa lipoprotein termed Hlp (17) (data not shown). The N-terminal amino acid sequence of the immunoreactive DsrA 30 kDa protein of strain 35000 was found to be: QQPPKFAGVS SLYSYEYDYG KGKKTKSNEG (amino acid residues 22–51, SEQ ID NO:2). No known homologies were initially detected when this peptide sequence was searched against GENBANK, including gonococcal Opa proteins.

Two degenerate oligonucleotides (#6 and #7) were synthesized based on the above N-terminal sequence and found to hybridize specifically to a 1.1 kB EcoR1 chromosomal band from *H. ducreyi* strain 35000 (data not shown). Attempts to clone this fragment were unsuccessful and three separate vector-anchored PCR reactions (V-A PCR) were used to amplify the relevant locus and surrounding regions (FIG. 2). Preliminary sequencing of the product of V-A PCR 1 (FIG. 2) identified an ORF that was homologous to the UspA2 protein of *Moraxella catarrhalis* and the YadA protein of *Yersinia* spp., but only in the C-terminal region. Since both of these proteins are implicated in determining important virulence traits (including serum resistance), additional studies were undertaken.

EXAMPLE 12

DNA and Deduced Amino Acid Sequence of the *H. ducreyi* dsrA Locus from Strain 35000

The DNA sequence of the dsrA locus, including 100 bp of sequence upstream of the ATG start and 126 bp of sequence downstream of the TAA termination codon are presented in FIG. 3. The data presented were obtained from PCR products amplified using primers 14 and 24. Sequences similar to −35 (TGATAA) and −10 (TATATT) *E. coli* promoter consensus sequences were found beginning at nt 13 (TTGACA) and nt 35 (TAGAAT) respectively, and were separated by 16 nt. A putative ribosome-binding site (TAATGAGG) was found beginning 13 nt upstream of the dsrA start codon. Beginning at nt 913 and ending at nt 946 was an inverted hairpin loop containing 13 matched nucleotides, consistent with a transcription terminator. The gene immediately downstream of dsrA and in the opposite orientation was an ORF with homology to the hypothetical protein HI0107 of the genome sequence of *H. ducreyi*. The GC content of the 1 kb of DNA sequence presented was 34.5%, consistent with the AT-rich nature of *Haemophilus* spp. DNA.

The dsrA ORF predicted a protein of 28215 daltons, which when processed would yield a mature protein of 26375 daltons. This is in agreement with migration in SDS-PAGE for strain 35000 (FIG. 1). Comparison of the deduced amino acid sequence of DsrA with the N-terminal amino acid sequence revealed identity in 28 of 30 amino acids. The first two residues of the mature protein, QQ, were unusual in their charges; however, certain versions of mature YadA begin with two charged amino acids (see below). Just preceding the DsrA QQ residues was the unusual signal peptidase I cleave site of TMA. Consistent with the outer membrane localization, DsrA contained a carboxyl terminal motif ending with a phenylalanine which is found in the majority of integral outer membrane proteins (Struyve, M. et al., *Carboxyl-terminal phenylalanine is essential for the correct assembly of a bacterial outer membrane protein. J. Mol. Biol*, 218, 141–148 (1991)). The mature DsrA protein was predicted to be very basic, with a pl of 9.1 and which accounts for its poor transfer during Western blotting (data not shown).

Alignment of the DsrA protein with similar proteins is shown in FIG. 4. DsrA was most similar to UspA2 and YadA in a region of the C-terminus and was most divergent in the N-terminus. Using the Bestfit program, DsrA was 45% similar and 40% identical to UspA2; DsrA was 47% similar and 39% identical to YadA. It should be noted that both of these heterologous proteins are considerable larger than DsrA which may account for such differences in the N-terminal domains. The C-terminus of YadA is believed to be anchored in the outer membrane and the N-terminus encodes the functional regions of the YadA protein (Rogenkamp, A. et al., *Substitution of two histidine residues in YadA protein of Yersinia enterocolitica abrogates collagen binding, cell adherence and mouse virulence. Molecular Microbiology* 16, 1207–19 (1995); Roggenkamp, A. et al., *Deletion of amino acids 29 to 81 in adhesion protein YadA of Yersinia enterocolitica serotype 0.8 results in selective abrogation of adherence to neutrophils. Injection & Immunity* 65, 2506–14 (1996); Tamm, A., et al., *Hydrophobic domains affect the collagen-binding specificity, and surface polymerization as well as the virulence potential of the YadA protein of Yersinia enterocolitica. Molecular Microbiology.* 10, 995–1011 (1993)).

EXAMPLE 13

Construction and Characterization of an *H. Ducreyi* DsrA Mutant.

Figure 8:
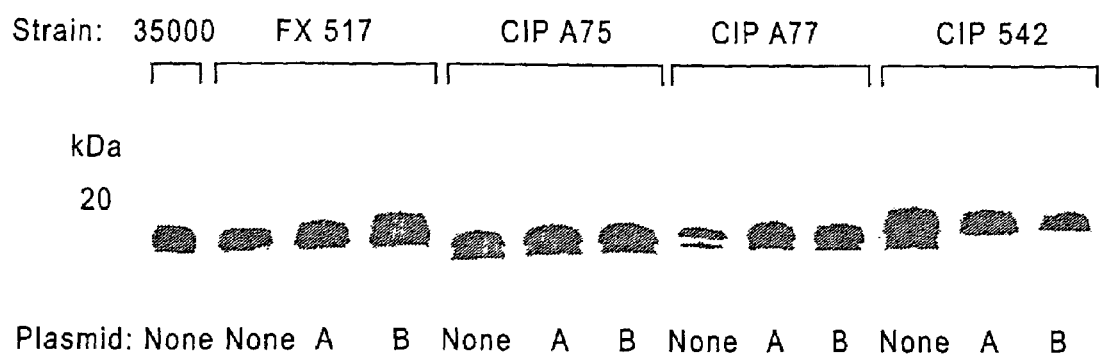
FIG. 8 is a photograph of an SDS-PAGE gel illustrating the analysis of LOS as described in Example 16, below. Crude LOS was prepared as described in the text and subjected to SDS-PAGE and silver staining.
Figure 11:
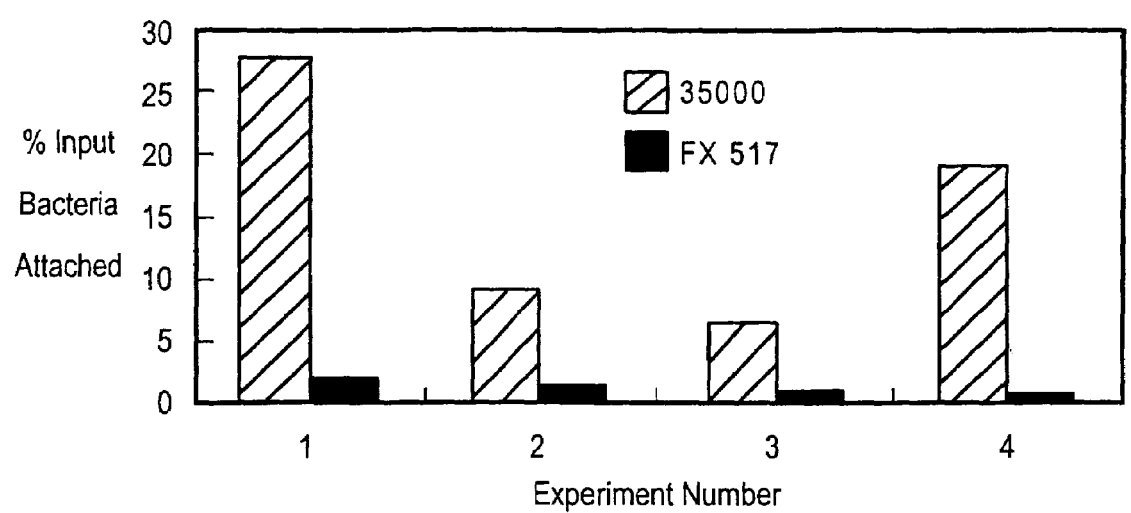
FIG. 11 is a graphical illustration showing that efficient attachment of *H. ducreyi* to a keratinocyte cell line requires DsrA expression. *H. ducreyi* were added to HaCaT cells at a MOI of between 1–5:1 and incubated for two hours. After removal of unbound bacteria by extensive washing, CFUs were determined by plating the disrupted monolayer. The data shown in FIG. 11 are taken from four experiments.
Figure 12:
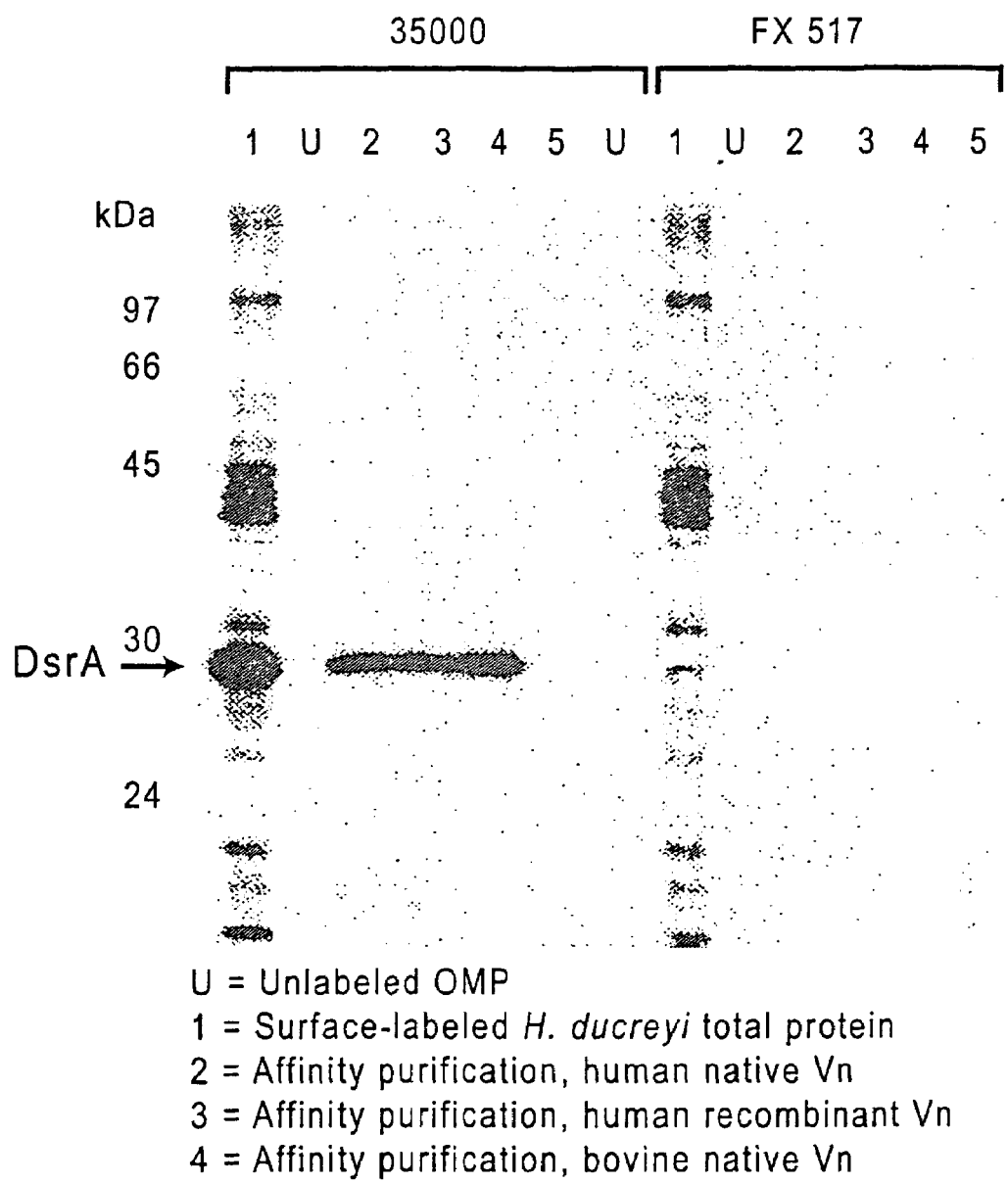
FIG. 12 is an autoradiograph of an SDS-PAGE illustrating the affinity purification of DsrA from whole cells using biotinylated vitronectins (Vn). Biotinylated vitronectins were mixed with surface-iodinated *H. ducreyi* and allowed to bind. After washing unbound vitronectin by centrifugation and washing, *H. ducreyi* were solubilized with a gentle detergent. Total soluble *H. ducreyi* proteins were bound to solid-phase streptavidin-agarose. After washing the streptavidin agarose, bound proteins were eluted by boiling in sample buffer and analysis by SDS-PAGE and autoradiography.

An isogenic mutant (FX517, Table 1) was constructed by allelic replacement of the wild-type locus of strain 35000. Initial attempts to obtain a double crossover with a CAT cassette in the cloned gene were unsuccessful using pUNCH 1255 (data not shown). Therefore, we used a recently described method to obtain mutants (Bozue, J. A. et al., *Facile construction of mutations in Haemophilus ducreyi using lacZ as a counter-selectable marker. FEMS Microbiology Letters.* 164:269–73 (1998)). Using this procedure, several chloramphenicol resistant cointegrates were obtained. After streaking each cointegrate onto X-gal chocolate plates, several mutants were obtained for each cointegrate and none of mutants expressed dsrA (data not shown). One mutant, FX517 was selected for further study. Outer membranes were made from the parent and mutant strain FX517 and subjected to SDS-PAGE and Coomassie staining or SDS-PAGE and Western blotting (FIGS. 5A and 5B, respectively). DsrA is an abundant outer membrane protein in strain 3500 but is absent in the mutant. No reactivity was obtained from FX514 using anti-DsrA antisera (FIG. 5, Panel B) or anti-OpaF (data not shown). Similar to UspA2 and YadA, DsrA had a propensity to form multimers, especially when solubilized at the lower temperature of 37C (FIG. 5. Panel A, and data not shown).

The structure of the mutagenized dyrA locus in FX517 was confirmed using Southern blotting and PCR. In Southern blots of chromosomal DNA from the parent and mutant strains the HinCII band recognized by the dsrA probe increased in size approximately 1 kb in the mutant as compared to the parent band. Similarly, an identical blot hybridized with the CAT probe recognized only the larger HinCII band of the mutant (data not shown). PCR, of the 35000 and FX517 dsrA locus with primers flanking the CAT insertion indicated the locus was approximately 1 kb larger in the mutant (data not shown). These data are consistent with an allelic replacement event.

EXAMPLE 14

Serum Resistance Phenotype of the DsrA Mutant

The serum susceptibility of the naturally occurring dsrA mutants and the role of the related YadA and UspA2 proteins in mediating serum resistance prompted us to test FX517 for serum sensitivity. Serum killing studies of parent strain 35000 and dsrA mutant FX517 were performed using 25 and 50% normal pooled serum (FIG. 6). FX517 was very susceptible to NHS and demonstrated zero or 2% survival in 50% and 25% NHS, respectively. In contrast, parent strain 35000 was relatively serum resistant, exhibiting 79% and 50% survival in 50% and 25% NHS (p values 0.002 and 0.004 for 50% and 25% NHS, respectively, using Students paired T test). Thus DsrA appeared to be required for expression of a serum resistant phenotype.

EXAMPLE 15

Complementation of DsrA Mutants

It was possible that a cryptic mutation had occurred during the construction of FX517 which could account for its serum susceptibility phenotype. Furthermore, we wished to determine whether the serum susceptibility of the three naturally occurring dsrA mutants could be converted to serum resistance if they expressed dsrA. Each dsrA mutant (isogenic mutant FX517 or naturally occurring mutants CIP A75, CIP A77, and CIP 542 (Can)) was electroporated with pUNCH 1260 (dsrA) or pLSKS (vector control) plasmids. These shuttle plasmids are able to replicate in *H. ducreyi*. Strains containing pUNCH 1260, but not pLSKS, expressed dsrA (FIG. 7A). Subjectively, it appeared that more DsrA was expressed from the strains complemented with the dsrA plasmid than from 35000 (n=4), perhaps due to gene dosage or growth on medium containing streptomycin. Expression of dsrA from plasmid pUNCH 1260 suggested that the tentatively identified promoter (FIG. 3), was driving expression of the cloned dsrA gene since very little additional upstream DNA was present and the insert was in the opposite direction of the lac promoter in pLSKS.

Bactericidal killing was performed on each of the complemented dsrA mutants (FIG. 7B). For strains FX517, CIP A75, CIP A77, and CIP 542 (Can), expression of dsrA from pUNCH 1260 conferred serum resistance. However, for strains harboring the plasmid vector lacking an insert serum resistance was not conferred.

EXAMPLE 16

Lipooligosaccharide Expression by *H. Ducreyi*

In some bacterial systems, mutants in LOS are more serum susceptible. Indeed, it was reported by Odumeru that the reason for the serum susceptibility of *H. ducreyi* strains CIP A75 and CIP A77 was due to LOS truncation. It was possible that the lack of dsrA expression in dsrA mutants (FX517, CIP A75, CIP A77 and CIP 542 (CAN)) resulted in the truncation of LOS directly or indirectly. Alternatively repair of dsrA expression in LOS/dsrA apparent double mutants (CIP A75 and CIP A77) might affect LOS expression and subsequent serum susceptiblity. To address these possibilities, LOS was analyzed by SDS-PAGE and silver staining (FIG. 8) and Western blotting (data not shown). We compared 35000 and FX517 LOS (without plasmids) in several silver stained gels and the migration patterns were always indistinguishable. Furthermore. Western blotting of 35000 and FX517 LOS with anti-LOS Mab 3F11 was similar.

Silver stained LOS gels of the complemented dsrA mutants were indistinguishable between each strain pair containing either pUNCH 1260 (dsrA) or pLSKS, respectively. There was a minor variation in a faster migrating LOS band for some of the strains (CIP542, no plasmid present) when grown on antibiotic free chocolate (Mueller Hinton base) as compared to the same strain (CIP542, either plasmid present) grown on streptomycin chocolate (Gonococcal medium base). However, it should be noted that within each pair of matched strains (expressing or not expressing dsrA), there were no apparent major LOS differences. Thus, under the limited conditions examined here, the presence of DsrA and not LOS length was the dominant determinant of serum resistance.

EXAMPLE 17

Structural Analysis of DsrA in Other *H. Ducreyi* Strains

Western blotting of a variety *H. ducreyi* strains (FIG. 1) suggested strongly that DsrA varied in molecular weight and/or amino acid sequence among the strains. Furthermore, we desired to understand whether mutations had occurred in the naturally occurring dsrA mutants or whether the possibility of phase variation could account for their inability to express dsrA. PCR was used to amplify a 1.2 kb fragment from 8 additional strains, including the dsrA mutants (FIG. 2, primers 14 and 24). The deduced amino acid sequence indicated that overall the DsrA protein was quite similar between strains (FIG. 9; see also FIG. 10). Two regions with modest variability were observed and termed variable region 1 and 2 (VR1 and VR2). Variable region 1 included amino acids roughly 90–100 (depending on the strain) and a few substitutions and insertions were noted. Variable region 2 contained either 1, 2, or 3 identical copies of the heptamer repeat sequence NTHNINK (SEQ ID NO:19) and spanned amino acids 174–195 in the various strains. It is likely that the different number of repeat sequences was the predominant factor accounting for the variable migration seen in SDS-PAGE and Western blotting. Excepting for mutant strain CIP542(Can), which contained a stop codon (see below), the sequences for all other 8 DsrA proteins were identical after VR2. Thus, DsrA is highly conserved in sequence, despite its variable mobility in gels.

EXAMPLE 18

Affinity Purification of DsrA Using Vitronectin (Vn)

*H. ducreyi* were surface iodinated using Iodogen-coated tubes as directed by the manufacturer. Briefly, to a tube coated with 50 μg of iodogen was added 0.5 mCi of NaI (Amersham IMS30) and 0.5 ml of 1×109. *H. ducreyi* in Phosphate buffered saline (PBS). After incubation for 2 minutes, the labeled bacteria were centrifuged and washed in medium to remove unincorporated iodine. The procedure labels primarily tyrosine residues on surfaced exposed proteins (outer membrane proteins). Each indicated biotinylated Vn was mixed with an aliquot of strain 35000 and strain FX517 whole surface-iodinated *H. ducreyi*. After Vn binding to *H. ducreyi* strains (15 min), unbound Vn was removed by centrifugation and washing. Bacteria and Vn were solubilized in the detergent ZW3,14 and insoluble material removed by centrifugation for 5 min at 15,000×g. The detergent soluble proteins were mixed with strepavidin-agarose solid phase. After incubation (2 hours), extensive washing the strepavidin-agarose with ZW3,14 in PBS, the samples were boiled in Laemmli sample buffer, and subjected to SDS-PAGE and autoradiography. The results are shown in FIG. 12, showing that affinity purification of DsrA from whole cells is possible using biotinylated vitronectins (Vn).

EXAMPLE 19

Method of Attachment of *H. Ducreyi* to Human Cells.

Efficient attachment of *H. ducreyi* to a keratinocyte cell line requires DsrA expression. *H. ducreyi* were added to the HaCaT cells at a MOI of 10:1 and incubated for 4 hours. After removal of unbound bacteria by extensive washing, CFUs were determined by plating the disrupted monolayer. Results are shown in FIG. 11, illustrating showing that efficient attachment of *H. ducreyi* to a keratinocyte cell line requires DsrA expression. Data are from 4 experiments.

The foregoing is illustrative of the present invention and is not to be construed as limiting thereof. The invention is defined by the following claims, with equivalents of the claims to be included therein.

What is claimed is:

1. An isolated polynucleotide encoding a full length Ducreyi Serum Resistance A protein (DsrA), the polynucleotide selected from the group consisting of:
   (a) DNA having the nucleotide sequence of SEQ ID NO: 1;

(b) a polynucleotide that hybridizes to the DNA of (a) above under stringent conditions by a wash stringency of 50% Formamide with 5× Denhardt's solution, 0.5% SDS and 1× SSPE at 42° C. and which encodes a full length DrsA; and (c) a polynucleotide that differs from the DNA of (a) above due to the degeneracy of the genetic code and that encodes a full length DsrA.

2. An isolated polynucleotide that encodes DsrA, wherein the DsrA has the amino acid sequence of SEQ ID NO:2.

3. The isolated polynucleotide according to claim 1 which is the DNA having the nucleotide sequence of SEQ ID NO:1.

4. An expression vector comprising the polynucleotide according to claim 1.

5. An isolated cell containing the expression vector of claim 4.

6. A method for detecting a polynucleotide which encodes DsrA in a biological sample, comprising:
   (a) contacting the complete complement of the polynucleotide sequence of claim 1 with the biological sample, thereby forming a hybridization complex; and
   (b) detecting the hybridization complex, whereby the presence of the hybridization complex detects the presence of the polynucleotide which encodes the DsrA in the biological sample.

7. A composition comprising the polynucleotide of claim 1 in a pharmaceutically acceptable carrier.

8. The composition according to claim 7 wherein the polynucleotide is the DNA having the nucleotide sequence of SEQ ID NO: 1.

9. A composition comprising the expression vector of claim 4 in a pharmaceutically acceptable carrier.

\* \* \* \* \*

UNITED STATES PATENT AND TRADEMARK OFFICE
CERTIFICATE OF CORRECTION

PATENT NO. : 7,101,989 B1
APPLICATION NO. : 10/030529
DATED : September 5, 2006
INVENTOR(S) : Elkins It is certified that error appears in the above-identified patent and that said Letters Patent is hereby corrected as shown below:

Column 73,
Line 64 should read -- above under stringent conditions represented by a wash stringency --

Signed and Sealed this

Twenty-third Day of January, 2007

JON W. DUDAS
*Director of the United States Patent and Trademark Office*

SEQUENCE LISTING

```
<160> NUMBER OF SEQ ID NOS: 23

<210> SEQ ID NO 1
<211> LENGTH: 1168
<212> TYPE: DNA
<213> ORGANISM: Haemophilus ducreyi
<220> FEATURE:
<221> NAME/KEY: CDS
<222> LOCATION: (101)..(874)
<223> OTHER INFORMATION: DsrA strain 35000

<400> SEQUENCE: 1
```

-continued

```
ataaatacgt cattgacatt tttttaatgt aaggtagaat aagaaagtaa attctatatt      60
tacaatcaag attgacaatt atttacttaa tgaggtgatt atg aaa att aaa tgt       115
                                             Met Lys Ile Lys Cys
                                             1               5 tta gtt gcc gta gtg gga tta gct tgt tct act att aca aca atg gct       163
Leu Val Ala Val Val Gly Leu Ala Cys Ser Thr Ile Thr Thr Met Ala
             10                  15                  20 cag cag ccg cca aag ttt gct gga gta tct tct ttg tat agc tat gag       211
Gln Gln Pro Pro Lys Phe Ala Gly Val Ser Ser Leu Tyr Ser Tyr Glu
         25                  30                  35 tat gac tat ggt aag ggt aaa tgg act tgg tct aat gaa ggc ggt ttc       259
Tyr Asp Tyr Gly Lys Gly Lys Trp Thr Trp Ser Asn Glu Gly Gly Phe
     40                  45                  50 gat att aaa gtg cca ggg att aaa atg aag cca aaa gaa tgg att tct       307
Asp Ile Lys Val Pro Gly Ile Lys Met Lys Pro Lys Glu Trp Ile Ser
 55                  60                  65 aaa cag gct act tat ctt gaa tta cag cat tat atg cct tat act cct       355
Lys Gln Ala Thr Tyr Leu Glu Leu Gln His Tyr Met Pro Tyr Thr Pro
70                  75                  80                  85 gtt ctc gtg aca tat gct cct ggc gtt tct cct agc cct ata ctg tta       403
Val Leu Val Thr Tyr Ala Pro Gly Val Ser Pro Ser Pro Ile Leu Leu
                 90                  95                 100 tat ccg atg tct gat cct gat caa ctt gga ata aat cgg cag cag ctg       451
Tyr Pro Met Ser Asp Pro Asp Gln Leu Gly Ile Asn Arg Gln Gln Leu
            105                 110                 115 aaa ttg aat ttg tat agt tat ttt aac gat tta aga cac gat ttt aaa       499
Lys Leu Asn Leu Tyr Ser Tyr Phe Asn Asp Leu Arg His Asp Phe Lys
        120                 125                 130 tta aaa gtt ctt gat gca cgt att tcc aaa aat aaa caa aat att gat       547
Leu Lys Val Leu Asp Ala Arg Ile Ser Lys Asn Lys Gln Asn Ile Asp
    135                 140                 145 act ata agt aaa tat tta cta gaa ctg ggt act tat tta gat gat tct       595
Thr Ile Ser Lys Tyr Leu Leu Glu Leu Gly Thr Tyr Leu Asp Asp Ser
150                 155                 160                 165 tat cgt atg atg gaa caa aat aca cat aat atc aat aag ttg tct aaa       643
Tyr Arg Met Met Glu Gln Asn Thr His Asn Ile Asn Lys Leu Ser Lys
                170                 175                 180 gaa ttg caa act ggt tta gcc aac caa tca gca ttg tct atg tta gtg       691
Glu Leu Gln Thr Gly Leu Ala Asn Gln Ser Ala Leu Ser Met Leu Val
            185                 190                 195 caa cca aat ggt gta ggc aaa acg agc gtt tct gct gcg gta gga ggt       739
Gln Pro Asn Gly Val Gly Lys Thr Ser Val Ser Ala Ala Val Gly Gly
        200                 205                 210 tat aga gat aaa act gca tta gcc att ggt gtc ggc tca cgc att act       787
Tyr Arg Asp Lys Thr Ala Leu Ala Ile Gly Val Gly Ser Arg Ile Thr
    215                 220                 225 gat cgc ttt acc gct aaa gcg ggt gta gcg ttc aat acc tac aat ggc       835
Asp Arg Phe Thr Ala Lys Ala Gly Val Ala Phe Asn Thr Tyr Asn Gly
230                 235                 240                 245 ggc atg tct tat ggt gct tct gtt ggt tat gaa ttc taa tcattacgtt       884
Gly Met Ser Tyr Gly Ala Ser Val Gly Tyr Glu Phe
                250                 255 taatcactaa tcgttttggt tataataaaa aggctaaatg tttctcctca catttagcct     944 ttcttatttta tctttgttat agcttttgct gttataaaac cgttttttag ccacttttat    1004
taattaagct tttaagccta ttcaatcagt tctactttca cttttttcac catatattcc    1064
gccacttcta aaacggtaat attaagttgg tttagcctaa attgggtacc ttctatcgga    1124
```

-continued

```
attttttcta aatgttctaa aattaagccg ttaaaggtgc ggac        1168
```

```
<210> SEQ ID NO 2
<211> LENGTH: 257
<212> TYPE: PRT
<213> ORGANISM: Haemophilus ducreyi

<400> SEQUENCE: 2
```

| | | | | | | | | | | | | | | | |
|---|---|---|---|---|---|---|---|---|---|---|---|---|---|---|---|
| Met | Lys | Ile | Lys | Cys | Leu | Val | Ala | Val | Val | Gly | Leu | Ala | Cys | Ser | Thr |
| 1 | | | | 5 | | | | | 10 | | | | | 15 | |
| Ile | Thr | Thr | Met | Ala | Gln | Gln | Pro | Pro | Lys | Phe | Ala | Gly | Val | Ser | Ser |
| | | | 20 | | | | | 25 | | | | | 30 | | |
| Leu | Tyr | Ser | Tyr | Glu | Tyr | Asp | Tyr | Gly | Lys | Gly | Lys | Trp | Thr | Trp | Ser |
| | | | 35 | | | | 40 | | | | | 45 | | | |
| Asn | Glu | Gly | Gly | Phe | Asp | Ile | Lys | Val | Pro | Gly | Ile | Lys | Met | Lys | Pro |
| | 50 | | | | | 55 | | | | | 60 | | | | |
| Lys | Glu | Trp | Ile | Ser | Lys | Gln | Ala | Thr | Tyr | Leu | Glu | Leu | Gln | His | Tyr |
| 65 | | | | | 70 | | | | | 75 | | | | | 80 |
| Met | Pro | Tyr | Thr | Pro | Val | Leu | Val | Thr | Tyr | Ala | Pro | Gly | Val | Ser | Pro |
| | | | | 85 | | | | | 90 | | | | | 95 | |
| Ser | Pro | Ile | Leu | Leu | Tyr | Pro | Met | Ser | Asp | Pro | Asp | Gln | Leu | Gly | Ile |
| | | | 100 | | | | | 105 | | | | | 110 | | |
| Asn | Arg | Gln | Gln | Leu | Lys | Leu | Asn | Leu | Tyr | Ser | Tyr | Phe | Asn | Asp | Leu |
| | | | 115 | | | | | 120 | | | | | 125 | | |
| Arg | His | Asp | Phe | Lys | Leu | Lys | Val | Leu | Asp | Ala | Arg | Ile | Ser | Lys | Asn |
| | | 130 | | | | | 135 | | | | | 140 | | | |
| Lys | Gln | Asn | Ile | Asp | Thr | Ile | Ser | Lys | Tyr | Leu | Leu | Glu | Leu | Gly | Thr |
| 145 | | | | | 150 | | | | | 155 | | | | | 160 |
| Tyr | Leu | Asp | Asp | Ser | Tyr | Arg | Met | Met | Glu | Gln | Asn | Thr | His | Asn | Ile |
| | | | | 165 | | | | | 170 | | | | | 175 | |
| Asn | Lys | Leu | Ser | Lys | Glu | Leu | Gln | Thr | Gly | Leu | Ala | Asn | Gln | Ser | Ala |
| | | | 180 | | | | | 185 | | | | | 190 | | |
| Leu | Ser | Met | Leu | Val | Gln | Pro | Asn | Gly | Val | Gly | Lys | Thr | Ser | Val | Ser |
| | | | 195 | | | | | 200 | | | | | 205 | | |
| Ala | Ala | Val | Gly | Gly | Tyr | Arg | Asp | Lys | Thr | Ala | Leu | Ala | Ile | Gly | Val |
| | 210 | | | | | 215 | | | | | 220 | | | | |
| Gly | Ser | Arg | Ile | Thr | Asp | Arg | Phe | Thr | Ala | Lys | Ala | Gly | Val | Ala | Phe |
| 225 | | | | | 230 | | | | | 235 | | | | | 240 |
| Asn | Thr | Tyr | Asn | Gly | Gly | Met | Ser | Tyr | Gly | Ala | Ser | Val | Gly | Tyr | Glu |
| | | | | 245 | | | | | 250 | | | | | 255 | |
| Phe | | | | | | | | | | | | | | | |

```
<210> SEQ ID NO 3
<211> LENGTH: 1205
<212> TYPE: DNA
<213> ORGANISM: Haemophilus ducreyi
<220> FEATURE:
<221> NAME/KEY: CDS
<222> LOCATION: (135)..(926)
<223> OTHER INFORMATION: DsrA strain CIPA75

<400> SEQUENCE: 3
attttataat ttacaataca ttttatattt ttatattata taaatacgtc attgacattt     60
ttttaaggta gaataagaaa gtaaattcta tatttacaat caagattgac aattatttac    120
ttaatgaggt gatt atg aaa att aaa tgt tta gtt gcc gta gtg gga tta     170
              Met Lys Ile Lys Cys Leu Val Ala Val Val Gly Leu
                1               5                   10
```

-continued

```
gct tgt tct act att aca aca atg gct cag cag ccg cca aag ttt gct     218
Ala Cys Ser Thr Ile Thr Thr Met Ala Gln Gln Pro Pro Lys Phe Ala
        15                  20                  25 gga gta tct tct ttg tat agc tat gag tat gac tat ggt aag ggt aaa     266
Gly Val Ser Ser Leu Tyr Ser Tyr Glu Tyr Asp Tyr Gly Lys Gly Lys
    30                  35                  40 tgg act tgg tct aat gaa ggc ggt ttc gat att aaa gtg cca ggg att     314
Trp Thr Trp Ser Asn Glu Gly Gly Phe Asp Ile Lys Val Pro Gly Ile
45                  50                  55                  60 aaa atg aag cca aaa gaa tgg att tct aaa cag gct act tat ctt gaa     362
Lys Met Lys Pro Lys Glu Trp Ile Ser Lys Gln Ala Thr Tyr Leu Glu
                65                  70                  75 tta cag cat tat atg cct tat act cct gtt ctc gtg aca tat gct cat     410
Leu Gln His Tyr Met Pro Tyr Thr Pro Val Leu Val Thr Tyr Ala His
            80                  85                  90 gac gtt cct cct agc tct ata ctg tta tat ccg atg tct gat cct gat     458
Asp Val Pro Pro Ser Ser Ile Leu Leu Tyr Pro Met Ser Asp Pro Asp
        95                  100                 105 caa ctt gga ata aat cgg cag cag ctg aaa ttg aat ttg tat agt tat     506
Gln Leu Gly Ile Asn Arg Gln Gln Leu Lys Leu Asn Leu Tyr Ser Tyr
    110                 115                 120 ttt aac gat tta aga cac gat ttt aaa tta aaa gtt ctt gat gca cgt     554
Phe Asn Asp Leu Arg His Asp Phe Lys Leu Lys Val Leu Asp Ala Arg
125                 130                 135                 140 att tcc aaa aat aaa caa aat att gat act ata agt aaa tat tta cta     602
Ile Ser Lys Asn Lys Gln Asn Ile Asp Thr Ile Ser Lys Tyr Leu Leu
                145                 150                 155 gaa ctg ggt act tat tta gat gat tct tat cgt atg atg gaa caa aat     650
Glu Leu Gly Thr Tyr Leu Asp Asp Ser Tyr Arg Met Met Glu Gln Asn
            160                 165                 170 aca cat aat atc aat aaa aat aca cat aat atc aat aag ttg tct aaa     698
Thr His Asn Ile Asn Lys Asn Thr His Asn Ile Asn Lys Leu Ser Lys
        175                 180                 185 gaa ttg caa act ggt tta gcc aac caa tca gca ttg tct atg tta gtg     746
Glu Leu Gln Thr Gly Leu Ala Asn Gln Ser Ala Leu Ser Met Leu Val
    190                 195                 200 caa cca aat ggt gta ggc aaa acg agc gtt tct gct gcg gta gga ggt     794
Gln Pro Asn Gly Val Gly Lys Thr Ser Val Ser Ala Ala Val Gly Gly
205                 210                 215                 220 tat aga gat aaa act gca tta gcc att ggt gtc ggc tca cgc att act     842
Tyr Arg Asp Lys Thr Ala Leu Ala Ile Gly Val Gly Ser Arg Ile Thr
                225                 230                 235 gat cgc ttt acc gct aaa gcg ggt gta gcg ttc aat acc tac aat ggc     890
Asp Arg Phe Thr Ala Lys Ala Gly Val Ala Phe Asn Thr Tyr Asn Gly
            240                 245                 250 ggc atg tct tat ggt gct tct gtt ggt tat gaa ttc taatcattac          936
Gly Met Ser Tyr Gly Ala Ser Val Gly Tyr Glu Phe
        255                 260 gtttaatcac taatcgtttt ggttataata aaaaggctaa atgtttctcc tcacatttag   996
cctttcttat ttatctttgt tatagctttt gctgttataa aaccgttttt tagcccacttt  1056 tattaattaa gctttaagc ctattcaatc agttctactt tcacttttt caccatatta    1116 tccgccactt ctaaaacggt aatattaagt tggtttagcc taaattgggt accttctatc   1176
ggaatttttt ctaaatgttc taaaattaa                                    1205
```

<210> SEQ ID NO 4
<211> LENGTH: 264
<212> TYPE: PRT

<213> ORGANISM: Haemophilus ducreyi

<400> SEQUENCE: 4

| Met | Lys | Ile | Lys | Cys | Leu | Val | Ala | Val | Val | Gly | Leu | Ala | Cys | Ser | Thr |
|---|---|---|---|---|---|---|---|---|---|---|---|---|---|---|---|
| 1 | | | | 5 | | | | | 10 | | | | | 15 | |

| Ile | Thr | Thr | Met | Ala | Gln | Gln | Pro | Pro | Lys | Phe | Ala | Gly | Val | Ser | Ser |
| | | | 20 | | | | | 25 | | | | | 30 | | |

| Leu | Tyr | Ser | Tyr | Glu | Tyr | Asp | Tyr | Gly | Lys | Gly | Lys | Trp | Thr | Trp | Ser |
| | | 35 | | | | | 40 | | | | | 45 | | | |

| Asn | Glu | Gly | Gly | Phe | Asp | Ile | Lys | Val | Pro | Gly | Ile | Lys | Met | Lys | Pro |
| 50 | | | | | 55 | | | | | 60 | | | | | |

| Lys | Glu | Trp | Ile | Ser | Lys | Gln | Ala | Thr | Tyr | Leu | Glu | Leu | Gln | His | Tyr |
| 65 | | | | 70 | | | | | 75 | | | | | 80 | |

| Met | Pro | Tyr | Thr | Pro | Val | Leu | Val | Thr | Tyr | Ala | His | Asp | Val | Pro | Pro |
| | | | | 85 | | | | | 90 | | | | | 95 | |

| Ser | Ser | Ile | Leu | Leu | Tyr | Pro | Met | Ser | Asp | Pro | Asp | Gln | Leu | Gly | Ile |
| | | | 100 | | | | | 105 | | | | | 110 | | |

| Asn | Arg | Gln | Gln | Leu | Lys | Leu | Asn | Leu | Tyr | Ser | Tyr | Phe | Asn | Asp | Leu |
| | | 115 | | | | | 120 | | | | | 125 | | | |

| Arg | His | Asp | Phe | Lys | Leu | Lys | Val | Leu | Asp | Ala | Arg | Ile | Ser | Lys | Asn |
| | 130 | | | | | 135 | | | | | 140 | | | | |

| Lys | Gln | Asn | Ile | Asp | Thr | Ile | Ser | Lys | Tyr | Leu | Leu | Glu | Leu | Gly | Thr |
| 145 | | | | | 150 | | | | | 155 | | | | | 160 |

| Tyr | Leu | Asp | Asp | Ser | Tyr | Arg | Met | Met | Glu | Gln | Asn | Thr | His | Asn | Ile |
| | | | | 165 | | | | | 170 | | | | | 175 | |

| Asn | Lys | Asn | Thr | His | Asn | Ile | Asn | Lys | Leu | Ser | Lys | Glu | Leu | Gln | Thr |
| | | | 180 | | | | | 185 | | | | | 190 | | |

| Gly | Leu | Ala | Asn | Gln | Ser | Ala | Leu | Ser | Met | Leu | Val | Gln | Pro | Asn | Gly |
| | | 195 | | | | | 200 | | | | | 205 | | | |

| Val | Gly | Lys | Thr | Ser | Val | Ser | Ala | Ala | Val | Gly | Gly | Tyr | Arg | Asp | Lys |
| | 210 | | | | | 215 | | | | | 220 | | | | |

| Thr | Ala | Leu | Ala | Ile | Gly | Val | Gly | Ser | Arg | Ile | Thr | Asp | Arg | Phe | Thr |
| 225 | | | | | 230 | | | | | 235 | | | | | 240 |

| Ala | Lys | Ala | Gly | Val | Ala | Phe | Asn | Thr | Tyr | Asn | Gly | Gly | Met | Ser | Tyr |
| | | | | 245 | | | | | 250 | | | | | 255 | |

| Gly | Ala | Ser | Val | Gly | Tyr | Glu | Phe |
| | | | 260 | | | | |

```
<210> SEQ ID NO 5
<211> LENGTH: 952
<212> TYPE: DNA
<213> ORGANISM: Haemophilus ducreyi
<220> FEATURE:
<221> NAME/KEY: CDS
<222> LOCATION: (135)..(926)
<223> OTHER INFORMATION: DsrA strain CIPA77
```

<400> SEQUENCE: 5

| attttataat | ttacaataca | ttttatattt | ttatattata | taaatacgtc | attgacattt | 60 |
| ttttaaggta | gaataagaaa | gtaaattcta | tatttacaat | caagattgac | aattatttac | 120 |

| ttaatgaggt gatt | atg | aaa | att | aaa | tgt | tta | gtt | gcc | gta | gtg | gga | tta | | 170 |
| | Met | Lys | Ile | Lys | Cys | Leu | Val | Ala | Val | Val | Gly | Leu | | |
| | 1 | | | | 5 | | | | | 10 | | | | |

| gct | tgt | tct | act | att | aca | aca | atg | gct | cag | cag | ccg | cca | aag | ttt | gct | 218 |
| Ala | Cys | Ser | Thr | Ile | Thr | Thr | Met | Ala | Gln | Gln | Pro | Pro | Lys | Phe | Ala | |
| | 15 | | | | | 20 | | | | | 25 | | | | | |

```
                                                                -continued gga gta tct tct ttg tat agc tat gag tat gac tat ggt aag ggt aaa      266
Gly Val Ser Ser Leu Tyr Ser Tyr Glu Tyr Asp Tyr Gly Lys Gly Lys
    30                  35                  40 tgg act tgg tct aat gaa ggc ggt ttc gat att aaa gtg cca ggg att      314
Trp Thr Trp Ser Asn Glu Gly Gly Phe Asp Ile Lys Val Pro Gly Ile
45                  50                  55                  60 aaa atg aag cca aaa gaa tgg att tct aaa cag gct act tat ctt gaa      362
Lys Met Lys Pro Lys Glu Trp Ile Ser Lys Gln Ala Thr Tyr Leu Glu
                65                  70                  75 tta cag cat tat atg cct tat act cct gtt ctc gtg aca tat gct cat      410
Leu Gln His Tyr Met Pro Tyr Thr Pro Val Leu Val Thr Tyr Ala His
            80                  85                  90 gac gtt cct cct agc tct ata ctg tta tat ccg atg tct gat cct gat      458
Asp Val Pro Pro Ser Ser Ile Leu Leu Tyr Pro Met Ser Asp Pro Asp
        95                  100                 105 caa ctt gga ata aat cgg cag cag ctg aaa ttg aat ttg tat agt tat      506
Gln Leu Gly Ile Asn Arg Gln Gln Leu Lys Leu Asn Leu Tyr Ser Tyr
    110                 115                 120 ttt aac gat tta aga cac gat ttt aaa tta aaa gtt ctt gat gca cgt      554
Phe Asn Asp Leu Arg His Asp Phe Lys Leu Lys Val Leu Asp Ala Arg
125                 130                 135                 140 att tcc aaa aat aaa caa aat att gat act ata agt aaa tat tta cta      602
Ile Ser Lys Asn Lys Gln Asn Ile Asp Thr Ile Ser Lys Tyr Leu Leu
                145                 150                 155 gaa ctg ggt act tat tta gat gat tct tat cgt atg atg gaa caa aat      650
Glu Leu Gly Thr Tyr Leu Asp Asp Ser Tyr Arg Met Met Glu Gln Asn
            160                 165                 170 aca cat aat atc aat aaa aat aca cat aat atc aat aag ttg tct aaa      698
Thr His Asn Ile Asn Lys Asn Thr His Asn Ile Asn Lys Leu Ser Lys
        175                 180                 185 gaa ttg caa act ggt tta gcc aac caa tca gca ttg tct atg tta gtg      746
Glu Leu Gln Thr Gly Leu Ala Asn Gln Ser Ala Leu Ser Met Leu Val
    190                 195                 200 caa cca aat ggt gta ggc aaa acg agc gtt tct gct gcg gta gga ggt      794
Gln Pro Asn Gly Val Gly Lys Thr Ser Val Ser Ala Ala Val Gly Gly
205                 210                 215                 220 tat aga gat aaa act gca tta gcc att ggt gtc ggc tca cgc att act      842
Tyr Arg Asp Lys Thr Ala Leu Ala Ile Gly Val Gly Ser Arg Ile Thr
                225                 230                 235 gat cgc ttt acc gct aaa gcg ggt gta gcg ttc aat acc tac aat ggc      890
Asp Arg Phe Thr Ala Lys Ala Gly Val Ala Phe Asn Thr Tyr Asn Gly
            240                 245                 250 ggc atg tct tat ggt gct tct gtt ggt tat gaa ttc taatcattac           936
Gly Met Ser Tyr Gly Ala Ser Val Gly Tyr Glu Phe
        255                 260 gtttaatcac taatcg                                                    952

<210> SEQ ID NO 6
<211> LENGTH: 264
<212> TYPE: PRT
<213> ORGANISM: Haemophilus ducreyi

<400> SEQUENCE: 6

Met Lys Ile Lys Cys Leu Val Ala Val Val Gly Leu Ala Cys Ser Thr
1               5                   10                  15

Ile Thr Thr Met Ala Gln Gln Pro Pro Lys Phe Ala Gly Val Ser Ser
            20                  25                  30

Leu Tyr Ser Tyr Glu Tyr Asp Tyr Gly Lys Gly Lys Trp Thr Trp Ser
        35                  40                  45
```

-continued

```
Asn Glu Gly Gly Phe Asp Ile Lys Val Pro Gly Ile Lys Met Lys Pro
 50                  55                  60
Lys Glu Trp Ile Ser Lys Gln Ala Thr Tyr Leu Glu Leu Gln His Tyr
 65                  70                  75                  80
Met Pro Tyr Thr Pro Val Leu Val Thr Tyr Ala His Asp Val Pro Pro
                 85                  90                  95
Ser Ser Ile Leu Leu Tyr Pro Met Ser Asp Pro Asp Gln Leu Gly Ile
            100                 105                 110
Asn Arg Gln Gln Leu Lys Leu Asn Leu Tyr Ser Tyr Phe Asn Asp Leu
            115                 120                 125
Arg His Asp Phe Lys Leu Lys Val Leu Asp Ala Arg Ile Ser Lys Asn
130                 135                 140
Lys Gln Asn Ile Asp Thr Ile Ser Lys Tyr Leu Leu Glu Leu Gly Thr
145                 150                 155                 160
Tyr Leu Asp Asp Ser Tyr Arg Met Met Glu Gln Asn Thr His Asn Ile
                165                 170                 175
Asn Lys Asn Thr His Asn Ile Asn Lys Leu Ser Lys Glu Leu Gln Thr
            180                 185                 190
Gly Leu Ala Asn Gln Ser Ala Leu Ser Met Leu Val Gln Pro Asn Gly
            195                 200                 205
Val Gly Lys Thr Ser Val Ser Ala Ala Val Gly Gly Tyr Arg Asp Lys
210                 215                 220
Thr Ala Leu Ala Ile Gly Val Gly Ser Arg Ile Thr Asp Arg Phe Thr
225                 230                 235                 240
Ala Lys Ala Gly Val Ala Phe Asn Thr Tyr Asn Gly Gly Met Ser Tyr
                245                 250                 255
Gly Ala Ser Val Gly Tyr Glu Phe
            260

<210> SEQ ID NO 7
<211> LENGTH: 899
<212> TYPE: DNA
<213> ORGANISM: Haemophilus ducreyi
<220> FEATURE:
<221> NAME/KEY: CDS
<222> LOCATION: (139)..(882)
<223> OTHER INFORMATION: DsrA strain CIP542 (Can)

<400> SEQUENCE: 7 tttataatt  tacaatacat  tttatatttt  tatattatat  aaatacgtca  ttgacatttt      60
tttaatgtaa  ggtagaataa  gaaagtaaat  tctatattta  caatcaagat  tgacaattat    120
ttacttaatg aggtgatt atg aaa att aaa tgt tta gtt gcc gta gtg gga      171
                    Met Lys Ile Lys Cys Leu Val Ala Val Val Gly
                     1               5                  10 tta gct tgt tct act att aca aca atg gct cag cag ccg cca aag ttt      219
Leu Ala Cys Ser Thr Ile Thr Thr Met Ala Gln Gln Pro Pro Lys Phe
             15                  20                  25 gct gga gta tct tct ttg tat agc tat gag tat gac tat ggt aag ggt      267
Ala Gly Val Ser Ser Leu Tyr Ser Tyr Glu Tyr Asp Tyr Gly Lys Gly
         30                  35                  40 aaa tgg act tgg tct aat gaa ggc ggt ttc gat att aaa gtg cca ggg      315
Lys Trp Thr Trp Ser Asn Glu Gly Gly Phe Asp Ile Lys Val Pro Gly
 45                  50                  55 att aaa atg aag cca aaa gaa tgg att tct aaa cag gct act tat ctt      363
Ile Lys Met Lys Pro Lys Glu Trp Ile Ser Lys Gln Ala Thr Tyr Leu
 60                  65                  70                  75 gaa tta cag cat tat atg cct tat act cct gtt ctc gtg aca tat gct      411
```

| | | | | | | | | | | | | | | |
|---|---|---|---|---|---|---|---|---|---|---|---|---|---|---|
| Glu | Leu | Gln | His | Tyr | Met | Pro | Tyr | Thr | Pro | Val | Leu | Val | Thr | Tyr | Ala |
| | | | 80 | | | | 85 | | | | 90 | | | | |

```
cct ggc gtt tct cct agc cct ata ctg tta tat ccg atg tct gat cct   459
Pro Gly Val Ser Pro Ser Pro Ile Leu Leu Tyr Pro Met Ser Asp Pro
         95                 100                 105 gat caa ctt gga ata aat cgg cag cag ctg aaa ttg aat ttg tat agt   507
Asp Gln Leu Gly Ile Asn Arg Gln Gln Leu Lys Leu Asn Leu Tyr Ser
             110                 115                 120 tat ttt aac gat tta aga cac gat ttt aaa tta aaa gtt ctt gat gca   555
Tyr Phe Asn Asp Leu Arg His Asp Phe Lys Leu Lys Val Leu Asp Ala
        125                 130                 135 cgt att tcc aaa aat aaa caa aat att gat act ata agt aaa tat tta   603
Arg Ile Ser Lys Asn Lys Gln Asn Ile Asp Thr Ile Ser Lys Tyr Leu
140                 145                 150                 155 cta gaa ctg ggt act tat tta gat gat tct tat cgt atg atg gaa caa   651
Leu Glu Leu Gly Thr Tyr Leu Asp Asp Ser Tyr Arg Met Met Glu Gln
                    160                 165                 170 aat aca cat aat atc aat aag ttg tct aaa gaa ttg caa act ggt tta   699
Asn Thr His Asn Ile Asn Lys Leu Ser Lys Glu Leu Gln Thr Gly Leu
                175                 180                 185 gcc aac caa tca gca ttg tct atg tta gtg caa cca aat ggt gta ggc   747
Ala Asn Gln Ser Ala Leu Ser Met Leu Val Gln Pro Asn Gly Val Gly
            190                 195                 200 aaa acg agc gtt tct gct gcg gta gga ggt tat aga gat aaa act gca   795
Lys Thr Ser Val Ser Ala Ala Val Gly Gly Tyr Arg Asp Lys Thr Ala
        205                 210                 215 tta gcc att ggt gtc ggc tca cgc att act gat cgc ttt acc gct aaa   843
Leu Ala Ile Gly Val Gly Ser Arg Ile Thr Asp Arg Phe Thr Ala Lys
220                 225                 230                 235 gcg ggt gta gcg ttc aat acc ttc tat cgg aat ttt ttc taaatgttct    892
Ala Gly Val Ala Phe Asn Thr Phe Tyr Arg Asn Phe Phe
                    240                 245 aaaatta                                                           899
```

<210> SEQ ID NO 8
<211> LENGTH: 248
<212> TYPE: PRT
<213> ORGANISM: Haemophilus ducreyi

<400> SEQUENCE: 8

```
Met Lys Ile Lys Cys Leu Val Ala Val Val Gly Leu Ala Cys Ser Thr
1               5                   10                  15

Ile Thr Thr Met Ala Gln Gln Pro Pro Lys Phe Ala Gly Val Ser Ser
            20                  25                  30

Leu Tyr Ser Tyr Glu Tyr Asp Tyr Gly Lys Gly Lys Trp Thr Trp Ser
        35                  40                  45

Asn Glu Gly Gly Phe Asp Ile Lys Val Pro Gly Ile Lys Met Lys Pro
    50                  55                  60

Lys Glu Trp Ile Ser Lys Gln Ala Thr Tyr Leu Glu Leu Gln His Tyr
65                  70                  75                  80

Met Pro Tyr Thr Pro Val Leu Val Thr Tyr Ala Pro Gly Val Ser Pro
                85                  90                  95

Ser Pro Ile Leu Leu Tyr Pro Met Ser Asp Pro Asp Gln Leu Gly Ile
            100                 105                 110

Asn Arg Gln Gln Leu Lys Leu Asn Leu Tyr Ser Tyr Phe Asn Asp Leu
        115                 120                 125

Arg His Asp Phe Lys Leu Lys Val Leu Asp Ala Arg Ile Ser Lys Asn
    130                 135                 140
```

```
Lys Gln Asn Ile Asp Thr Ile Ser Lys Tyr Leu Leu Glu Leu Gly Thr
145                 150                 155                 160

Tyr Leu Asp Asp Ser Tyr Arg Met Met Glu Gln Asn Thr His Asn Ile
                165                 170                 175

Asn Lys Leu Ser Lys Glu Leu Gln Thr Gly Leu Ala Asn Gln Ser Ala
            180                 185                 190

Leu Ser Met Leu Val Gln Pro Asn Gly Val Gly Lys Thr Ser Val Ser
        195                 200                 205

Ala Ala Val Gly Gly Tyr Arg Asp Lys Thr Ala Leu Ala Ile Gly Val
    210                 215                 220

Gly Ser Arg Ile Thr Asp Arg Phe Thr Ala Lys Ala Gly Val Ala Phe
225                 230                 235                 240

Asn Thr Phe Tyr Arg Asn Phe Phe
                245

<210> SEQ ID NO 9
<211> LENGTH: 1197
<212> TYPE: DNA
<213> ORGANISM: Haemophilus ducreyi
<220> FEATURE:
<221> NAME/KEY: CDS
<222> LOCATION: (147)..(917)
<223> OTHER INFORMATION: DsrA strain CIP542 (CDC)

<400> SEQUENCE: 9
aatggccatt ttataattta caatacattt tatattttta tattatataa atacgtcatt    60 gacattttt taatgtaagg tagaataaga aagtaaattc tatatttaca atcaagattg    120
acaattattt acttaatgag gtgatt atg aaa att aaa tgt tta gtt gcc gta   173
                              Met Lys Ile Lys Cys Leu Val Ala Val
                               1               5 gtg gga tta gct tgt tct act att aca aca atg gct cag cag ccg cca   221
Val Gly Leu Ala Cys Ser Thr Ile Thr Thr Met Ala Gln Gln Pro Pro
 10              15                  20                  25 aag ttt gct gga gta tct tct ttg tat agc tat gag tat gac tat ggt   269
Lys Phe Ala Gly Val Ser Ser Leu Tyr Ser Tyr Glu Tyr Asp Tyr Gly
             30                  35                  40 aag ggt aaa tgg act tgg tct aat gaa ggc ggt ttc gat att aaa gtg   317
Lys Gly Lys Trp Thr Trp Ser Asn Glu Gly Gly Phe Asp Ile Lys Val
         45                  50                  55 cca ggg att aaa atg aag cca aaa gaa tgg att tct aaa cag gct act   365
Pro Gly Ile Lys Met Lys Pro Lys Glu Trp Ile Ser Lys Gln Ala Thr
     60                  65                  70 tat ctt gaa tta cag cat tat atg cct tat act cct gtt ctc gtg aca   413
Tyr Leu Glu Leu Gln His Tyr Met Pro Tyr Thr Pro Val Leu Val Thr
 75                  80                  85 tat gct cct ggc gtt tct cct agc cct ata ctg tta tat ccg atg tct   461
Tyr Ala Pro Gly Val Ser Pro Ser Pro Ile Leu Leu Tyr Pro Met Ser
 90                  95                 100                 105 gat cct gat caa ctt gga ata aat cgg cag cag ctg aaa ttg aat ttg   509
Asp Pro Asp Gln Leu Gly Ile Asn Arg Gln Gln Leu Lys Leu Asn Leu
                110                 115                 120 tat agt tat ttt aac gat tta aga cac gat ttt aaa tta aaa gtt ctt   557
Tyr Ser Tyr Phe Asn Asp Leu Arg His Asp Phe Lys Leu Lys Val Leu
            125                 130                 135 gat gca cgt att tcc aaa aat aaa caa aat att gat act ata agt aaa   605
Asp Ala Arg Ile Ser Lys Asn Lys Gln Asn Ile Asp Thr Ile Ser Lys
        140                 145                 150 tat tta cta gaa ctg ggt act tat tta gat gat tct tat cgt atg atg   653
```

-continued

```
Tyr Leu Leu Glu Leu Gly Thr Tyr Leu Asp Asp Ser Tyr Arg Met Met
            155                 160                 165 gaa caa aat aca cat aat atc aat aag ttg tct aaa gaa ttg caa act      701
Glu Gln Asn Thr His Asn Ile Asn Lys Leu Ser Lys Glu Leu Gln Thr
170                 175                 180                 185 ggt tta gcc aac caa tca gca ttg tct atg tta gtg caa cca aat ggt      749
Gly Leu Ala Asn Gln Ser Ala Leu Ser Met Leu Val Gln Pro Asn Gly
                190                 195                 200 gta ggc aaa acg agc gtt tct gct gcg gta gga ggt tat aga gat aaa      797
Val Gly Lys Thr Ser Val Ser Ala Ala Val Gly Gly Tyr Arg Asp Lys
            205                 210                 215 act gca tta gcc att ggt gtc ggc tca cgc att act gat cgc ttt acc      845
Thr Ala Leu Ala Ile Gly Val Gly Ser Arg Ile Thr Asp Arg Phe Thr
        220                 225                 230 gct aaa gcg ggt gta gcg ttc aat acc tac aat ggc ggc atg tct tat      893
Ala Lys Ala Gly Val Ala Phe Asn Thr Tyr Asn Gly Gly Met Ser Tyr
    235                 240                 245 ggt gct tct gtt ggt tat gaa ttc taatcattac gtttaatcac taatcgtttt     947
Gly Ala Ser Val Gly Tyr Glu Phe
250                 255 ggttataata aaaggctaa atgtttctcc tcacatttag cctttcttat ttatctttgt    1007
tatagccttt tgctgttata aaaccgtttt ttagccactt ttattaatta agcttttaag   1067
cctattcaat cagttctact ttcactttt tcaccatatt atccgccact tctaaaacgg    1127
taatattaag ttggtttagc ctaaattggg taccttctat cggaattttt tctaaatgtt   1187
ctaaaattaa                                                          1197

<210> SEQ ID NO 10
<211> LENGTH: 257
<212> TYPE: PRT
<213> ORGANISM: Haemophilus ducreyi

<400> SEQUENCE: 10

Met Lys Ile Lys Cys Leu Val Ala Val Val Gly Leu Ala Cys Ser Thr
1               5                   10                  15

Ile Thr Thr Met Ala Gln Gln Pro Pro Lys Phe Ala Gly Val Ser Ser
            20                  25                  30

Leu Tyr Ser Tyr Glu Tyr Asp Tyr Gly Lys Gly Lys Trp Thr Trp Ser
        35                  40                  45

Asn Glu Gly Gly Phe Asp Ile Lys Val Pro Gly Ile Lys Met Lys Pro
    50                  55                  60

Lys Glu Trp Ile Ser Lys Gln Ala Thr Tyr Leu Glu Leu Gln His Tyr
65                  70                  75                  80

Met Pro Tyr Thr Pro Val Leu Val Thr Tyr Ala Pro Gly Val Ser Pro
                85                  90                  95

Ser Pro Ile Leu Leu Tyr Pro Met Ser Asp Pro Asp Gln Leu Gly Ile
            100                 105                 110

Asn Arg Gln Gln Leu Lys Leu Asn Leu Tyr Ser Tyr Phe Asn Asp Leu
        115                 120                 125

Arg His Asp Phe Lys Leu Lys Val Leu Asp Ala Arg Ile Ser Lys Asn
    130                 135                 140

Lys Gln Asn Ile Asp Thr Ile Ser Lys Tyr Leu Leu Glu Leu Gly Thr
145                 150                 155                 160

Tyr Leu Asp Asp Ser Tyr Arg Met Met Glu Gln Asn Thr His Asn Ile
                165                 170                 175

Asn Lys Leu Ser Lys Glu Leu Gln Thr Gly Leu Ala Asn Gln Ser Ala
```

-continued

```
                180                 185                 190
Leu Ser Met Leu Val Gln Pro Asn Gly Val Gly Lys Thr Ser Val Ser
                    195                 200                 205

Ala Ala Val Gly Gly Tyr Arg Asp Lys Thr Ala Leu Ala Ile Gly Val
        210                 215                 220

Gly Ser Arg Ile Thr Asp Arg Phe Thr Ala Lys Ala Gly Val Ala Phe
225                 230                 235                 240

Asn Thr Tyr Asn Gly Gly Met Ser Tyr Gly Ala Ser Val Gly Tyr Glu
                245                 250                 255

Phe

<210> SEQ ID NO 11
<211> LENGTH: 923
<212> TYPE: DNA
<213> ORGANISM: Haemophilus ducreyi
<220> FEATURE:
<221> NAME/KEY: CDS
<222> LOCATION: (45)..(833)
<223> OTHER INFORMATION: DsrA strain CHIA

<400> SEQUENCE: 11
tatttacaat caagattgac aattatttac ttaatgaggt gatt atg aaa att aaa      56
                                               Met Lys Ile Lys
                                               1 tgt tta gtt gcc gta gtg gga tta gct tgt tct act att aca aca atg    104
Cys Leu Val Ala Val Val Gly Leu Ala Cys Ser Thr Ile Thr Thr Met
5                   10                  15                  20 gct cag cag ccg cca aag ttt gct gga gta tct tct ttg gat agc tat    152
Ala Gln Gln Pro Pro Lys Phe Ala Gly Val Ser Ser Leu Asp Ser Tyr
                25                  30                  35 gag tat gac tat ggt aag ggt aaa tgg act tgg tct gaa aaa gac ggt    200
Glu Tyr Asp Tyr Gly Lys Gly Lys Trp Thr Trp Ser Glu Lys Asp Gly
            40                  45                  50 ttc gat att aaa gcg cca ggg att aaa atg aag cca aaa aaa tgg att    248
Phe Asp Ile Lys Ala Pro Gly Ile Lys Met Lys Pro Lys Lys Trp Ile
        55                  60                  65 tct aga cag gct act tat ctt gga tta cag cat tat atg cct tat act    296
Ser Arg Gln Ala Thr Tyr Leu Gly Leu Gln His Tyr Met Pro Tyr Thr
    70                  75                  80 cct gtt ctc gtg aca tat gct tct gca gaa cct aac act gta ctg tta    344
Pro Val Leu Val Thr Tyr Ala Ser Ala Glu Pro Asn Thr Val Leu Leu
85                  90                  95                  100 tat ccg atg cct gat cct gat caa ctt gga ata aat cgg cag cag ctg    392
Tyr Pro Met Pro Asp Pro Asp Gln Leu Gly Ile Asn Arg Gln Gln Leu
                105                 110                 115 aaa ttg aat ttg tat agt tat ttt aac gat tta aga cac ggt ttt aaa    440
Lys Leu Asn Leu Tyr Ser Tyr Phe Asn Asp Leu Arg His Gly Phe Lys
            120                 125                 130 tta aat gtt ctt gat gca cgt att tcc caa aat aaa caa aat att gat    488
Leu Asn Val Leu Asp Ala Arg Ile Ser Gln Asn Lys Gln Asn Ile Asp
        135                 140                 145 act ata agt gaa tat tta cta aaa ctg ggt act tat tta gat agt tct    536
Thr Ile Ser Glu Tyr Leu Leu Lys Leu Gly Thr Tyr Leu Asp Ser Ser
    150                 155                 160 tat cgt atg atg gaa caa aat aca cat aat atc aat aaa aat aca cat    584
Tyr Arg Met Met Glu Gln Asn Thr His Asn Ile Asn Lys Asn Thr His
165                 170                 175                 180 aat atc aat aag ttg tct aaa gaa ttg caa act ggt tta gcc aac caa    632
Asn Ile Asn Lys Leu Ser Lys Glu Leu Gln Thr Gly Leu Ala Asn Gln
                185                 190                 195
```

```
tca gca ttg tct atg tta gtg caa cca aat ggt gta ggc aaa acg agc      680
Ser Ala Leu Ser Met Leu Val Gln Pro Asn Gly Val Gly Lys Thr Ser
        200                 205                 210 gtt tct gct gcg gta gga ggt tat aga gat aaa act gca tta gcc att      728
Val Ser Ala Ala Val Gly Gly Tyr Arg Asp Lys Thr Ala Leu Ala Ile
            215                 220                 225 ggt gtc ggc tca cgc att act gat cgc ttt acc gct aaa gcg ggt gta      776
Gly Val Gly Ser Arg Ile Thr Asp Arg Phe Thr Ala Lys Ala Gly Val
    230                 235                 240 gcg ttc aat acc tac aat ggc ggc atg tct tat ggt gct tct gtt ggt      824
Ala Phe Asn Thr Tyr Asn Gly Gly Met Ser Tyr Gly Ala Ser Val Gly
245                 250                 255                 260 tat gaa ttc taatcattac gtttaatcac taatcgtttt ggttataata              873
Tyr Glu Phe aaaaggctaa atgtttctcc tcacatttag cctttcttat ttatctttgt               923
```

<210> SEQ ID NO 12
<211> LENGTH: 263
<212> TYPE: PRT
<213> ORGANISM: Haemophilus ducreyi

<400> SEQUENCE: 12

```
Met Lys Ile Lys Cys Leu Val Ala Val Val Gly Leu Ala Cys Ser Thr
1               5                   10                  15

Ile Thr Thr Met Ala Gln Gln Pro Pro Lys Phe Ala Gly Val Ser Ser
            20                  25                  30

Leu Asp Ser Tyr Glu Tyr Asp Tyr Gly Lys Gly Lys Trp Thr Trp Ser
        35                  40                  45

Glu Lys Asp Gly Phe Asp Ile Lys Ala Pro Gly Ile Lys Met Lys Pro
    50                  55                  60

Lys Lys Trp Ile Ser Arg Gln Ala Thr Tyr Leu Gly Leu Gln His Tyr
65                  70                  75                  80

Met Pro Tyr Thr Pro Val Leu Val Thr Tyr Ala Ser Ala Glu Pro Asn
                85                  90                  95

Thr Val Leu Leu Tyr Pro Met Pro Asp Pro Asp Gln Leu Gly Ile Asn
            100                 105                 110

Arg Gln Gln Leu Lys Leu Asn Leu Tyr Ser Tyr Phe Asn Asp Leu Arg
        115                 120                 125

His Gly Phe Lys Leu Asn Val Leu Asp Ala Arg Ile Ser Gln Asn Lys
    130                 135                 140

Gln Asn Ile Asp Thr Ile Ser Glu Tyr Leu Leu Lys Leu Gly Thr Tyr
145                 150                 155                 160

Leu Asp Ser Ser Tyr Arg Met Met Glu Gln Asn Thr His Asn Ile Asn
                165                 170                 175

Lys Asn Thr His Asn Ile Asn Lys Leu Ser Lys Glu Leu Gln Thr Gly
            180                 185                 190

Leu Ala Asn Gln Ser Ala Leu Ser Met Leu Val Gln Pro Asn Gly Val
        195                 200                 205

Gly Lys Thr Ser Val Ser Ala Val Gly Gly Tyr Arg Asp Lys Thr
    210                 215                 220

Ala Leu Ala Ile Gly Val Gly Ser Arg Ile Thr Asp Arg Phe Thr Ala
225                 230                 235                 240

Lys Ala Gly Val Ala Phe Asn Thr Tyr Asn Gly Gly Met Ser Tyr Gly
                245                 250                 255

Ala Ser Val Gly Tyr Glu Phe
```

-continued

260

<210> SEQ ID NO 13
<211> LENGTH: 1231
<212> TYPE: DNA
<213> ORGANISM: Haemophilus ducreyi
<220> FEATURE:
<221> NAME/KEY: CDS
<222> LOCATION: (140)..(952)
<223> OTHER INFORMATION: DsrA strain V-1157

<400> SEQUENCE: 13

```
cttttataat ttacaataca ttttatattt ttatattata taaatacgtc attgacattt      60
ttttaatgta aggtagaata agaaagtaaa ttctatattt acaatcaaga ttgacaatta     120
tttacttaat gaggtgatt atg aaa att aaa tgt tta gtt gcc gta gtg gga     172
               Met Lys Ile Lys Cys Leu Val Ala Val Val Gly
                 1               5                  10 tta gct tgt tct act att aca aca atg gct cag cag ccg cca aag ttt     220
Leu Ala Cys Ser Thr Ile Thr Thr Met Ala Gln Gln Pro Pro Lys Phe
            15                  20                  25 gct gga gta tct tct ttg tat agc tat gag tat gac tat ggt aag ggt     268
Ala Gly Val Ser Ser Leu Tyr Ser Tyr Glu Tyr Asp Tyr Gly Lys Gly
        30                  35                  40 aaa tgg act tgg tct aat gaa ggc ggt ttc gat att aaa gtg cca ggg     316
Lys Trp Thr Trp Ser Asn Glu Gly Gly Phe Asp Ile Lys Val Pro Gly
    45                  50                  55 att aaa atg aag cca aaa gaa tgg att tct aaa cag gct act tat ctt     364
Ile Lys Met Lys Pro Lys Glu Trp Ile Ser Lys Gln Ala Thr Tyr Leu
60                  65                  70                  75 gaa tta cag cat tat atg cct tat act cct gtt ctc gtg aca tct gct     412
Glu Leu Gln His Tyr Met Pro Tyr Thr Pro Val Leu Val Thr Ser Ala
                80                  85                  90 cct gac gtt cct cct agc tct ata ctg tta tat ccg atg tct gat cct     460
Pro Asp Val Pro Pro Ser Ser Ile Leu Leu Tyr Pro Met Ser Asp Pro
            95                 100                 105 gat caa ctt gga ata aat cgg cag cag ctg aaa ttg aat ttg tat agt     508
Asp Gln Leu Gly Ile Asn Arg Gln Gln Leu Lys Leu Asn Leu Tyr Ser
        110                 115                 120 tat ttt aac gat tta aga cac gat ttt aaa tta aaa gtt ctt gat gca     556
Tyr Phe Asn Asp Leu Arg His Asp Phe Lys Leu Lys Val Leu Asp Ala
    125                 130                 135 cgt att tcc aaa aat aaa caa aat att gat act ata agt aaa tat tta     604
Arg Ile Ser Lys Asn Lys Gln Asn Ile Asp Thr Ile Ser Lys Tyr Leu
140                 145                 150                 155 cta gaa ctg ggt act tat tta gat ggt tct tat cgt atg atg gaa caa     652
Leu Glu Leu Gly Thr Tyr Leu Asp Gly Ser Tyr Arg Met Met Glu Gln
                160                 165                 170 aat aca cat aat atc aat aaa aat aca cat aat atc aat aaa aat aca     700
Asn Thr His Asn Ile Asn Lys Asn Thr His Asn Ile Asn Lys Asn Thr
            175                 180                 185 cat aat atc aat aag ttg tct aaa gaa ttg caa act ggt tta gcc aac     748
His Asn Ile Asn Lys Leu Ser Lys Glu Leu Gln Thr Gly Leu Ala Asn
        190                 195                 200 caa tca gca ttg tct atg tta gtg caa cca aat ggt gta ggc aaa acg     796
Gln Ser Ala Leu Ser Met Leu Val Gln Pro Asn Gly Val Gly Lys Thr
    205                 210                 215 agc gtt tct gct gcg gta gga ggt tat aga gat aaa act gca tta gcc     844
Ser Val Ser Ala Ala Val Gly Gly Tyr Arg Asp Lys Thr Ala Leu Ala
220                 225                 230                 235 att ggt gtc ggc tca cgc att act gat cgc ttt acc gct aaa gcg ggt     892
Ile Gly Val Gly Ser Arg Ile Thr Asp Arg Phe Thr Ala Lys Ala Gly
```

```
                    Ile Gly Val Gly Ser Arg Ile Thr Asp Arg Phe Thr Ala Lys Ala Gly
                                    240                 245                 250 gta gcg ttc aat acc tac aat ggc ggc atg tct tat ggt gct tct gtt       940
Val Ala Phe Asn Thr Tyr Asn Gly Gly Met Ser Tyr Gly Ala Ser Val
                255                 260                 265 ggt tat gaa ttc taatcattac gtttaatcac taatcgtttt ggttataata            992
Gly Tyr Glu Phe
            270 aaaaggctaa atgtttctcc tcacatttag cctttcttat ttatctttgt tatagctttt     1052 gctgttataa aaccgttttt tagccacttt tattaattaa gcttttaagc ctattcaatc     1112 agttctactt tcactttttt caccatatta tccgccactt ctaaaacggt aatattaagt     1172 tggtttagcc taaattgggt accttctatc ggaattttt ctaaatgttc taaaattaa      1231

<210> SEQ ID NO 14
<211> LENGTH: 271
<212> TYPE: PRT
<213> ORGANISM: Haemophilus ducreyi

<400> SEQUENCE: 14
```

Met Lys Ile Lys Cys Leu Val Ala Val Gly Leu Ala Cys Ser Thr
1               5                   10                  15

Ile Thr Thr Met Ala Gln Gln Pro Pro Lys Phe Ala Gly Val Ser Ser
            20                  25                  30

Leu Tyr Ser Tyr Glu Tyr Asp Tyr Gly Lys Gly Lys Trp Thr Trp Ser
        35                  40                  45

Asn Glu Gly Gly Phe Asp Ile Lys Val Pro Gly Ile Lys Met Lys Pro
    50                  55                  60

Lys Glu Trp Ile Ser Lys Gln Ala Thr Tyr Leu Glu Leu Gln His Tyr
65                  70                  75                  80

Met Pro Tyr Thr Pro Val Leu Val Thr Ser Ala Pro Asp Val Pro Pro
                85                  90                  95

Ser Ser Ile Leu Leu Tyr Pro Met Ser Asp Pro Asp Gln Leu Gly Ile
            100                 105                 110

Asn Arg Gln Gln Leu Lys Leu Asn Leu Tyr Ser Tyr Phe Asn Asp Leu
        115                 120                 125

Arg His Asp Phe Lys Leu Lys Val Leu Asp Ala Arg Ile Ser Lys Asn
    130                 135                 140

Lys Gln Asn Ile Asp Thr Ile Ser Lys Tyr Leu Leu Glu Leu Gly Thr
145                 150                 155                 160

Tyr Leu Asp Gly Ser Tyr Arg Met Met Glu Gln Asn Thr His Asn Ile
                165                 170                 175

Asn Lys Asn Thr His Asn Ile Asn Lys Asn Thr His Asn Ile Asn Lys
            180                 185                 190

Leu Ser Lys Glu Leu Gln Thr Gly Leu Ala Asn Gln Ser Ala Leu Ser
        195                 200                 205

Met Leu Val Gln Pro Asn Gly Val Gly Lys Thr Ser Val Ser Ala Ala
    210                 215                 220

Val Gly Gly Tyr Arg Asp Lys Thr Ala Leu Ala Ile Gly Val Gly Ser
225                 230                 235                 240

Arg Ile Thr Asp Arg Phe Thr Ala Lys Ala Gly Val Ala Phe Asn Thr
                245                 250                 255

Tyr Asn Gly Gly Met Ser Tyr Gly Ala Ser Val Gly Tyr Glu Phe
            260                 265                 270

```
<210> SEQ ID NO 15
<211> LENGTH: 1047
<212> TYPE: DNA
<213> ORGANISM: Haemophilus ducreyi
<220> FEATURE:
<221> NAME/KEY: CDS
<222> LOCATION: (140)..(958)
<223> OTHER INFORMATION: DsrA strain M90-02

<400> SEQUENCE: 15
```

| | | |
|---|---|---:|
| ttttataatt tacaatacat tttatatttt tatattatat aaataccgtc attgacattt | | 60 |
| ttttaatgta aggtagaata agaaagtaaa ttctatattt acaatcaaga ttgacaatta | | 120 |
| tttacttaat gaggtgatt atg aaa att aaa tgt tta gtt gcc gta gtg gga<br>                                 Met Lys Ile Lys Cys Leu Val Ala Val Val Gly<br>                                  1            5                  10 | | 172 |
| tta gct tgt tct act att aca aca atg gct cag cag ccg cca aag ttt<br>Leu Ala Cys Ser Thr Ile Thr Thr Met Ala Gln Gln Pro Pro Lys Phe<br>              15                  20                  25 | | 220 |
| gct gga gta tct tct ttg tat agc tat gag tat gac tat ggt aag ggt<br>Ala Gly Val Ser Ser Leu Tyr Ser Tyr Glu Tyr Asp Tyr Gly Lys Gly<br>        30                  35                  40 | | 268 |
| aaa tgg act tgg tct aat gaa ggc ggt ttc gat att aaa gtg cca ggg<br>Lys Trp Thr Trp Ser Asn Glu Gly Gly Phe Asp Ile Lys Val Pro Gly<br>45                  50                  55 | | 316 |
| att aaa atg aag cca aaa gaa tgg att tct aaa cag gct act tat ctt<br>Ile Lys Met Lys Pro Lys Glu Trp Ile Ser Lys Gln Ala Thr Tyr Leu<br>60                  65                  70                  75 | | 364 |
| gaa tta cag cat tat atg cct tat act cct gtt ctc gtg aca tct gct<br>Glu Leu Gln His Tyr Met Pro Tyr Thr Pro Val Leu Val Thr Ser Ala<br>                  80                  85                  90 | | 412 |
| cct gac gtt tct cct agc tct atc tct ata ctg tta tat ccg atg tct<br>Pro Asp Val Ser Pro Ser Ser Ile Ser Ile Leu Leu Tyr Pro Met Ser<br>                      95                  100                105 | | 460 |
| gat cct gat caa ctt gga ata aat cgg cag cag ctg aaa ttg aat ttg<br>Asp Pro Asp Gln Leu Gly Ile Asn Arg Gln Gln Leu Lys Leu Asn Leu<br>           110                  115                120 | | 508 |
| tat agt tat ttt aac gat tta aga cac gat ttt aaa tta aaa gtt ctt<br>Tyr Ser Tyr Phe Asn Asp Leu Arg His Asp Phe Lys Leu Lys Val Leu<br>125                  130                135 | | 556 |
| gat gca cgt att tcc aaa aat aaa caa aat att gat act ata agt aaa<br>Asp Ala Arg Ile Ser Lys Asn Lys Gln Asn Ile Asp Thr Ile Ser Lys<br>140                  145                150                155 | | 604 |
| tat tta cta gaa ctg ggt act tat tta gat ggt tct tat cgt atg atg<br>Tyr Leu Leu Glu Leu Gly Thr Tyr Leu Asp Gly Ser Tyr Arg Met Met<br>                160                165                170 | | 652 |
| gaa caa aat aca cat aat atc aat aaa aat aca cat aat atc aat aaa<br>Glu Gln Asn Thr His Asn Ile Asn Lys Asn Thr His Asn Ile Asn Lys<br>175                  180                185 | | 700 |
| aat aca cat aat atc aat aag ttg tct aaa gaa ttg caa act ggt tta<br>Asn Thr His Asn Ile Asn Lys Leu Ser Lys Glu Leu Gln Thr Gly Leu<br>           190                  195                200 | | 748 |
| gcc aac caa tca gca ttg tct atg tta gtg caa cca aat ggt gta ggc<br>Ala Asn Gln Ser Ala Leu Ser Met Leu Val Gln Pro Asn Gly Val Gly<br>                205                210                215 | | 796 |
| aaa acg agc gtt tct gct gcg gta gga ggt tat aga gat aaa act gca<br>Lys Thr Ser Val Ser Ala Ala Val Gly Gly Tyr Arg Asp Lys Thr Ala<br>220                  225                230                235 | | 844 |
| tta gcc att ggt gtc ggc tca cgc att act gat cgc ttt acc gct aaa<br>Leu Ala Ile Gly Val Gly Ser Arg Ile Thr Asp Arg Phe Thr Ala Lys<br>                240                245                250 | | 892 |

```
gcg ggt gta gcg ttc aat acc tac aat ggc ggc atg tct tat ggt gct    940
Ala Gly Val Ala Phe Asn Thr Tyr Asn Gly Gly Met Ser Tyr Gly Ala
             255                 260                 265 tct gtt ggt tat gaa ttc taatcattac gtttaatcac taatcgtttt           988
Ser Val Gly Tyr Glu Phe
            270 ggttataata aaaaggctaa atgtttctcc tcacatttag cctttctta tttatctttt  1047
```

<210> SEQ ID NO 16
<211> LENGTH: 273
<212> TYPE: PRT
<213> ORGANISM: Haemophilus ducreyi

<400> SEQUENCE: 16

```
Met Lys Ile Lys Cys Leu Val Ala Val Gly Leu Ala Cys Ser Thr
1               5                   10                  15

Ile Thr Thr Met Ala Gln Gln Pro Pro Lys Phe Ala Gly Val Ser Ser
            20                  25                  30

Leu Tyr Ser Tyr Glu Tyr Asp Tyr Gly Lys Gly Lys Trp Thr Trp Ser
        35                  40                  45

Asn Glu Gly Gly Phe Asp Ile Lys Val Pro Gly Ile Lys Met Lys Pro
    50                  55                  60

Lys Glu Trp Ile Ser Lys Gln Ala Thr Tyr Leu Glu Leu Gln His Tyr
65                  70                  75                  80

Met Pro Tyr Thr Pro Val Leu Val Thr Ser Ala Pro Asp Val Ser Pro
                85                  90                  95

Ser Ser Ile Ser Ile Leu Leu Tyr Pro Met Ser Asp Pro Asp Gln Leu
            100                 105                 110

Gly Ile Asn Arg Gln Gln Leu Lys Leu Asn Leu Tyr Ser Tyr Phe Asn
        115                 120                 125

Asp Leu Arg His Asp Phe Lys Leu Lys Val Leu Asp Ala Arg Ile Ser
    130                 135                 140

Lys Asn Lys Gln Asn Ile Asp Thr Ile Ser Lys Tyr Leu Leu Glu Leu
145                 150                 155                 160

Gly Thr Tyr Leu Asp Gly Ser Tyr Arg Met Met Glu Gln Asn Thr His
                165                 170                 175

Asn Ile Asn Lys Asn Thr His Asn Ile Asn Lys Asn Thr His Asn Ile
            180                 185                 190

Asn Lys Leu Ser Lys Glu Leu Gln Thr Gly Leu Ala Asn Gln Ser Ala
        195                 200                 205

Leu Ser Met Leu Val Gln Pro Asn Gly Val Gly Lys Thr Ser Val Ser
    210                 215                 220

Ala Ala Val Gly Gly Tyr Arg Asp Lys Thr Ala Leu Ala Ile Gly Val
225                 230                 235                 240

Gly Ser Arg Ile Thr Asp Arg Phe Thr Ala Lys Ala Gly Val Ala Phe
                245                 250                 255

Asn Thr Tyr Asn Gly Gly Met Ser Tyr Gly Ala Ser Val Gly Tyr Glu
            260                 265                 270

Phe
```

<210> SEQ ID NO 17
<211> LENGTH: 1189
<212> TYPE: DNA
<213> ORGANISM: Haemophilus ducreyi
<220> FEATURE:
<221> NAME/KEY: CDS
<222> LOCATION: (139)..(909)

-continued

<223> OTHER INFORMATION: DsrA strain 406

<400> SEQUENCE: 17

```
attttataat ttacaataca ttttatttt tatattatat aaatacgtca ttgacatttt     60
tttaatgtaa ggtagaataa gaaagtaaat tctatattta caatcaagat tgacaattat    120
ttacttaatg aggtgatt atg aaa att aaa tgt tta gtt gcc gta gtg gga     171
                    Met Lys Ile Lys Cys Leu Val Ala Val Val Gly
                     1               5                  10 tta gct tgt tct act att aca aca atg gct cag cag ccg cca aag ttt     219
Leu Ala Cys Ser Thr Ile Thr Thr Met Ala Gln Gln Pro Pro Lys Phe
             15                  20                  25 gct gga gta tct tct ttg tat agc tat gag tat gac tat ggt aag ggt     267
Ala Gly Val Ser Ser Leu Tyr Ser Tyr Glu Tyr Asp Tyr Gly Lys Gly
         30                  35                  40 aaa tgg act tgg tct aat gaa ggc ggt ttc gat att aaa gtg cca ggg     315
Lys Trp Thr Trp Ser Asn Glu Gly Gly Phe Asp Ile Lys Val Pro Gly
     45                  50                  55 att aaa atg aag cca aaa gaa tgg att tct aaa cag gct act tat ctt     363
Ile Lys Met Lys Pro Lys Glu Trp Ile Ser Lys Gln Ala Thr Tyr Leu
 60                  65                  70                  75 gaa tta cag cat tat atg cct tat act cct gtt ctc gtg aca tat gct     411
Glu Leu Gln His Tyr Met Pro Tyr Thr Pro Val Leu Val Thr Tyr Ala
                 80                  85                  90 cct ggc gtt tct cct agc cct ata ctg tta tat ccg atg tct gat cct     459
Pro Gly Val Ser Pro Ser Pro Ile Leu Leu Tyr Pro Met Ser Asp Pro
             95                 100                 105 gat caa ctt gga ata aat cgg cag cag ctg aaa ttg aat ttg tat agt     507
Asp Gln Leu Gly Ile Asn Arg Gln Gln Leu Lys Leu Asn Leu Tyr Ser
        110                 115                 120 tat ttt aac gat tta aga cac gat ttt aaa tta aaa gtt ctt gat gca     555
Tyr Phe Asn Asp Leu Arg His Asp Phe Lys Leu Lys Val Leu Asp Ala
    125                 130                 135 cgt att tcc aaa aat aaa caa aat att gat act ata agt aaa tat tta     603
Arg Ile Ser Lys Asn Lys Gln Asn Ile Asp Thr Ile Ser Lys Tyr Leu
140                 145                 150                 155 cta gaa ctg ggt act tat tta gat gat tct tat cgt atg atg gaa caa     651
Leu Glu Leu Gly Thr Tyr Leu Asp Asp Ser Tyr Arg Met Met Glu Gln
                160                 165                 170 aat aca cat aat atc aat aag ttg tct aaa gaa ttg caa act ggt tta     699
Asn Thr His Asn Ile Asn Lys Leu Ser Lys Glu Leu Gln Thr Gly Leu
            175                 180                 185 gcc aac caa tca gca ttg tct atg tta gtg caa cca aat ggt gta ggc     747
Ala Asn Gln Ser Ala Leu Ser Met Leu Val Gln Pro Asn Gly Val Gly
        190                 195                 200 aaa acg agc gtt tct gct gcg gta gga ggt tat aga gat aaa act gca     795
Lys Thr Ser Val Ser Ala Ala Val Gly Gly Tyr Arg Asp Lys Thr Ala
    205                 210                 215 tta gcc att ggt gtc ggc tca cgc att act gat cgc ttt acc gct aaa     843
Leu Ala Ile Gly Val Gly Ser Arg Ile Thr Asp Arg Phe Thr Ala Lys
220                 225                 230                 235 gcg ggt gta gcg ttc aat acc tac aat ggc ggc atg tct tat ggt gct     891
Ala Gly Val Ala Phe Asn Thr Tyr Asn Gly Gly Met Ser Tyr Gly Ala
                240                 245                 250 tct gtt ggt tat gaa ttc taatcattac gtttaatcac taatcgtttt            939
Ser Val Gly Tyr Glu Phe
                255 ggttataata aaaaggctaa atgtttctcc tcacatttag cctttcttat ttatctttgt    999 tatagctttt gctgttataa aaccgttttt tagccacttt tattaattaa gcttttaagc  1059
```

```
ctattcaatc agttctactt tcacttttt caccatatta tccgccactt ctaaaacggt    1119
aatattaagt tggtttagcc taaattgggt accttctatc ggaatttttt ctaaatgttc    1179
taaaattaag                                                          1189
```

<210> SEQ ID NO 18
<211> LENGTH: 257
<212> TYPE: PRT
<213> ORGANISM: Haemophilus ducreyi

<400> SEQUENCE: 18

```
Met Lys Ile Lys Cys Leu Val Ala Val Val Gly Leu Ala Cys Ser Thr
1               5                   10                  15

Ile Thr Thr Met Ala Gln Gln Pro Pro Lys Phe Ala Gly Val Ser Ser
            20                  25                  30

Leu Tyr Ser Tyr Glu Tyr Asp Tyr Gly Lys Gly Lys Trp Thr Trp Ser
        35                  40                  45

Asn Glu Gly Gly Phe Asp Ile Lys Val Pro Gly Ile Lys Met Lys Pro
    50                  55                  60

Lys Glu Trp Ile Ser Lys Gln Ala Thr Tyr Leu Glu Leu Gln His Tyr
65                  70                  75                  80

Met Pro Tyr Thr Pro Val Leu Val Thr Tyr Ala Pro Gly Val Ser Pro
                85                  90                  95

Ser Pro Ile Leu Leu Tyr Pro Met Ser Asp Pro Asp Gln Leu Gly Ile
            100                 105                 110

Asn Arg Gln Gln Leu Lys Leu Asn Leu Tyr Ser Tyr Phe Asn Asp Leu
        115                 120                 125

Arg His Asp Phe Lys Leu Lys Val Leu Asp Ala Arg Ile Ser Lys Asn
    130                 135                 140

Lys Gln Asn Ile Asp Thr Ile Ser Lys Tyr Leu Leu Glu Leu Gly Thr
145                 150                 155                 160

Tyr Leu Asp Asp Ser Tyr Arg Met Met Glu Gln Asn Thr His Asn Ile
                165                 170                 175

Asn Lys Leu Ser Lys Glu Leu Gln Thr Gly Leu Ala Asn Gln Ser Ala
            180                 185                 190

Leu Ser Met Leu Val Gln Pro Asn Gly Val Gly Lys Thr Ser Val Ser
        195                 200                 205

Ala Ala Val Gly Gly Tyr Arg Asp Lys Thr Ala Leu Ala Ile Gly Val
    210                 215                 220

Gly Ser Arg Ile Thr Asp Arg Phe Thr Ala Lys Ala Gly Val Ala Phe
225                 230                 235                 240

Asn Thr Tyr Asn Gly Gly Met Ser Tyr Gly Ala Ser Val Gly Tyr Glu
                245                 250                 255

Phe
```

<210> SEQ ID NO 19
<211> LENGTH: 7
<212> TYPE: PRT
<213> ORGANISM: Haemophilus ducreyi

<400> SEQUENCE: 19

```
Asn Thr His Asn Ile Asn Lys
1               5
```

<210> SEQ ID NO 20
<211> LENGTH: 547

<210> TYPE: PRT
<213> ORGANISM: Moraxella catarrhalis

<400> SEQUENCE: 20

```
Gln Val Val Glu Gln Phe Phe Pro Asn Ile Phe Phe Asn Glu Asn His
1               5                   10                  15

Asp Glu Leu Asp Asp Ala Tyr His Asn Met Ile Leu Gly Asp Thr Ala
            20                  25                  30

Ile Val Ser Asn Ser Gln Asp Asn Ser Thr Gln Leu Lys Phe Tyr Ser
        35                  40                  45

Asn Asp Glu Asp Ser Val Pro Asp Ser Leu Leu Phe Ser Lys Leu Leu
    50                  55                  60

His Glu Gln Gln Leu Asn Gly Phe Lys Ala Gly Asp Thr Ile Ile Pro
65                  70                  75                  80

Leu Asp Lys Asp Gly Lys Pro Val Tyr Thr Lys Asp Thr Arg Thr Lys
                85                  90                  95

Asp Gly Lys Val Glu Thr Val Tyr Ser Val Thr Lys Ile Ala Thr
            100                 105                 110

Gln Asp Asp Val Glu Gln Ser Ala Tyr Ser Arg Gly Ile Gln Gly Asp
        115                 120                 125

Ile Asp Asp Leu Tyr Asp Ile Asn Arg Glu Val Asn Glu Tyr Leu Lys
    130                 135                 140

Ala Thr His Asp Tyr Asn Glu Arg Gln Thr Glu Ala Ile Asp Ala Leu
145                 150                 155                 160

Asn Lys Ala Ser Ser Ala Asn Thr Asp Arg Ile Asp Thr Ala Glu Glu
                165                 170                 175

Arg Ile Asp Lys Asn Glu Tyr Asp Ile Lys Ala Leu Glu Ser Asn Val
            180                 185                 190

Glu Glu Gly Leu Leu Glu Leu Ser Gly His Leu Ile Asp Gln Lys Ala
        195                 200                 205

Asp Leu Thr Lys Asp Ile Lys Ala Leu Glu Ser Asn Val Glu Glu Gly
    210                 215                 220

Leu Leu Glu Leu Ser Gly His Leu Ile Asp Gln Lys Ala Asp Leu Thr
225                 230                 235                 240

Lys Asp Ile Lys Ala Leu Glu Ser Asn Val Glu Glu Gly Leu Leu Asp
                245                 250                 255

Leu Ser Gly Arg Leu Leu Asp Gln Lys Ala Asp Ile Ala Lys Asn Gln
            260                 265                 270

Ala Asp Ile Ala Gln Asn Gln Thr Asp Ile Gln Asp Leu Ala Ala Tyr
        275                 280                 285

Asn Glu Leu Gln Asp Ala Tyr Ala Lys Gln Gln Thr Glu Ala Ile Asp
    290                 295                 300

Ala Leu Asn Lys Ala Ser Ser Glu Asn Thr Gln Asn Ile Ala Lys Asn
305                 310                 315                 320

Gln Ala Asp Ile Ala Asn Asn Ile Asn Asn Ile Tyr Glu Leu Ala Gln
                325                 330                 335

Gln Gln Asp Gln His Ser Ser Asp Ile Lys Thr Leu Ala Lys Ala Ser
            340                 345                 350

Ala Ala Asn Thr Asp Arg Ile Ala Lys Asn Lys Ala Asp Ala Asp Ala
        355                 360                 365

Ser Phe Glu Thr Leu Thr Lys Asn Gln Asn Thr Leu Ile Glu Lys Asp
    370                 375                 380

Lys Glu His Asp Lys Leu Ile Thr Ala Asn Lys Thr Ala Ile Asp Ala
385                 390                 395                 400
```

-continued

```
Asn Lys Ala Ser Ala Asp Thr Lys Phe Ala Ala Thr Ala Asp Ala Ile
                405                 410                 415
Thr Lys Asn Gly Asn Ala Ile Thr Lys Asn Ala Lys Ser Ile Thr Asp
            420                 425                 430
Leu Gly Thr Lys Val Asp Gly Phe Asp Gly Arg Val Thr Ala Leu Asp
        435                 440                 445
Thr Lys Val Asn Ala Leu Asp Thr Lys Val Asn Ala Phe Asp Gly Arg
    450                 455                 460
Ile Thr Ala Leu Asp Ser Lys Val Glu Asn Gly Met Ala Ala Gln Ala
465                 470                 475                 480
Ala Leu Ser Gly Leu Phe Gln Pro Tyr Ser Val Gly Lys Phe Asn Ala
                485                 490                 495
Thr Ala Ala Leu Gly Gly Tyr Gly Ser Lys Ser Ala Val Ala Ile Gly
            500                 505                 510
Ala Gly Tyr Arg Val Asn Pro Asn Leu Ala Phe Lys Ala Gly Ala Ala
        515                 520                 525
Ile Asn Thr Ser Gly Asn Lys Lys Gly Ser Tyr Asn Ile Gly Val Asn
    530                 535                 540
Tyr Glu Phe
545

<210> SEQ ID NO 21
<211> LENGTH: 430
<212> TYPE: PRT
<213> ORGANISM: Yersinia enterocolitica

<400> SEQUENCE: 21

Asp Asp Tyr Asp Gly Ile Pro Asn Leu Thr Ala Val Gln Ile Ser Pro
1               5                   10                  15

Asn Ala Asp Pro Ala Leu Gly Leu Glu Tyr Pro Val Arg Pro Pro Val
            20                  25                  30

Pro Gly Ala Gly Gly Leu Asn Ala Ser Ala Lys Gly Ile His Ser Ile
        35                  40                  45

Ala Ile Gly Ala Thr Ala Glu Ala Ala Lys Gly Ala Ala Val Ala Val
    50                  55                  60

Gly Ala Gly Ser Ile Ala Thr Gly Val Asn Ser Val Ala Ile Gly Pro
65                  70                  75                  80

Leu Ser Lys Ala Leu Gly Asp Ser Ala Val Thr Tyr Gly Ala Ala Ser
                85                  90                  95

Thr Ala Gln Lys Asp Gly Val Ala Ile Gly Ala Arg Ala Ser Thr Ser
            100                 105                 110

Asp Thr Gly Val Ala Val Gly Phe Asn Ser Lys Ala Asp Ala Lys Asn
        115                 120                 125

Ser Val Ala Ile Gly His Ser Ser His Val Ala Ala Asn His Gly Tyr
    130                 135                 140

Ser Ile Ala Ile Gly Asp Arg Ser Lys Thr Asp Arg Glu Asn Ser Val
145                 150                 155                 160

Ser Ile Gly His Glu Ser Leu Asn Arg Gln Leu Thr His Leu Ala Ala
                165                 170                 175

Gly Thr Lys Asp Thr Asp Ala Val Asn Val Ala Gln Leu Lys Lys Glu
            180                 185                 190

Ile Glu Lys Thr Gln Glu Asn Thr Asn Lys Arg Ser Ala Glu Leu Leu
        195                 200                 205

Ala Asn Ala Asn Ala Tyr Ala Asp Asn Lys Ser Ser Ser Val Leu Gly
```

```
                210                 215                 220
Ile Ala Asn Asn Tyr Thr Asp Ser Lys Ser Ala Glu Thr Leu Glu Asn
225                 230                 235                 240

Ala Arg Lys Glu Ala Phe Ala Gln Ser Lys Asp Val Leu Asn Met Ala
                245                 250                 255

Lys Ala His Ser Asn Ser Val Ala Arg Thr Thr Leu Glu Thr Ala Glu
                260                 265                 270

Glu His Ala Asn Ser Val Ala Arg Thr Thr Leu Glu Thr Ala Glu Glu
                275                 280                 285

His Ala Asn Lys Lys Ser Ala Glu Ala Leu Ala Ser Ala Asn Val Tyr
290                 295                 300

Ala Asp Ser Lys Ser Ser His Thr Leu Lys Thr Ala Asn Ser Tyr Thr
305                 310                 315                 320

Asp Val Thr Val Ser Asn Ser Thr Lys Lys Ala Ile Arg Glu Ser Asn
                325                 330                 335

Gln Tyr Thr Asp His Lys Phe Arg Gln Leu Asp Asn Arg Leu Asp Lys
                340                 345                 350

Leu Asp Thr Arg Val Asp Lys Gly Leu Ala Ser Ser Ala Ala Leu Asn
                355                 360                 365

Ser Leu Phe Gln Pro Tyr Gly Val Gly Lys Val Asn Phe Thr Ala Gly
                370                 375                 380

Val Gly Gly Tyr Arg Ser Ser Gln Ala Leu Ala Ile Gly Ser Gly Tyr
385                 390                 395                 400

Arg Val Asn Glu Asn Val Ala Leu Lys Ala Gly Val Ala Tyr Ala Gly
                405                 410                 415

Ser Ser Asp Val Met Tyr Asn Ala Ser Phe Asn Ile Glu Trp
                420                 425                 430

<210> SEQ ID NO 22
<211> LENGTH: 28
<212> TYPE: DNA
<213> ORGANISM: Haemophilus ducreyi

<400> SEQUENCE: 22
ttgacatttt tttaatgtaa ggtagaat                                    28

<210> SEQ ID NO 23
<211> LENGTH: 23
<212> TYPE: DNA
<213> ORGANISM: Haemophilus ducreyi

<400> SEQUENCE: 23
ttgacatttt tttaaggtag aat                                         23
```